(12) United States Patent
Leitch et al.

(10) Patent No.: US 8,227,572 B2
(45) Date of Patent: Jul. 24, 2012

(54) ARACHNOCAMPA LUCIFERASES

(75) Inventors: Virginia Leitch, Belconnen (AU); Mira Maria Dumancic, Oxley (AU); Stephen Charles Trowell, Oxley (AU); Helen Dacres, Monash (AU)

(73) Assignee: Commonwealth Scientific and Industrial Research Organisation, Australian Capital Territory (AU)

( * ) Notice: Subject to any disclaimer, the term of this patent is extended or adjusted under 35 U.S.C. 154(b) by 1068 days.

(21) Appl. No.: 12/063,938

(22) PCT Filed: Aug. 18, 2006

(86) PCT No.: PCT/AU2006/001180
§ 371 (c)(1),
(2), (4) Date: Feb. 15, 2008

(87) PCT Pub. No.: WO2007/019634
PCT Pub. Date: Feb. 22, 2007

(65) Prior Publication Data
US 2011/0015095 A1 Jan. 20, 2011

Related U.S. Application Data

(60) Provisional application No. 60/709,473, filed on Aug. 19, 2005.

(51) Int. Cl.
*C07K 14/00* (2006.01)
(52) U.S. Cl. ......................... 530/350; 530/300
(58) Field of Classification Search .................. None
See application file for complete search history.

(56) References Cited

U.S. PATENT DOCUMENTS

| | | | |
|---|---|---|---|
| 5,292,658 A | 3/1994 | Cormier et al. | |
| 5,418,155 A | 5/1995 | Cormier et al. | |
| 5,484,956 A | 1/1996 | Lundquist et al. | |
| 5,538,879 A | 7/1996 | Muller-Rober et al. | |
| 5,576,198 A | 11/1996 | McBride et al. | |
| 5,595,896 A | 1/1997 | Coruzzi et al. | |
| 5,618,722 A * | 4/1997 | Zenno et al. | 435/252.3 |
| 5,629,470 A | 5/1997 | Lam et al. | |
| 5,633,155 A | 5/1997 | Kim et al. | |
| 5,656,466 A | 8/1997 | Moon et al. | |
| 5,670,356 A | 9/1997 | Sherf et al. | |
| 5,674,731 A | 10/1997 | Lin et al. | |
| 5,689,045 A | 11/1997 | Logemann et al. | |
| 5,689,049 A | 11/1997 | Cigan et al. | |
| 5,739,409 A | 4/1998 | Fischer et al. | |
| 5,744,320 A | 4/1998 | Sherf et al. | |
| 5,750,870 A | 5/1998 | Mathews et al. | |
| 5,767,367 A | 6/1998 | Dudits et al. | |
| 5,807,522 A | 9/1998 | Brown et al. | |
| 5,837,832 A | 11/1998 | Chee et al. | |
| 6,068,979 A | 5/2000 | Akhavan-Tafti | |
| 6,143,502 A | 11/2000 | Grentzmann et al. | |
| 6,171,809 B1 | 1/2001 | Roelant | |
| 6,265,177 B1 | 7/2001 | Squirrell et al. | |
| 6,270,964 B1 | 8/2001 | Michnick et al. | |
| 6,274,320 B1 * | 8/2001 | Rothberg et al. | 435/6.12 |
| 6,297,018 B1 | 10/2001 | French | |
| 6,342,345 B1 | 1/2002 | Blau et al. | |
| 6,503,723 B1 | 1/2003 | van Lune et al. | |
| 6,586,196 B1 | 7/2003 | Bronstein et al. | |
| 6,602,657 B1 | 8/2003 | Bronstein et al. | |
| 6,602,658 B1 | 8/2003 | Bronstein et al. | |
| 6,690,461 B1 | 2/2004 | Tamura et al. | |
| 6,890,745 B1 | 5/2005 | Leng | |
| 6,927,037 B2 | 8/2005 | Kasten et al. | |
| 7,083,911 B2 * | 8/2006 | Wood et al. | 435/4 |
| 7,291,482 B2 * | 11/2007 | Cheng et al. | 435/69.1 |
| 7,323,305 B2 * | 1/2008 | Leamon et al. | 435/5 |
| 7,575,865 B2 * | 8/2009 | Leamon et al. | 435/6.12 |
| 7,884,066 B2 * | 2/2011 | Ting | 514/1.1 |
| 7,884,069 B2 * | 2/2011 | Schaebitz et al. | 424/85.1 |
| 7,884,263 B2 * | 2/2011 | Dewey et al. | 800/285 |
| 2003/0166905 A1 | 9/2003 | Wood et al. | |
| 2004/0224377 A1 | 11/2004 | Hawkins et al. | |
| 2004/0235077 A1 | 11/2004 | Hattori et al. | |
| 2005/0026171 A1 | 2/2005 | Hawkins et al. | |
| 2005/0079567 A1 | 4/2005 | Kim Choi et al. | |
| 2005/0089964 A1 | 4/2005 | Viviani et al. | |

FOREIGN PATENT DOCUMENTS

| | | |
|---|---|---|
| EP | 0 449 621 B1 | 8/1996 |
| WO | WO 92/15673 A1 | 9/1992 |
| WO | WO/95/11995 A1 | 5/1995 |
| WO | WO 98/46729 | 10/1998 |
| WO | WO 99/49019 A2 | 9/1999 |
| WO | WO/99/66324 A2 | 12/1999 |
| WO | WO/00/24878 A2 | 5/2000 |
| WO | WO 2005/035719 A2 | 4/2005 |
| WO | WO 2005/038029 A2 | 4/2005 |

OTHER PUBLICATIONS

International Search Report, mailed Oct. 31, 2006.
Supplementary European Search Report, mailed Dec. 29, 2008.
Angers, S., A. Salahpour, et al. Proc Natl Acad Sci U S A 97(7): 3684-9 (2000).
Baker, C. (2004). Australian glow-worms (Diptera: Keroplatidae: Arachnocampa spp.): distribution, diversity, identity and management. Ph. D. Thesis, Department of Zoology and Entomology, University of Queensland, Brisbane: 186pp.
Branchini, B. R., Magyar R.A., et al., Biochemistry 37(44): 15311-9 (1998).
Branchini, B. R., Magyar R.A., et al., Biochemistry 40(8): 2410-8 (2001).
Branchini, B. R., Southworth T.L., et al., Biochemistry 42(35): 10429-36 (2003).
Branchini, B. R. et al., Biochemistry 43(23), 7255 (2004).
Conti et al., Acta Crystallogr D Biol Crystallogr. 1996 M 1;52(Pt 4):876-8.

(Continued)

*Primary Examiner* — Hope Robinson
(74) *Attorney, Agent, or Firm* — Brinks Hofer Gilson & Lione

(57) ABSTRACT

Nucleotide and amino acid sequences of luciferase peptides that are encoded by genes within the genome of *Arachnocampa* (Diptera) are disclosed. Specifically provided are functional ATP-dependent luciferases that catalyze luminescence reactions with emission spectra within the blue portion of the spectrum. The present invention specifically provides isolated peptide and nucleic acid molecules, methods of identifying orthologs and active subsequences of the enzyme peptides, and methods of identifying modulators and substrates of the luciferase peptides. Methods of assays, including multiple reporter assays utilizing at least two ATP-dependent luciferases are provided.

4 Claims, 34 Drawing Sheets

OTHER PUBLICATIONS

Conti, E., Franks N.P., et al., Structure 4(3): 287-298 (1996).
Colepicolo-Neto, P. et al., Insect Biochem. 16(5), 803 (1986).
Day, J. C, L. C. Tisi, et al, Luminescence 19(1): 8-20 (2004).
De Cock, R., (2004) Photochemistry and Photobiology, 79(4): 339-342.
de Wet, J. R., Wood K.V., et al., Molecular and Cellular Biology 7(2): 725-37 (1987).
de Wet, J. R. et al., Proc. Natl. Acad. Sci. USA, 82(23), 7870 (1985).
Devine, J. H. et al., Biochim. Biophys. Acta, 1173(2), 121 (1993).
Fulton, B. B., Annals of the Entomological Society of America 34: 289-302 (1941).
Gatenby, J. B. Trans. Roy. Soc. New Zealand 88(3), 577 (1960).
Gould, S. J. and Subramani, S., Anal. Biochem., 175(1), 5 (1988).
Hammarström M., et al., (2002) Protein Science 11: 313-321.
Harrison, R. A., Pacific Insects 8(4): 877-833 (1966).
Hastings, J.W., Gene 173(1): 5-11 (1996).
Herring, P. J., J Biolumin Chemilumin 1(3), 147 (1987).
Jain, V. K. and Magrath, I. T., BioTechniques: 12, 681-683 (1992).
Kozak, M., Cell 44(2): 283-92 (1986).
Kozak, M., Nucleic Acids Res 15(20): 8125-48 (1987).
Lawler-Sagarin, K., The Chemistry of Color Web Site, printed May 29, 2006.
Leckie, F. et al., BioTechniques: 17, 52-57 (1994).
Lee, J., Photochemistry and Photobiology 24: 279-285 (1976).
Lundin, A., Methods Enzymol 305: 346-70 (2000).
Masuda et al., Gene 77, 265-270 (1989).
Morton, R. A. et al., Biochemsitry 8(4), 1598 (1969).
Nakajima, Y. et al., Bioscience Biotechnology Biochemistry, Japan Soc. For Bioscience, Biotechnology and Agrochem 68(4):948-951 (2004).
Nakajima, Y., et al., FEBS Letters 565(1-3):122-126 (2004-2005).
Nakatsu, T. et al., Nature 440:372-376 (2006).
Niwa et al., FEBS Letts 580(22), 5283 (2006).
Oba, Y. et al., Gene 329, 137 (2004).
Oba, Y. et al., FEBS Letts 540(1-3), 251 (2003).
Orlova, G. et al., J. Am. Chem. Soc. 125(23), 6962 (2003).
Promega: Instructions for use of Products E2920, E2940, and E2980, revised Jan. 2006, Part No. TM058. and Promega pGL3 Luciferase Reporter Vectors (available from Promega Corporation, Madison, Wis.).
Pugsley, C. W., New Zealand Entomologist 7(4): 419-424 (1983).
Seliger, H. H. and McElroy, W.D., Arch Biochem Biophys 88: 136-41 (1960).
Shimomura, O., F. H. Johnson, et al., Observations on the biochemistry of luminescence in the New Zealand glowworm, Arachnocampa luminosa., Bioluminescence in Progress. F. H. Johnson and Y. Haneda. Princeton, Princeton University Press: 487-494 (1966).
Shimomura, O., FEBS Letters 128(2):242-244 (1981).
Sivinski, J. M. (1998). Florida Entomologist 81(3): 282-292.
SwissProt Acc No. P08659., Jan. 1, 1988.
Takaie, H. (1989) Breeding and display of the glow-worms, Arachnocampa spp., Insectarium, vol. 26 July: 214-219.
Takaie, H. (1997) Ten years of the glow-worm (Arachnocampa richardsae) rearing at Tama Zoo—Fascination of a living milky way., Insectarium, vol. 34 November: 336-342.
Tatsumi, H. et al., Biochim. Biophys. Acta 1131(2), 161 (1992).
Tatsumi, H. et al., J. Biolumin. Chemilumin. 3(2), 75 (1989).
Thompson, E.M. et al. PNAS 86:6567-6571 (1989).
Viviani, Hastings et al., Photochem Photobiol. 75(I):22-7 (2002).
Viviani, Hastings et al., Photochem Photobiol. 76 (5):538-544 (2002).
Viviani, V.R. et al., Photochem and Photobiol. 70(2): 254-260 (1999).
Viviani, V. R., Cell. Mol. Life Sci. 59:1833-1850 (2002).
Viviani V.R. et al., Biochemistry, 38, 8271-8279 (1999).
White, E. H. et al., J. Am. Chem. Soc., 85, 337 (1963).
White, E. H. et al., J. Am. Chem. Soc., 83, 2402 (1961).
Wilson, Therese, Email dated Feb. 23, 2008.
Wood, K. V., (1998) The Chemistry of Bioluminescent Reporter Assays, Promega Notes 65, p. 14.
Wood et al., Science 244, 700-702 (1989).
Wood et al., Journal of Bioluminescence and Chemiluminescence 4(1): 289-301 (1989).
Wood, K. V., Evolution of bioluminescence in insects. VII International Symposium on Bioluminescence and Chemiluminescence, Wiley, Chichester, UK (1983).
Wood, K. V. Photochem. Photobiol, 62(4), 662 (1995).
Xu, Y., D. W. Piston, et al, Proc Natl Acad Sci U S A 96(1): 151-6 (1999).
Examination Report from New Zealand Application No. 565938, dated Feb. 26, 2010, 2 pages.
European Patent Office Communication and Extended European Search Report for European Application No. 06774822.8; Dated Dec. 29, 2008.
Intellectual Property Office of New Zealand Examination Report for New Zealand Patent Application No. 565938; Dated Feb. 26, 2010.

* cited by examiner

Consensus cDNA_SEQUENCE of Arachnocampa richardsae luciferase     (SEQ ID NO: 1)

Length: 1713  June 15, 2005 20:24  Type: N  Check: 8482  ..

```
    1  ATCAATTGTC TTGTGAAATT CTCAGTGACA ATGGCTTGTA CTTCAGTGAA
   51  TAATATTGTA TATGGTCCTA AGCCGACCTT TGATGTCTTG AAGGAGGCTA
  101  ATTCGTATGG TGAATATGCA TTTAAACGAT TGAGAGCCAG AGGTGATGAA
  151  GTTTCAGTTA TTGATGCCCT AACAGGAGAG GAAATTGGTG CATCCGATAT
  201  TTATGCTAAG ACCGTGCGAA CAGCTGAGTG TCTTCAAGCT TATGGCATCA
  251  GAAAGGGCGA TCGTGTTGGT ATTTGCAGTG ATACCATGAT TGAATACTAT
  301  TACATTGTAA TGGGAACAAT GGCAGTTGGT GCTATTATCT GTCCAATTAT
  351  TATTTCATGG ACTGAAGCCG ACATGAACCA TGCTTTTAAT ATTTCATGTC
  401  CAACGGTTTT CTTTGTTTCG AAAAGTATTT TGCCAACGAT TGCTCGAATT
  451  GCTAAGAGAA ATCCTTATGT AAAGGACATT ATTGTCTTTG ATGATAATGC
  501  ACCAGAAAAG CCATTGAIAA GCTTTAAAGA TTTTTTGGCT AATCCAAAAG
  551  TGCCATGAAA ACCACATTTT GATTGTGAAC CACAAGACAT GGAAAATACC
  601  ATTGCCACTG TTTTATTGAC ATCTGGTACT ACGGTATTT CTAAAGGTGT
  651  TGCTATATCG CAATATAATC TGATCCACTT CATGTCACTG GACACTAAGA
  701  CTTACAAGAA GGGCCTATTT TTGTGTGTAG CACGGTACTC TAATGCGTTT
  751  GGTTTTACTG CATTGATGAG ACGTGCATTT AATGCACCA GGGTACTTCA
  801  TTTGCCAAGA TATGACGAGA AGAGTTACTT AGAATGCGTT CAAAAATTCA
  851  AGGTCAATTA CATCAGTGTT CACCCTCCCT TGATTTGTC ATTAGCTAAG
  901  AAACCCGAAA TTGCGAACTA TGATTTGTCT AGTCTTGAAC GTATTTATTG
  951  CTCTGGTACA ACAGTGAGTG TTCGAATTTT ATATCAAGTA GCTGAGAGAA
 1001  TTGGCGTCAA GGTCGTACGT CAATTTTATG GATCCAGTGA ATGTTTGGCG
 1051  GTCGTTGCTC AAAGTGATGA ATTTGTACC AAAGGAAGTG TTGGTACACT
 1101  TATGCCTGGA ATTATTGGCA AAGTTATACA TCCAGAAACT GGTGCCCTTC
 1151  TTGGGCCAAA TGAACGCGGT TTCTTGAAAT TTAAGGCTAA CAGCACTATG
 1201  TATGGTTATT TCAACAATCC TGAAGCCTCC AAAGTTGTTA AAGATGAAGA
 1251  GGGTTATGTT AATACTGGTG ATGCTGGATA TTATAATGAA AGATTTGAAT
```

FIG. 1A (SEQ ID NO: 1; CONT.)

```
1301  GGTTCGTTGt TGATAGATTA AAGGATATAG TTATGGTCGA TGGTGTAGCC
1351  GTTGCACCAA CAGAAATGGA AACTACCATA TTGCTTCATC CCGATATTAT
1401  TGATGCTTGT GTCATTGGTA TCTCTGATGG TGAAGGTGGT GAAGTATTAT
1451  TTGCATTCTT GACTAAGACT AGGAAAGAGG TTACTGAAAA AGaTGTCATG
1501  GACTTCGTTG CAGAAAAACT ACCTTATCCC AAGCATCTTA AAGGTGGCTG
1551  CCAATTTGTT GATGAAATAC CCAAGAATCC AGCTGGCAAA ATGTTGCGTC
1601  GTATTTTAAG AGGAACATTG TAAATTGAAA AAATAATTTG TTTCTTATTT
1651  AATTTGAAAT AAATGCGATT GCATATAAAA GAAAAAAAAA AAAAGAAAAA
1701  AAAAAAAAAA AAA
```

Arachnocampa richardsae luciferase    (SEQ ID NO: 2)

1  MACTSVNNIV  YGPKPTFDVL  KEANSYGEYA  FKRLRARGDE  VSVIDALTGE
    51  EIRASDIYAK  TVRTAECLQA  YGIRKGDRVG  ICSDTMIEYY  YIVMGTMAVG
   101  AIICPIIISW  TEADMNHAFN  ISCPTVFFVS  KSILPTIARI  AKRNPYVKDI
   151  IVFDDNAPEK  PLISFKDFLA  NPKVPSKPHF  DCEPQDMENT  IATVLLTSGT
   201  TGISKGVAIS  QYNLIHPMSL  DTKTYKKGLF  LCVAQYSRAF  GFTALMRRAF
   251  NGTRVLHLPR  YDEKSYLECV  QKFKVNYISV  HPPLMLSLAK  KPEIANYDLS
   301  SLERIYCSGT  TVSVRILYQV  AERIGVKVVR  QFYGSSECLA  VVAQSDEPCT
   351  KGSVGTLMPG  IIGKVIHPET  GALLGPNERG  FLKFKANSTM  YGYFNNPEAS
   401  KVVKDEEGYV  NTGDAGYYNE  RFEWFVVDRL  KDIVMVDGVA  VAPTEMETTI
   451  LLHPDIIDAC  VIGISDGEGG  EVLFAFLTKT  RKEVTEKDVM  DFVASKLPYF
   501  KHLKGGCQFV  DEIPKNPAGK  MLRRILRGTL  *

FIG. 3

Nucleotide sequence of GWLuc#1    (SEQ ID NO: 3)

```
ATCAATTGTCTTGTGAAATTCTCAGTGACAATGGCTTGTACTTCAGTGAATAATATTGTATATGGTCCTAAGCCGA
CCTTTGATGTCTTGAAGGAGGCTAATTCGTATGGTGAATATGCATTTAAACGATTGAGAGCCAGAGGTGATGAAGT
TTCAGTTATTGATGCCCTAACAGGAGAGGAAATTCGTGCATCCGATATTTATGCTAAGACCGTGCGAACAGCTGAG
TGTCTTCAAGCTTATGGCATCAGAAAGGGCGATCGTGTTGGTATTTGCAGTGATACCATGATTGAATACTATTACA
TTGTAATGGGAACAATGGCAGTTGGTGTCTATTATCTGTCCAATTATTATTTCATGGACTGAAAGCCGACATGAACCA
TGCTTTTAATATTTCATGTCCAACGGTTTTCTTTGTTTCGAAAAGTATTTTGCCAACGATTGCTCGAATTGCTAAG
AGAAATCCTTATGTAAAGGACATTATTGTCTTTGATGATAATGCACCAGAAAAGCCATTGATAAGCTTTAAAGATT
TTTGGCTAATCCAAAAGTGCCATCAAAACCACATTTTGATTGTGAACCACAAGACATGGAAAATACCATTGCCAC
TGTTTTATTGACATCTGGTACTACCGGGTATTCTAAAGGTGTTGCTATATCGCAATATAATCTGATCCACTTCATG
TCACTGGACACTAAGACTTACAAGAAGGGCCTATTTTTGTGTGTAAGCACAGTACTCTAATGCCGTTTGGTTTTACTG
CATTGATGAGACGTGCATTTAATGGCACCAGGGTACTTCATTTGCCAAGATATGACGAGAAGAGTTACTTAGAATG
CGTTCAAAAATTCAAGGTCAATTACATCAGTGTTCACCCTCCCTTGATGTTGTCATTAGCTAAGAAACCCGAAATT
GCGAACTATGATTTGTCTAGTCTTTGAACGTTATTTATTGCTCTGGTACAACAGTGAGTGTTCGAATTTTATATCAAG
TAGCTGAGAGAATTGGCGTCAAGGTCGTACGTCAATTTTATGGATCCAGTGAATGTTTGGCGGTCGTTGCTCAAAG
TGATGAATTTGTACCAAAGGAAGTGTTGGTACACTTATGCCTGGAATTATTGGCAAGTTATACATCCAGAAACT
GGTGCCCTTCTTGGGCCAAATGAACGCGGTTTCTTGAAATTTAAGGCTAACAGCACTAIGTATGGTTATTTCAACA
ATCCTGAAGCCTCCAAAGTTGTTAAAGATGAAGAGGGTTATGTTAATACTGGTGATGCTGGATATTATAATGAAAG
ATTTGAATGGTTCGTTGCTGATAGATTAAAGGATATAGTTATGGTCGATGGTGTAGCCGTTCCACCAACAGAAATG
GAAACTACCATATTGCTTCATCCCGATATTATTGATGCTTGTGTCATTGGTATCTCTGATGGTGAAGGTGGTGAAG
TATTATTTGCATTCTTGACTAAGACTAGGAAAGAGGTTACTGAAAAAGAGTGTCATGGACTTCGTTGCAGAAAAACT
ACCTTATCCCAAGCATCTTAAAGGTGGCTGCCAATTTGTTGATGAAATACCCAAGAATCCAGCTGGCAAAATGTTG
CGTCGTATTTTAAGGAGGAACATTGTAAATTGAAAAAATAATTTGTTTCTTATTTAATTTGAAATAAATGCGATTGC
ATATAAGCAAAAAAAAAAAAAAAAAAAAAAAAAAAA
```

FIG. 4

Nucleotide sequence with amino acid translation of GWLuc#1

*Photinus pyralis* luciferase amino acid sequence (SEQ ID NO: 4)

```
MEDAKNIKKGPAPFYPLEDG TAGEQLHKAMKRYALVPGTI
AFTDAHIEVNITYAEYFEMS VRLAEAMKRYGLNTNHRIVV
CSENSLQFFMPVLGALFIGV AVAPANDIYNERELLNSMNI
SQPTVVFVSKKGLQKILNVQ KKLPIIQKIIIMDSKTDYQG
FQSMYTFVTSHLPPGFNEYD FVPESFDRDKTIALIMNSSG
STGLPKGVALPHRTACVRFS HARDPIFGNQIIPDTAILSV
VPFHHGFGMFTTLGYLICGF RVVLMYRFEEELFLRSLQDY
KIQSALLVPTLFSFFAKSTL IDKYDLSNLHEIASGGAPLS
KEVGEAVAKRFHLPGIRQGY GLTETTSAILITPEGDDKPG
AVGKVVPFFEAKVVDLDTGK TLGVNQRGELCVRGPMIMSG
YVNNPEATNALIDKDGWLHS GDIAYWDEDEHFFIVDRLKS
LIKYKGYQVAPAELESILLQ HPNIFDAGVAGLPDDDAGEL
PAAVVLEHGKTMTEKEIVD YVASQVTTAKKLRGGVVFVD
EVPKGLTGKLDARKIREILI KAKKGGKSKL
```

FIG. 9

(SEQ ID NO: 5)

```
   1 ATGGCTTGTACTTCAGTGAATAATATTGTATATGGTCCTAACCGACCTTTGATGTCTTG
  61 AAGGAGGCTAATTCGTATGCCTATGGTTGATATGCCATTTAAACCGATTGAGAGGTGACGAA
 121 GTTTCAGTTATTGATGCCCTAACGTGTCTTCAAGGAGGAGAGTTCGTTGCATCCGATATTATGCTAAG
 181 ACCGTGCCAACAGCTGAGTGTTCTTCAAGTCATGCGATATCAGGAAGGGGATCGTGTTGGT
 241 ATTTGCAGTGATACCATGATTGAATACTATTACATTGTAATGGGAACAATGGCAGTTGGT
 301 GCTATTATCGTCCAATTATTATTTCATGGACTCAAGCCCACATGAACCATGCTTTTAAT
 361 ATTTCATGTCCAACGGTTTCTTGTTCAAAAGTATTTGCAAGATTGCTCGAATT
 421 GCTAAGAGAAATCCTTATGTAAGGACATTATTGTCTTTGATGATGATGCACCAGAAAAC
 481 CCATTAATAGCTTAAAGATTTTTGGCTAATCCCAAGTGCCATCAAAACCACATTT
 541 GATTGTGAACCTCAAGACATGGAAAAATACCATTCCCACTGTTTATTGACATCGGTACA
 601 ACGGGTATTTCTAAAGGTGTTCCTATATCGCAATATAATCTGATCACAGTACTCTAATG
 661 GACACTAAGACTTACAAGAAGACGTGCGTTTGTGTAGCACCAGGGTACTCCATTTACCAAGA
 721 GGTTCACTGCATTGATGAGACTGGTACTTGCTAATTCAAGTCAATTGCTAACTATGATTGTCT
 781 TATGACGAAAAGAGTTACTGCGAATTGTGTTGTTCAAAAATTTCAAGTCAATTACATCACTGTT
 841 CATCCTCCCTTGATGTTGTTATTGTTCTCGCTACAACAGTGAGTGTTCGAATTTTATATCAAGTA
 901 AGTCTTGAACGTATTGTTGGCGTCAAGGTCGTAGTCGTCAATTTATGGATCGATGGTTTGGCA
 961 GCTGAGAGACTTGCGTCAAGGTCGATTTGTACCAAAGGAAGTTGGTACACTCATGCCTGGA
1021 GTCGTTGCTCAAAGTGCAAAGTTATACATCCTGAAACTGGTGCCCCTTCTTATTCAATGAACCGGGT
1081 ATTATTGCCAAGTTATACATCCTGAAACTGGTGCCCCTTCTTATTCAATAATCCTGAACCCTCC
1141 TTCTGAAATTAAGGCTAACGACTAGTGTTAATACGGTATTAAAGGATGTCGATATTATAATGAA
1201 AAGTTGTTAAAGATCAAGAAGAGAATGTTAAAGATACTGGTGATGCTGGATATATAATGAAGCC
1261 AGATTTGAATGCTTCGTTGTGTGCATAGATTAAAAGGATATAGTAATGGTCGATGGTGTAGCC
1321 GTTGCACCAACGAAATGGAAACTACCACTATTGCTTCATCCCGATATTATTGATGCTGT
1381 GTCATTGGTATCCTCGATGGTGAGGGTTGAAGTGGTGAAGTCATCATTGCTTGACTAAGACT
1441 AGGAAGAGAGTTACTGAAAGATGTCGAAAAAGATCTCATGGACTTTGATGATGAATACCCCATACCC
1501 AAGCATCTTAAAGGTTGGCTGCCAATTTGTGATGAAATAACCAAGATCCAGCTGTAA
1561 ATGTTTCCGTCCGTATTTTAAGAGGAACATTGTAA
```

FIG. 10

(SEQ ID NO: 6)

```
  1  MACTSVNNIVYGPKPTEDVLKEANSYGEYAFKRLRARGDEVSVIDALIGEEIRASDIYAK
 61  TVRTAECLQAYGIRKGDRVGICSDTMIEYYIVMGTMAVGAIICPIISWTEADMNHAFN
121  ISCPTVFFVSKSILPTIARIAKRNPYVKDIIVFDDDAPEKPLISFKDELANPKVPSKPHF
181  DCEPQDMENTIATVLLTSGTTGISKGVAISQYNLIHFMSLDTKTYKKGLFLCVAQISNAF
241  GFTALMRRAFNGTRVLHLPRYDEKSYLECVQKEKVNYISVHPPLMLSLAKKPEIANYDLS
301  SLERIYCSGTTVSVRILYQVAERLGVKVVRQFYGSSECLAVVAQSDEFCTKGSVGTLMPG
361  IIGKVIHPETGALIGPNERGFLKFKANSTMYGFNNPEASKVVKDEEGYVNTGDAGYYNE
421  RFEWFVVDRLKDIVMDGVAVAPTEMETTILLHPDIIDACVIGISDGEGGEVLFAFLTKT
481  RKFVTEKDVMDFVAEKLPYPKHLKGGCQFVDEIPKNPAGKMLRRIILRGTL*
```

FIG. 11

(SEQ ID NO: 7)

```
   1 ATGGCTTGTACTTCAGTGAATAATATTGTATATGGTCCTAAACCGACCTTTGATGTCTTG
  61 AAGGAGGCTAATTCGTATGCTCTACAGGAGAAGAATTCGTGCTTCCGATATTTATGCTAAG
 121 GTTTCAGTTATTGATGCTCTCAACAGGAGAAGAATTCGTGCTTCCGATATTTATGCTAAG
 181 ACGGTGCGAACAGTGAGTGCCTTCAAGCTTATGGCATCAGAAAGGCGATCGTGTTGGT
 241 ATTTGCAGTCGATACCATGATGATTGATTACATTGTCATGGGACAACAATGGCCAGTTGGT
 301 GCTATTATCTGTCCAATTATTATTCATGGACCAAGGCGACATGAACCATGCTTTAAT
 361 ATTTCATGTCCCACGGTTTCTTTGTTCTTTGTAAAGGACATTATGTCTTTGATGTAATGCACCAGAAAG
 421 GCTAAGAGAAATCCTTATGTAAAGATTTTTGGCTAATGCCATCAAAACCACATTTT
 481 CCATTGAACCACCATGGAAATACTATGCTGTTTATGACATCTGGTACT
 541 GATTGTGAACCACACAGACATGGAAATACTATGCTGTTTATGACATCTGGTACT
 601 ACGGGTATTTCTAAAGGTGTTGCTATATCGCAATATAATCTAATTCACTTCATGTCACTG
 661 GACACAAGAAGCTACAAGAAGGCCTGTTTGTGTGTAGCACAGTACTCCATTTACCAAGA
 721 GGTTTTACTGCATTGATGAGACGTACTTGAATGCGTTCCAGGGTACTCCATTTACCAAGA
 781 TATGACGAAAAGAGTACTTGAATGCGTTCAAGAATTCAAGTCAATTACATCAGTGTT
 841 CATCCCTCCCCTTGATCGTCGTTCATTAGTCAAGAAACCCGAAATTGCTAACTATGATTGTCT
 901 AGTCTTGAACGACTTGGCGTCAAGTCGTACGTCGTACGTCGAGTGTTCGAATTTTATACAAGTA
 961 GCTGAGAGAACTTGGCGTCAAGTCGATGAATTTGTACCAAGGAAGTTGCTCACTCATGCCTGGA
1021 GTCGTTGCTCAAAGTGCTCAAGTGATGAATTTGTACCAAGGAAGTTGCTCACTCATGCCTGGA
1081 ATTATTGCAAAATTTAAGGCTACAGAAGATATGCTTAATGTTAATACTGGTGATATATAATGAA
1141 TTCTTGAAATTTAAGGATGTCGTTGTTGAGATTGAATGTTAATACTGGTGATATTATAATGAA
1201 AAGTTGTTAAAGATGAATTGTCGTTGTTGATAGAATGTTAATACTGGTGATATTATAATGAA
1261 AGATTGAATGGTCGTTGTTGAATAGAATTAATGCTTCATCCCGATATTATGATGCTTGT
1321 GTTGCACCAACAGAATGTTGTTGTTGAAATAGAATTAATCTGAAGTATTGAAGTATCTTGACTAAGACT
1381 GTCATTGGTATCTCGATGGTGAAGGTGAAGTTGAAGTATTATTCTTGACTAAGACT
1441 AGGAACAGGTTACTGAAAAAGATGTCATGGACTTTGTGCAGAAAAACTACCTTATCCC
1501 AACCATCTTAAGGCGCTGCCAATTGTTGATGAATACCAAGCTGGCAAA
1561 ATGTTGCGTCGTATTTTAAGAGGAACATTGTAA
```

FIG. 12

(SEQ ID NO. 8)

```
  1  MACTSVNNIVYGPKPTFDVLKEANSYGEYAFKRLRARGDEVSVIDALIGEEIRASDIYAK
 61  TVRTAECLQAYGIRKGDRVGICSDTMIEYYIVMGTMAVGAIICPIISWTEADMNHAFN
121  ISCPTVFFVSKSILPTIARIAKRNPYVKDIIVFDDNAPEKPLISEKDFLANPKVPSKPHF
181  DCEPQDMENTIATVLLTSGTTGISKGVAISQYNLIHFMSLDTKTYKKGLFLCVAQYSNAF
241  GFTALMRRAFNGTRVLHLPRYDEKSYLECVQKFKVNYISVHPPLMLSLAKKPETANYDLS
301  SLERIYCSGTTVSVRILYQVAERLGVKVVRQFYGSSECLAVVAQSDEFCTKGSVGTLMPG
361  IIGKVIHPETGALLGPNERGFLKFKANSTMYGYFNNPEASKVVKDEEGYVNTGDAGYYNE
421  RFEWFVDRLKDIVMVDGVAVAPTEMETTILHPDIIDACVIGISDGEGGEVLFAFLIKT
481  RKEVTEKDVMDFVAEKLPYPKHLKGGCQFVDEIPKNPAGKMLRRILRGTIL*
```

FIG. 13

(SEQ ID NO: 9)

```
   1 ATGACTTCTACACTCTGTGGATAATATCGTTTATGCCCAAAACCAAAAATTCGATGTTCTA
  61 AAGGAGGCCAATTCTTATGGTGAATATACATTTAAACGGTTGAGAGCCAGAGGTGATGAG
 121 GTTTCAGTTATCGATCGGCGTTACCGGGACGAGCTTCCACATTTATGCCAAA
 181 ACGGTACGAACAGCTGAAGTCTCAAGCCTATGGCATTAGGAAGGCGCATTGGT
 241 ATTTGCAGTGACACAATGATGATTGAAATATTACTATATGTAATGGGAACAATGGCTGTTGGC
 301 GCTATCATTTGCCCCTGTAATTATTTCATGGACGGAAGCCGACATGACCATGCTTTCAAT
 361 ATTTCATGTCCAAGGGTCTTCTGTCTCAAAAAGTATTCTACCAACAATTGCTAAATTA
 421 TCAAGAGGAATCCTTATGTAAAGGATAATCATTGTTTTGACGATCAGTCACCTGAGAAG
 481 CCATTTATAAGCTTCAAAGATTTCTTGGCAAGTTCAAAGTTCCACTCGTTTATGTACATCGGTACT
 541 GATTGTGAACCACAAGATATGGAAAGTACTATTGCCACTCGTTTAGTACATCTGGTACT
 601 ACGGGTATTTCTAAAGGTGTTGCCATATCCCAATATAATCTGATCCACTTCATGTCATTG
 661 GATACTAAAAATGACAAGAAGTCTATTCTGTGGCTGGCTCAGTATTCGAATGCTTTT
 721 GGTTTACGGCATTGATGCACGTGCATTAATGCGTTCAAAAATACAAGTAACTATAGCGTC
 781 TATGAAGAAAAGCATATTTGCCTTGTCATTGCTCTGGCTGAATTAGTGAACCGATTATCT
 841 CATCCCCTTGAGTTGTCTATTTATTGCTCTGGCTAAGATATGCGTACGAATTTTGTATGCTGTA
 901 AGTCTTGAACGACTTGGTCTGTGTAATATTCGTCAATTTTATGGTTCAAGTGAATGTTGGCC
 961 GCTGATAGACTTGGTCTGTGTAATATTGTCAATATTTATGGTTCAAGTGAATGTTGGCC
1021 GTGGTGGGCAAGTGATGATGAATTGTACCAAGGGTAGTGTTGGTCACCAACGTGGT
1081 ATTATTGGTAAAGTTAAGGCCAACTATGTATGCTGAGACTACTAGTTACTACAATAATCAGAAGCATCC
1141 TTCTTGAAATTAAGGAATGAAGAAGATGTTAATACTGGTCATGCTGGATATTATATGAT
1201 AAGTGGTTAAGATGATTCGTTCTTGATAGATTAGACATTAAAGGATATTGTCTTCGATGTGTAGGT
1261 CGATTTGAATGGTTCGTTCTTGATAGATTAGACAGCATTGTATATCCGATATTGATGCTTGGT
1321 GTGGCACCAACTGTATTCGGATGTGAAATGGTTGAGGCGTGAGGCTGATGAAATTTGCATTCTTGACCAAACT
1381 GTTATTGGTATTCGGATGTGAAGGTGGTCATGTCATGTCATGTGATTTTCGTTGCCGAAAACTATCCCC
1441 AGAAAAGAACTCACTGAAAGACTGAAAAGATGTCATGTTTGTGATTTCGTTGCCGAAAACTACCCTATCCC
1501 AAACATCTCAAAGGTGGCTGTCAATTGTTGTTGAAGAAATTCCAAGAATCCAGCTGAAG
1561 ATGTTCGGTCGTATTTTAAGATCAACATTGTAA
```

FIG. 14

(SEQ ID NO: 10)

1 MTSTSVDNIVYGEKPKEDVLKEANSYGEYTFKRLRARGDEVSVIDGVTGEHTTASTIYAK
61 TVRTAECLQAYGIRKGDRIGICSDTMIEYYIVMGTMAVGAIICPVIISWTEADMNHAFN
121 ISCPTVFFVSKSILPTIAKLSKRNPYVKDIIVFDDESPEKPFISFKDFLANPKVPSKPHF
181 DCEPQDMESTIATVLCTSGTTGISKGVAISQYNLIHFMSLDTKNDKKGLFLCVAQYSNAE
241 GFTALMRRAFNGTRVIHLPKYEEKAYLECVQKYKVNYISVHPPLMLSLAKKPEIVNYDLS
301 SLERIYCSGTTVSVRILYAVADRLGVNYVRQFYGSSECLAVVAQSDEYCTKGSVGTLMPG
361 IIGKVVHPETGALLGPNQRGFLKEKANSIMYGYYNNPEASKVVKDEEGYVNTGDAGYYND
421 REEWFVVDRLKDIVMVDGVGVAPTEMEAVILLHPDIIDACVIGISDGEGGEILFAFLTKT
481 RKEITEKDVNDFVAEKLPYPKHLKGGCQFVEELPKNPAGKMLRRILRSTL*

```
       401          411        421        431        441        451        461        471
SEQ ID NO: 6) consensus  KVVKDEELATVNTGDAGYYNERFEWFVVDRLKDIVMVDGVAVAPFEMETILLUPDIDACVIGISDXGSGEVLPASITKT
SEQ ID NO: 2) A. rickettsii      ..................................................................
SEQ ID NO: 6) A. flava           .........................D.......G..............AV.............L...
SEQ ID NO: 8) A. germanus        ..................................................................
S

ARACHNOCAMPA LUCIFERASES

CROSS REFERENCE TO RELATED APPLICATIONS

This application claims priority to PCT Patent Application Number PCT/AU2006/001180 filed Aug. 18, 2006 and U.S. Provisional Patent Application No. 60/709,473 filed Aug. 19, 2005, which are both hereby incorporated by reference in their entirety.

BACKGROUND OF THE INVENTION

A. Field of the Invention

The present invention relates generally to luciferases. In particular, the invention relates to proteins and peptides of luciferase enzymes that are functional to catalyse ATP dependent luminescence reactions producing light emission spectra with maximum intensities in the blue portion of the spectrum and assays utilizing such luciferases. In a further aspect, the invention relates to luciferases isolated from organisms of the genus *Arachnocampa* (Diptera).

B. Description of Related Art

The use of reporter molecules or labels to qualitatively or quantitatively monitor molecular events is well established. They are found in assays for medical diagnosis, for the detection of toxins and other substances in industrial environments, and for basic and applied research in biology, biomedicine, and biochemistry. Such assays include immunoassays, nucleic acid probe hybridization assays, and assays in which a reporter enzyme or other protein is produced by expression under control of a particular promoter. Reporter molecules, or labels in such assay systems, have included radioactive isotopes, fluorescent agents, enzymes and chemiluminescent agents.

Included in assay systems employing chemiluminescence to monitor or measure events of interest are assays that measure the activity of a bioluminescent enzyme, luciferase.

Light-emitting systems have been known and isolated from many luminescent organisms including bacteria, protozoa, coelenterates, molluscs, fish, millipedes, flies, fungi, worms, crustaceans, and beetles, particularly click beetles of genus *Pyrophorus* and the fireflies of the genera *Photinus*, *Photuris*, and *Luciola*. Additional organisms displaying bioluminescence are listed in WO/2000/024878 and 1999/049019. Also see Viviani, V. R., (2002) Cell. Mol. Life Sci. 59:1833-1850, which lists properties of bioluminescent terrestrial arthropods and insects.

In many of these organisms, enzymes catalyze monooxygenation, utilizing the resulting free energy to excite a molecule to a high energy state. Visible light is emitted when the excited molecule spontaneously returns to the ground state. This emitted light is called "bioluminescence." Hereinafter it may also be referred to simply as "luminescence."

Since the earliest studies, beetle luciferases (particularly that from the common North American firefly species *Photinus pyralis*) have served as paradigms for understanding of bioluminescence. The fundamental knowledge and applications of luciferases have typically been based on a single enzyme, called "firefly luciferase," derived from *Photinus pyralis*. However, there are roughly 1800 species of luminous beetles worldwide. Thus, the luciferase of *Photinus pyralis* is a single example of a large and diverse group of beetle luciferases. It is known that all beetle luciferases catalyze a reaction of the same substrate, a polyheterocyclic organic acid (hereinafter referred to as "luciferin", unless otherwise indicated), which is converted to a high energy molecule. It is likely that the catalyzed reaction entails the same mechanism in each case.

Beetle luciferases, including the so-called firefly luciferases, are members of the adenylate-forming superfamily of enzymes. Beetle luciferases catalyse a multistep reaction that has some similarities to the reactions catalysed by other adenylate-forming enzymes such as the acyl-CoA ligases, various other CoA ligases (e.g. 4-coumarate-CoA ligase) and peptide synthetases.

The first step of the reaction is the addition of an adenine monophosphate (adenylation) to the carboxylic carbon of D-luciferin to form luciferyl-AMP. ATP is the source of the AMP and the other product of the reaction is pyrophosphate. Thus, this reaction is "ATP dependent" or "dependent upon ATP". Presumably hydrolysis of the pyrophosphate is used to drive the reaction forwards. Luciferyl-AMP is a mixed acid anhydride of acetic and phosphoric acids. It is relatively reactive because the adenylyl group is a good leaving group. In similar enzymes the first step is also adenylation of a carboxylate on the substrate molecule, whether it be acetate, a long-chain fatty acid, 4-coumarate, or an amino acid.

In the case of CoA utilising enzymes there is generally nucleophilic attack of the CoA sulphhydryl on the adenylated carboxylic acid resulting in conjugation of CoA to the substrate. In the case of beetle luciferases there is attack of molecular oxygen at the carbonyl, resulting in a highly energetic dioxetane intermediate, which subsequently decays releasing a photon, typically within the green-yellow portion of the spectrum (550-570 nm) plus carbon dioxide.

Luciferases possess features which render them particularly useful as reporter molecules for biosensing (using a reporter system to reveal properties of a biological system). Signal transduction in biosensors (sensors which comprise a biological component) generally involves a two step process: signal generation through a biological component, and signal transduction and amplification through an electrical component. Signal generation is typically achieved through binding or catalysis.

Conversion of these biochemical events into an electrical signal is typically based on electrochemical or caloric detection methods, which are limited by the free energy change of the biochemical reactions. For most reactions this is less than the energy of hydrolysis for two molecules of ATP, or about 70 kJ/mole. However, the luminescence elicited by luciferases carries a much higher energy content. Photons emitted from the reaction catalyzed by firefly luciferase (560 nm) have 214 Kj/einstein. Firefly luciferase converts chemical energy into light with high efficiency and extraordinary signal to noise characteristics. The quantum yield per molecule of D-luciferin is 0.88 (Seliger and McElroy 1960; Seliger and W. D 1960). This enzyme is therefore an extremely efficient transducer of chemical energy.

However, the known ATP dependent luciferases, e.g. the beetle luciferases, emit within a relatively narrow range of emission spectra. None of the known beetle luciferases emit with maximum emission intensities at wavelengths less than or equal to 530±5 nm (Viviani 2002; Nakatsu et al. 2006). Indeed, structural modifications to known luciferases permit lowering of the energy of emission spectrum (i.e. to maximum emission intensities at longer wavelengths), but not an increase in the energy of the emission spectrum (i.e. to shorter wavelengths). Further information on how structural modifications currently thought to modify emission spectrum may be found in Nakatsu et al. (2006).

Luciferases have been isolated directly from various sources and their cDNAs reported. See, for example: de Wet et al., Molec. Cell. Biol 7, 725-737 (1987); Masuda et al., Gene 77, 265-270 (1989); Nakatsu et al. (2006); and Wood et al., Science 244, 700-702 (1989)). With the cDNA encoding a luciferase in hand, it is entirely straightforward for the skilled to prepare large amounts of the luciferase by isolation from bacteria (e.g. *E. coli*), yeast, mammalian cells in culture, or the like, which have been transformed to express the cDNA. Alternatively, the cDNA, under control of an appropriate promoter and other signals for controlling expression, can be used in such a cell to provide luciferase (and ultimately bioluminescence catalyzed thereby) as a signal to indicate activity of the promoter. The activity of the promoter may, in turn, reflect another factor that is sought to be monitored, such as the concentration of a substance that induces or represses the activity of the promoter. Various cell-free systems that have recently become available to make proteins from nucleic acids encoding them, can also be used to make luciferases.

The ready availability of cDNAs encoding luciferases makes possible the use of the luciferases as reporters in assays employed to signal, monitor or measure genetic events associated with transcription and translation, by coupling expression of such a cDNA, and consequently production of the enzyme, to such genetic events.

For example, firefly luciferase has been widely used to detect promoter activity in eukaryotes and prokaryotes. Substrates required for the luminescence reaction, including a luciferin or other substrate, oxygen and ATP, are available or made readily available within living cells.

Multiple Reporter Assays

Mulitple, dual (or double) reporters are commonly used to improve experimental accuracy. The term "dual reporter" refers to the simultaneous expression and measurement of two individual reporter enzymes within a single system. The term "multiple reporter" refers to the simultaneous expression and measurement of two or more individual reporter enzymes within a single system. When used together, two or more individual reporter enzymes may be termed "co-reporters". Examples that currently benefit from multiple reporter assays include individual cells or cell populations (such as cells dispersed in culture, segregated tissues, or whole animals) genetically manipulated to simultaneously express two different reporter genes. Most frequently, the activity of one gene reports the impact of the specific experimental conditions, while the activity of a second reporter gene provides an internal control by which all sets of experimental values can be normalized. Normalizing the activity of the experimental reporter to the activity of the internal control minimizes experimental variability caused by, for example, differences in cell viability or transfection efficiency. Other sources of variability, such as differences in pipetting volumes, cell lysis efficiency and assay efficiency, can be effectively eliminated. Thus, dual reporter assays often allow more reliable interpretation of the experimental data by reducing extraneous influences.

Cell-free reconstituted systems that may benefit from dual-enzyme reporter technology are cellular lysates derived for the simultaneous translation, or coupled transcription and translation, of independent genetic materials encoding experimental and control reporter enzymes. Immuno-assays may, likewise, be designed for dual-reporting of both experimental and control values from within a single sample.

Currently, genes encoding firefly luciferases (luc), *Renilla* luciferases, chloramphenicol acetyl transferase (CAT), beta-galactosidase (lacZ), beta-glucuronidase (GUS) and various phosphatases such as secreted alkaline phosphatase (SEAP) and uteroferrin (Uf; an acid phosphatase) have been combined and used as co-reporters of genetic activity. The following references provide representative examples of these various reporter genes used in combined form for the purpose of dual-reporting of genetic activity: luc and GUS: Leckie, F., et al., 1994; luc and CAT, and luc and lacZ: Jain, V. K. and Magrath, I. T., 1992; CAT and lacZ: Flanagan, W. M., et al., 1991. See also Promega Dual-Luciferase™ Reporter Assay system, the Dual-Glo™ Luciferase Assay System, described in its Technical Manual: Instructions for use of Products E2920, E2940, and E2980, revised 1/06, Part Number TM058; and Wood, K. V., (1998) *The Chemistry of Bioluminescent Reporter Assays*, Promega Notes 65, page 14, as well as Promega pGL3 Luciferase Reporter Vectors (available from Promega Corporation, Madison, Wis.) as well as U.S. Pat. Nos. 5,744,320 and 5,670,356.

The performance of any multiple reporter assay is limited by the characteristics and compatability of the constituent enzyme chemistries, and the ability to correlate the results respective to each. Disparate enzyme requirements or assay conditions may dictate that co-reporters may not be employed in an integrated, single-assay mixture or single-tube format. Ideally, a multiple reporter system would comprise at least two enzyme assays with compatible requirements, such as chemistries, temperatures, handling requirements, speed, sensitivity, detection instrumentation, etc.

In an attempt to meet the ideal requirements of a multiple reporter system, clones of different luciferases, particularly of a single genus or species, may be utilized together in bioluminescent reporter systems. The ability to distinguish each of the luciferases in a mixture, however, is limited by the width of their emissions spectra. Measurable variations in luminescence color from luciferases is needed for systems which utilize two or more different luciferases as reporters.

One example of luminescence color variation occurs in *Pyrophorus plagiophthalamus*, a large click beetle indigenous to the Caribbean. See, e.g. United States Patent Application 20030166905 published 4 Sep. 2003. The beetle has two sets of light organs, a pair on the dorsal surface of the prothorax, and a single organ in a ventral cleft of the abdomen. Four different luciferase clones have been isolated from the ventral organ and have been named LucPplGR, LucPplYG, LucPplYE and LucPplOR. The luciferin-luciferase reactions catalyzed by these enzymes produces light that ranges from green to orange.

Spectral data from the luciferase-luciferin reaction catalyzed by these four luciferases show four overlapping peaks of nearly even spacing, emitting green (peak intensity: 546 nanometers), yellow-green (peak intensity: 560 nanometers), yellow (peak intensity: 578 nanometers) and orange (peak intensity: 593 nanometers) light. As used herein, peak intensity: 546 nanometers, for example, means that the maximum emission of a luminescence spectrum produced by a luminescence reaction catalyzed by a luciferase occurs at or about 546 nanometers. The term "about" in this context refers to normal limits of precision in the measurement of the wavelength at which peak, or maximum intensity occurs (also known as lambda-max). Normal limits of precision are, for example, plus or minus 5 nanometers (i.e. ±5 nm).

Unfortunately, though the wavelengths of peak intensity of the light emitted by these luciferases range over nearly 50 nm, there is still considerable overlap among the spectra, even those with peaks at 546 and 593 nm. Increasing the difference in wavelength of peak intensity among the luminescence reactions employed would thus be highly desirable to obtain greater measurement precision in systems using two or more luciferases. In particular, a novel luciferase that catalyzes a luminescence reaction producing a maximum intensity equal to or less than about 530 nm would be highly desirable. Peak intensities of or less than about 530 nm are within the blue portion of the spectrum.

In one attempt to meet this need, the blue-emitting luminescent system of the sea pansy, *Renilla reniformis*, has been exploited in dual reporter systems with firefly luciferase. The luminescence of sea pansy (*Renilla reniformis* and closely related species) is in the blue spectrum, which offers advantages over green-yellow luminescence in some applications. The chemistry of the *Renilla* light reaction is unrelated to that of beetles and the reactive intermediate is generated by a different pathway from beetle luciferases. Specifically, *Renilla* luciferases catalyses the oxidation of coelenterazine to coelenteramide with emission of blue light at 480 nm. A dioxetane intermediate may be involved but adenylation does not occur. *Renilla* luciferase is evolutionarily unrelated to beetle luciferases or adenylate-forming enzymes. See, for example, U.S. Pat. Nos. 5,292,658 and 5,418,155.

Advantages and Limitations of *Renilla* Luciferase

The main advantage of *Renilla* luciferase/coelenterazine system as a reporter of gene expression is that it luminesces in the blue spectrum using different substrates from beetle luciferin. *Renilla* luciferase may therefore be used in double-labelling experiments with beetle luciferase/luciferin. See, e.g. U.S. Pat. No. 5,744,320. Nevertheless, in other aspects *Renilla* luciferase is inferior to beetle luciferases because the coelenterazine substrate exhibits a low level of non-enzymatic luminescence. This level of autoluminescence varies according to the hydrophobicity of the environment and together these two phenomena significantly limit the absolute sensitivity of assays.

Beetle luciferase does not suffer from this deficiency, presumably because the oxidiseable substrate (luciferyl-AMP) is never found free in solution but is synthesised, as described above, while tightly bound by the luciferase and is consequently very short-lived, with oxidation also occurring on the enzyme.

Additional shortcomings of *Renilla* luciferase is that it cannot be directly used in applications that involve ATP quantification, because the reaction does not utilise ATP. Also, *Renilla* luciferase is not amenable to continuous dual label assays in the presence of active or unquenched beetle luciferase.

*Orfelia fultoni*

*Orfelia fultoni*, is a bioluminescent fly (Diptera) found in North America (Fulton, 1941). Its general biology is very similar to that of Australasian flies of the genus *Arachnocampa*, described in the next section. According to Viviani, Hasting et al. (Viviani, Hastings et al. 2002). *Orfelia* has a blue luminescence with lambda max=460 nm, a wavelength shorter than for any other insect-derived luminescence. Interestingly the *Orfelia* luminescence is not dependent on ATP, a feature that distinguishes it from the luminescence of all other insects, and is stimulated by some mild reducing agents. Viviani, Hastings et al. have partially characterised the luciferase of *Orfelia* biochemically (Viviani, Hastings et al. 2002).

*Arachnocampa*

The presence of blue-emitting glowworms in sheltered habitats throughout Eastern Australia must have been well-known to indigenous Australians for tens of thousands of years. Closely related species occur in spectacular concentrations in New Zealand. The glowworms, which use their blue luminescence to attract prey into a sticky web, are the larvae of keroplatid flies. However, the first European descriptions misidentifed them as the larvae of beetles related to the European glow-worm *Lampyris noctiluca* (Coleoptera, Lampyridae). Currently recognized species (Baker 2004; Harrison 1966; Pugsley 1983) of Australasian glow-worms (Diptera: Keroplatidae: Arachnocampinae) are listed, in part, in Table 1.

TABLE 2

| Name<br>Genus (subgenus) species (Authority) |
|---|
| *Arachnocampa* (*Campara*) *richardsae* (Harrison) |
| *Arachnocampa* (*Arachnocampa*) *tasmaniensis* (Ferguson) |
| *Arachnocampa* (*Campara*) *girraweenensis* (Baker) |
| *Arachnocampa* (*Campara*) *gippslandensis* (Baker) |
| *Arachnocampa* (*Campara*) *otwayensis* (Baker) |
| *Arachnocampa* (*Campara*) *tropicus* (Baker) |
| *Arachnocampa* (*Arachnocampa*) *buffaloensis* (Baker) |
| *Arachnocampa* (*Campara*) *flava* (Harrison) |
| *Arachnocampa* (*Arachnocampa*) *luminosa* (Skuse) |

According to (Shimomura, Johnson et al. 1966), the maximum of the *Arachnocampa* emission spectrum is 487±5 nm, which is in close agreement with the corrected emission spectrum presented by (Lee 1976) for *A. richardsae*. Viviani, Hastings et al. (2002) quote an emission maximum of 484 nm for *A. flava*. Lee (1976) also showed that the luminescence of *Arachnocampa* luciferase is stimulated by ATP and requires $Mg^{++}$. The short wavelength emission suggests that *Arachnocampa* luciferase substrate is different from beetle luciferin (Wood 1983) and, indeed, beetle D-luciferin has not yet been demonstrated to stimulate the *Arachnocampa* luciferase (Lee 1976; Wood 1983; Viviani, Hastings et al. 2002).

Wood (1983) showed that luminescence in depleted cold extracts of *Arachnocampa* light organs could be regenerated by the addition of a heat-treated extract. Viviani, Hastings et al. (Viviani, Hastings et al. 2002) were able to extract some *Arachnocampa* luciferin using acidic ethyl acetate and performed a partial separation using TLC. No structural information is available regarding native *Arachnocampa* luciferin. According to Viviani, Hastings et al. (2002) the *Arachnocampa* luciferase has a molecular weight, estimated by gel filtration, of 36 kDa, i.e. approximately half the molecular weight of firefly luciferase, which is 62 kDa (Conti, Franks et al. 1996).

SUMMARY OF THE INVENTION

In one aspect, the present invention provides an isolated peptide comprising an amino acid sequence selected from the group consisting of SEQ ID NO:2, SEQ ID NO: 6, SEQ ID NO: 8, and SEQ ID NO: 10. In additional aspects, the invention provides an isolated peptide comprising an amino acid sequence a variant of an amino acid sequence selected from the group consisting of SEQ ID NO:2, SEQ ID NO: 6, SEQ ID NO: 8, and SEQ ID NO: 10, wherein the variant is encoded by a nucleic acid molecule that hybridizes under stringent conditions to a nucleic acid molecule with a sequence selected from the group consisting of SEQ ID NO:1, SEQ ID NO: 3, SEQ ID NO: 5, SEQ ID NO: 7 and SEQ ID NO: 9 or a complement thereof.

In a further aspect, the invention provides an isolated peptide comprising an amino acid sequence of an ortholog of an amino acid sequence selected from the group consisting of SEQ ID NO:2, SEQ ID NO: 6, SEQ ID NO: 8, and SEQ ID NO: 10, wherein the ortholog is encoded by a nucleic acid molecule that hybridizes under stringent conditions to a nucleic acid molecule with a sequence selected from the group consisting of SEQ ID NO:1, SEQ ID NO: 3, SEQ ID NO: 5, SEQ ID NO: 7 and SEQ ID NO: 9 or a complement thereof.

In yet a further aspect, the invention provides an isolated peptide comprising an amino acid sequence comprising a fragment of an amino acid sequence of at least 10 contiguous amino acids selected from the group consisting of SEQ ID NO:2, SEQ ID NO: 6, SEQ ID NO: 8, and SEQ ID NO: 10. In particular embodiments, the invention includes an isolated peptide having an amino acid sequence that shares at least 70, 80, or 90 percent identity with an amino acid sequence selected from the group consisting of SEQ ID NO:2, SEQ ID NO: 6, SEQ ID NO: 8, and SEQ ID NO: 10. In some preferred embodiments, the isolated peptides of the invention have a molecular weight greater than 36 kiloDaltons (kD). These peptides may be termed "a peptide of the invention".

In especially preferred embodiments, the invention provides for enzymatically active portions of the peptides of the invention that are responsible for the catalysis of luminescence reactions with spectra displaying maximum emission at a wavelength less than or equal to 530±5 nm. In especially preferred embodiments, the luminescence reaction is dependent upon ATP.

As noted herein, ±5 nm reflects the typical precision with which such wavelengths may be specified. In particular, preferred embodiments luminescence reactions produce emission spectra with maximum emission intensities at wavelengths less than or equal to 520±5 nm, 510±5 nm, 500±5 nm, or 490±5 nm. These peptides displaying such luciferase activity may be termed "an active luciferase" or "a peptide of the invention displaying luciferase activity", "a functional luciferase", or "GW luciferase" of the invention.

In preferred embodiments, the invention provides an isolated peptide that displays luciferase activity, wherein the luciferase activity comprises catalysis of a luminescence reaction dependent upon ATP and the luminescence reaction produces an emission spectrum with a maximum emission intensity at wavelengths less than or equal to 530±5 nm. In one embodiment the peptide comprises a contiguous amino acid sequence having at least 70% sequence identity with amino acids 200 to 350 of a sequence selected from the group consisting of SEQ ID NO:2, SEQ ID NO: 6, SEQ ID NO: 8, and SEQ ID NO: 10.

In further specific embodiments, the invention provides an isolated peptide that displays luciferase activity, wherein the luciferase activity comprises catalysis of a luminescence reaction dependent upon ATP and the luminescence reaction produces an emission spectrum with a maximum emission intensity at wavelengths less than or equal to 530 nm and wherein the isolated peptide has an amino acid sequence that, when aligned with a *Photinus* luciferase, e.g. SEQ ID NO: 4, differs from that of SEQ ID NO: 4 by at least one change in amino acid sequence selected from the group consisting of deletion of R218, H245N, G315S, L342S, and T343S. In yet further embodiments, such a peptide has an amino acid sequence that, when aligned with that of SEQ ID NO: 4, differs from that of SEQ ID NO: 4 by at least one change in amino acid sequence selected from the group consisting of A22Y, Y53A, L63T, E83D, F88Y, F89Y, P91I, A103C, Y109W, E113D, V139I, G160P, S198T, H212Q, a deletion of R218, D224S, a deletion of P225, G228D, P233K, P242Q, F243Y, H245N, L253M, Y255R, F273Y, Y280F, S298K, L300E, E311R, G315S, P318T, L319V, G339F, L342S, T343S, D375H, K380A, E389F, T408S, W417Y, L418V, D427N, L441I, I442V, K443M, Y444V, K445D, Q448A, A452T, L458I, V485L, V486T, G490R, V506L, R513K, V516C, T527A, and a deletion of all residues from and including K549 to the carboxy terminus. Peptides of the invention include those based upon the sequence of SEQ ID NO: 4 but embodying one or more changes of amino acid sequence as listed above or as listed in Table 5 and in the detailed description that follows.

In additional, preferred embodiments, the isolated peptides of the invention that display luciferase activity have amino acid sequences that share at least 70 percent identity with an amino acid sequence selected from the group consisting of SEQ ID NO:2, SEQ ID NO: 6, SEQ ID NO: 8, and SEQ ID NO: 10.

In particular embodiments the active luciferase peptide comprises an amino acid sequence selected from the group consisting of SEQ ID NO:2, SEQ ID NO: 6, SEQ ID NO: 8, and SEQ ID NO: 10. In additional aspects, the invention provides an active luciferase peptide comprising an amino acid sequence a variant of an amino acid sequence selected from the group consisting of SEQ ID NO:2, SEQ ID NO: 6, SEQ ID NO: 8, and SEQ ID NO: 10, wherein the variant is encoded by a nucleic acid molecule that hybridizes under stringent conditions to a nucleic acid molecule with a sequence selected from the group consisting of SEQ ID NO:1, SEQ ID NO: 3, SEQ ID NO: 5, SEQ ID NO: 7 and SEQ ID NO: 9 or a complement thereof.

In a further aspect, the invention provides an active luciferase peptide comprising an amino acid sequence of an ortholog of an amino acid sequence selected from the group consisting of SEQ ID NO:2, SEQ ID NO: 6, SEQ ID NO: 8, and SEQ ID NO: 10, wherein the ortholog is encoded by a nucleic acid molecule that hybridizes under stringent conditions to a nucleic acid molecule with a sequence selected from the group consisting of SEQ ID NO:1, SEQ ID NO: 3, SEQ ID NO: 5, SEQ ID NO: 7 and SEQ ID NO: 9 or a complement thereof.

In yet a further aspect, the invention provides an active luciferase peptide comprising an amino acid sequence comprising a fragment of an amino acid sequence of at least 10 contiguous amino acids selected from the group consisting of SEQ ID NO:2, SEQ ID NO: 6, SEQ ID NO: 8, and SEQ ID NO: 10. In particular embodiments, the invention includes an active luciferase peptide having an amino acid sequence that shares at least 70, 80, or 90 percent identity with an amino acid sequence selected from the group consisting of SEQ ID NO:2, SEQ ID NO: 6, SEQ ID NO: 8, and SEQ ID NO: 10. In some preferred embodiments the active peptides of the invention displaying luciferase activity have molecular weights greater than 36 kiloDaltons.

Additional aspects of the invention include antibodies that selectively bind to a peptide of the invention. In preferred embodiments, such antibodies find use in the detection of the presence of the peptides of the invention selected from the group consisting of: (a) an amino acid sequence shown in SEQ ID NO:2; (b) an amino acid sequence a variant of an amino acid sequence shown in SEQ ID NO:2, wherein the variant is encoded by a nucleic acid molecule that hybridizes under stringent conditions to a nucleic acid molecule shown in SEQ ID NO:1 or its complement; (c) an amino acid sequence of an ortholog of an amino acid sequence shown in SEQ ID NO:2, wherein the ortholog is encoded by a nucleic acid molecule that hybridizes under stringent conditions to a nucleic acid molecule shown in SEQ ID NO:1 or its complement; and (d) a fragment of an amino acid sequence shown in SEQ ID NO:2, wherein the fragment comprises at least 10 contiguous amino acids.

The invention further encompasses an isolated nucleic acid molecule comprising a nucleotide sequence that encodes an amino acid sequence selected from the group consisting of SEQ ID NO:2, SEQ ID NO: 6, SEQ ID NO: 8, and SEQ ID NO: 10. The invention likewise includes a nucleotide sequence that encodes a variant of an amino acid sequence selected from the group consisting of SEQ ID NO:2, SEQ ID NO: 6, SEQ ID NO: 8, and SEQ ID NO: 10, wherein the nucleotide sequence hybridizes under stringent conditions to a nucleic acid molecule selected from the group consisting of SEQ ID NO:1, SEQ ID NO: 3, SEQ ID NO: 5, SEQ ID NO: 7 and SEQ ID NO: 9 or a complement thereof. Further, the invention includes a nucleotide sequence that encodes an ortholog of an amino acid sequence selected from the group consisting of SEQ ID NO:2, SEQ ID NO: 6, SEQ ID NO: 8, and SEQ ID NO: 10, wherein the nucleotide sequence hybridizes under stringent conditions to a nucleic acid molecule selected from the group consisting of SEQ ID NO:1, SEQ ID NO: 3, SEQ ID NO: 5, SEQ ID NO: 7 and SEQ ID NO: 9 or a complement thereof. Still further, the invention includes a nucleotide sequence that encodes a fragment of at least 10 contiguous amino acids of an amino acid sequence selected from the group consisting of SEQ ID NO:2, SEQ ID NO: 6, SEQ ID NO: 8, and SEQ ID NO: 10 and a nucleotide sequence that is the complement of the nucleotide sequence.

Nucleic acid molecules as described within the compass of the invention may be referred to as a "nucleic acid molecule of the invention". The invention includes a nucleotide sequence that is the complement of a nucleic acid molecule of the invention.

In various other embodiments, the invention further comprises a nucleic acid molecule of the invention included within a gene chip, a transgenic cell, a nucleic acid vector, or a host cell.

The methods of the invention include a method of detecting the presence of a nucleic acid molecule of the invention in a sample. Thus, in a particular embodiment the method comprises contacting the sample with an oligonucleotide that hybridizes to a nucleic acid molecule of the invention under stringent conditions and determining whether the oligonucleotide binds to the nucleic acid molecule in the sample.

Additional methods of the invention include, for example, a method of monitoring expression of a gene of interest or a portion thereof in a host cell, comprising: (a) introducing into the host cell a vector construct, the vector construct comprising a nucleic acid molecule of the invention, and further comprising a nucleic acid molecule encoding a nucleotide sequence or product of interest; wherein the nucleic acid molecule of the invention and the sequence or product of interest are co-expressed; and (b) detecting the presence of the expression of the nucleic acid molecule of the invention, thereby monitoring expression of the sequence or product of interest.

In particular methods of the invention, the nucleic acid molecule of the invention encodes a peptide displaying luciferase activity. Therefore, in preferred methods of the invention, detecting the presence of the expression of the nucleic acid molecule of the invention comprises assaying for luciferase activity. In specifically preferred methods, the luciferase activity includes catalysis of a luminescence reaction dependent upon ATP and the luminescence reaction produces an emission spectrum with a maximum emission intensity at wavelengths less than or equal to 530±5 nm.

In additional embodiments within the scope of the invention, an expression vector comprises the nucleotide sequence of the invention in operative linkage with a promoter. In particular embodiments, the promoter is functional in a cell selected from the group consisting of a plant cell, a bacterial cell, an animal cell and an insect cell. In yet further embodiments, the vector further comprises a nucleotide sequence encoding an additional sequence or product of interest. The additional sequence or product of interest can be a nucleic acid, a protein, an active luciferase or an enzymatically active portion thereof. Of course, in additional embodiments, the invention includes a host cell containing a vector of the invention. The host cell can be any suitable cell. In particular embodiments, the host cell is selected from the group consisting of a plant cell, an insect cell, a fungal cell, an animal cell and a bacterial cell.

In yet further aspects, the methods of the invention include a method of transforming or transfecting a host cell with a nucleic acid of interest or portion thereof, comprising: (a) introducing into the host cell a vector construct, the vector construct comprising a nucleic acid molecule of the invention that encodes a peptide displaying luciferase activity, wherein the peptide displaying luciferase activity is expressed; and (b) detecting the luciferase activity, thereby establishing that the host cell is transformed or transfected.

In further embodiments, the methods of the invention include a method of monitoring activity of a controller element in a host cell comprising: (a) introducing into the host cell a vector construct, the vector construct comprising a nucleic acid molecule of the invention and in operative linkage with the controller element; and (b) detecting the presence of the luciferase, thereby monitoring activity of the controller element. The controller element in this embodiment can be a promoter or an enhancer. The nucleic acid molecule of the invention can encode a peptide displaying luciferase activity. In such embodiments wherein the peptide displays luciferase activity, the detecting the presence of the luciferase can be by assay for luciferase activity.

Additional methods of the invention include a method of identifying a compound as a putative substrate of a functional luciferase, comprising: (a) contacting a functional luciferase encoded by a nucleic acid molecule of the invention with at least one candidate compound under conditions suitable for functional luciferase activity; and (b) assaying for luciferase activity, wherein detection of luciferase activity indicates that the at least one candidate compound is a putative substrate of a functional luciferase. Novel compounds identified by operation of the methods of the invention are expressly included within the scope of the invention.

Particularly preferred methods of the invention include a method of measuring the activity of at least two reporter enzymes in an aliquot of a sample comprising assaying for activity of a first reporter enzyme by measuring the light signal produced by catalysis of a luminescence reaction by the first reporter enzyme, and assaying for activity of at least a second reporter enzyme by measuring the light signal produced by catalysis of a luminescence reaction by at least a second reporter enzyme. Methods include those in which the assays are performed on the same aliquot of sample. In such embodiments, the assays may proceed in any order, grouping, or time sequence desired or convention. In particular embodiments, the assays proceed simultaneously. In additional, particular embodiments, at least one assay is performed prior to at least a second assay, or at least one assay is performed subsequent to all other assays, or the assays are performed sequentially. In particular embodiments, the first reporter enzyme comprises an active luciferase of the invention. Of course, in especially preferred embodiments, at least one of the reporter enzymes is a peptide that displays luciferase activity wherein the luciferase activity comprises catalysis of a luminescence reaction dependent upon ATP and the luminescence reaction produces an emission spectrum with a maximum emission intensity at wavelengths less than or equal to 530±5 nm.

In yet further embodiments, at least two reporter enzymes are ATP dependent luciferases. In especially preferred embodiments the first reporter enzyme is *Arachnocampa* luciferase and the second reporter enzyme is a different luciferase. By "different luciferase" is meant any other luciferase, whether ATP dependent or not. Particularly preferred different luciferases include those of the fireflies, click-beetles, or railroad worms. Additional preferred luciferases catalyze luminescence reactions that produce emission spectra with maximum emission intensities at wavelengths greater than 530 nm.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the invention presented herein.

FIG. 1A Consensus nucleotide sequence of *Arachnocampa richardsae* luciferase (SEQ ID NO: 1).

FIG. 1B Consensus nucleotide sequence of *Arachnocampa richardsae* luciferase (SEQ ID NO: 1) continued from FIG. 1A.

FIG. 2A Nucleic acid sequence and corresponding amino acid sequence of *Arachnocampa richardsae* luciferase.

FIG. 2B Nucleic acid sequence and corresponding amino acid sequence of *Arachnocampa richardsae* luciferase continued from FIG. 2A.

FIG. 3 Consensus amino acid sequence of *Arachnocampa richardsae* luciferase (SEQ ID NO: 2).

FIG. 4 Nucleic acid sequence of a luciferase of the invention (SEQ ID NO: 3).

FIG. 5A Nucleic acid sequence and corresponding amino acid sequence of a luciferase peptide of the invention.

FIG. 5B Nucleic acid sequence and corresponding amino acid sequence of a luciferase peptide of the invention continued from FIG. 5A.

FIG. 5C Nucleic acid sequence and corresponding amino acid sequence of a luciferase peptide of the invention continued from FIG. 5B.

FIG. 6E Alignment of luciferase amino acid sequences from 18 species of luminescent beetles and *Arachnocampa richardsae* luciferase continued from FIG. 6D.

FIG. 9 Native amino acid sequence of luciferase from the firefly, *Photinus pyralis* (FF luciferase; SEQ ID NO: 4).

FIG. 10 Nucleic acid sequence encoding *A. flava* luciferase (SEQ ID NO: 5)

FIG. 11 Amino acid sequence of *A. flava* luciferase (SEQ ID NO: 6).

FIG. 12 Nucleic acid sequence encoding *A. girraweenensis* luciferase (SEQ ID NO: 7)

FIG. 13 Amino acid sequence of *A. girraweenensis* luciferase (SEQ ID NO: 8).

FIG. 14 Nucleic acid sequence encoding *A. tasmaniensis* luciferase (SEQ ID NO: 9)

FIG. 15 Amino acid sequence of *A. tasmaniensis* luciferase (SEQ ID NO: 10).

FIG. 25A Multiple sequence alignment of four *Arachnocampa* luciferase peptides.

FIG. 25B Alignment of FIG. 25A continued.

DETAILED DESCRIPTION OF THE INVENTION

Figure 6A:
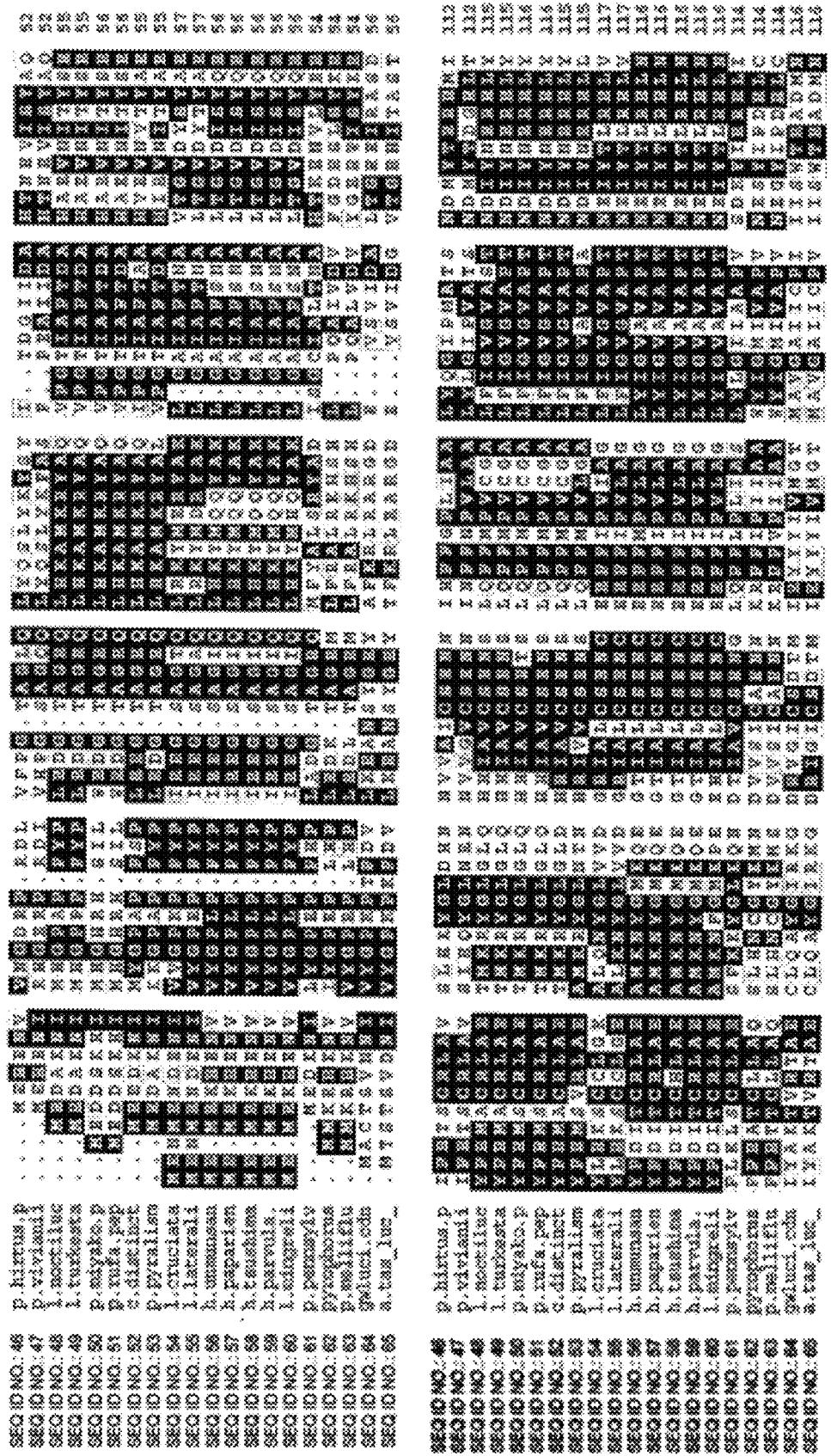
FIG. 6A Alignment of luciferase amino acid sequences from 18 species of luminescent beetles and *Arachnocampa richardsae* luciferase.
Figure 6B:
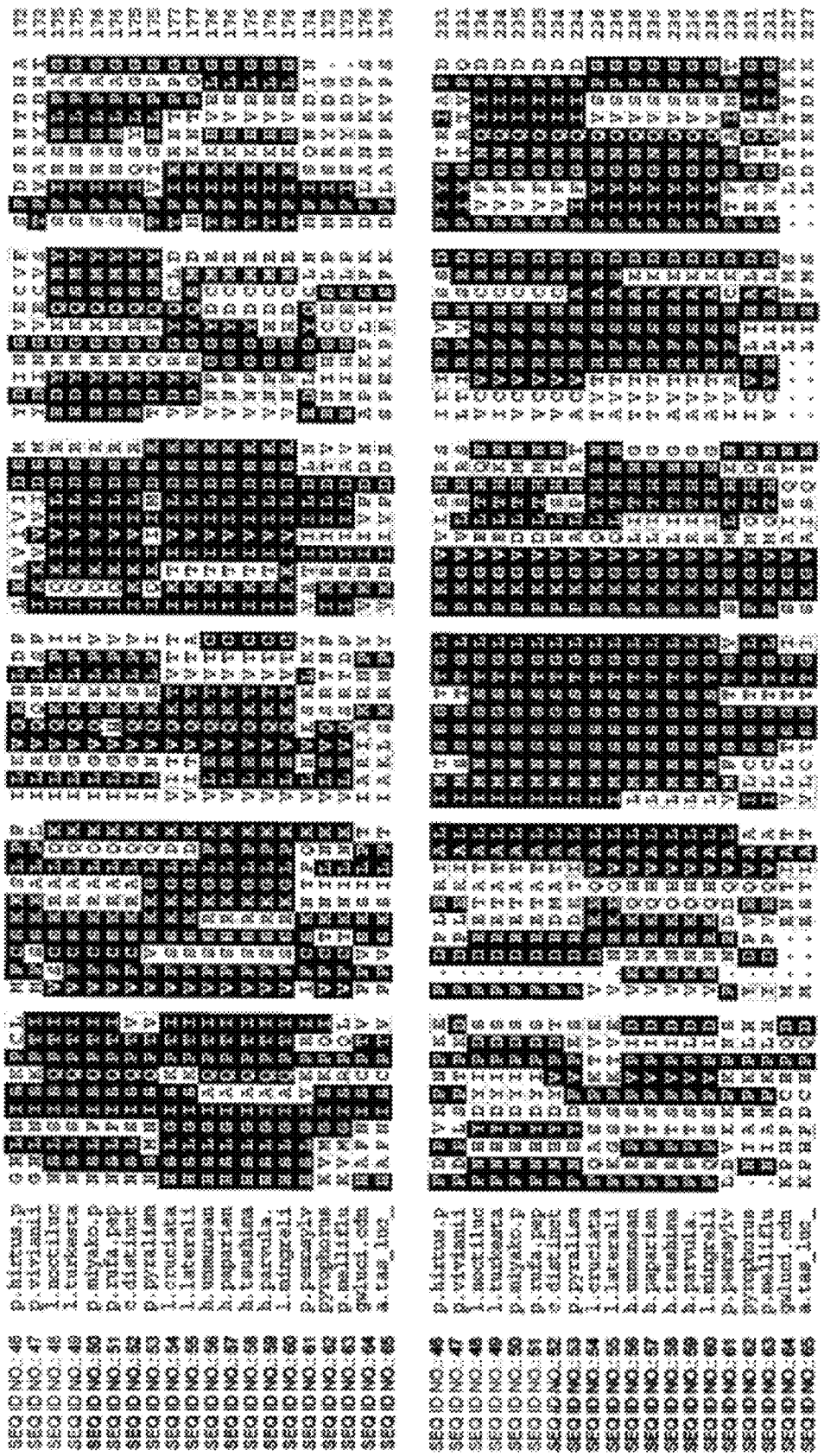
FIG. 6B Alignment of luciferase amino acid sequences from 18 species of luminescent beetles and *Arachnocampa richardsae* luciferase continued from FIG. 6A.
Figure 6C:
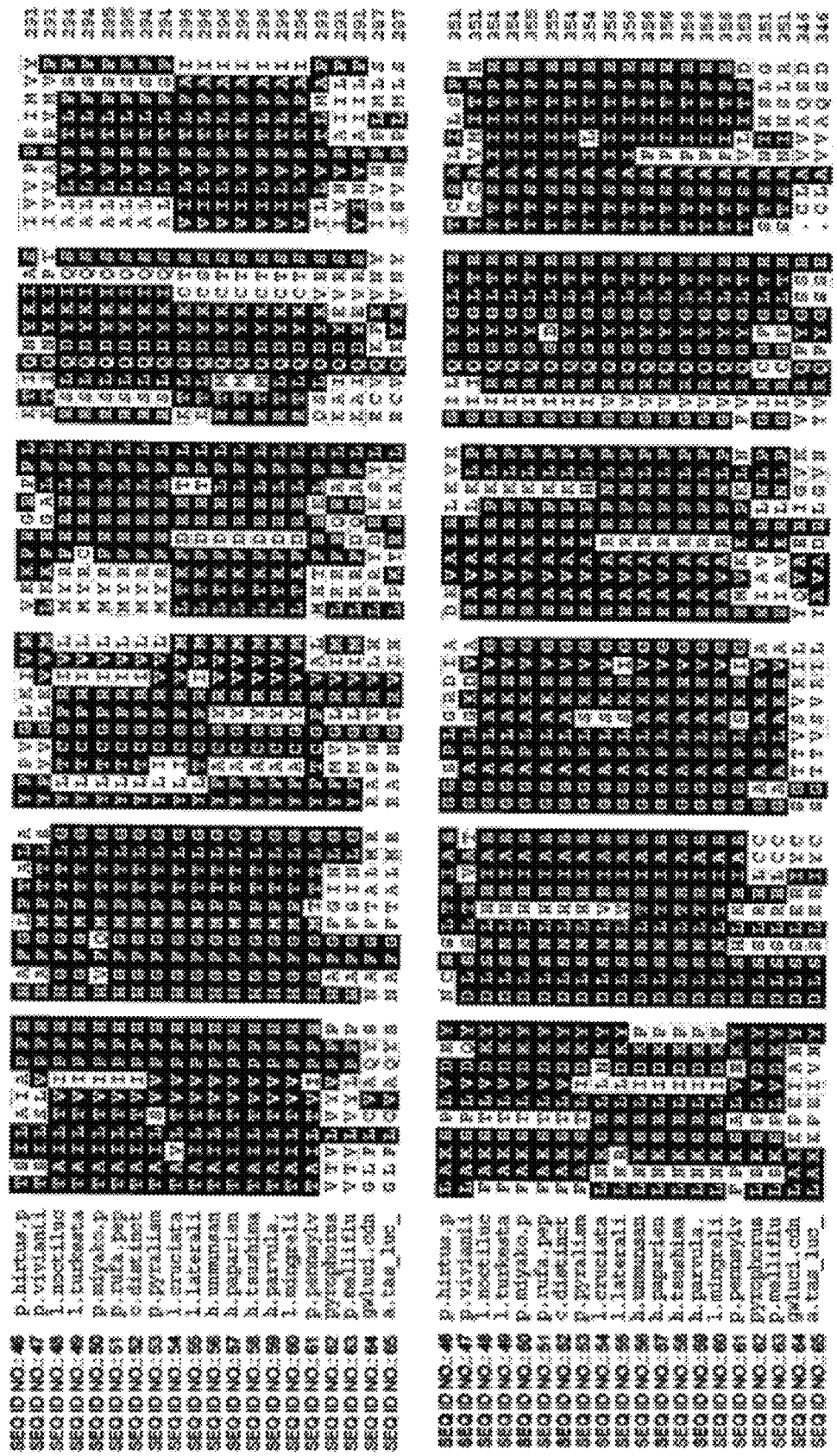
FIG. 6C Alignment of luciferase amino acid sequences from 18 species of luminescent beetles and *Arachnocampa richardsae* luciferase continued from FIG. 6B.
Figure 6D:
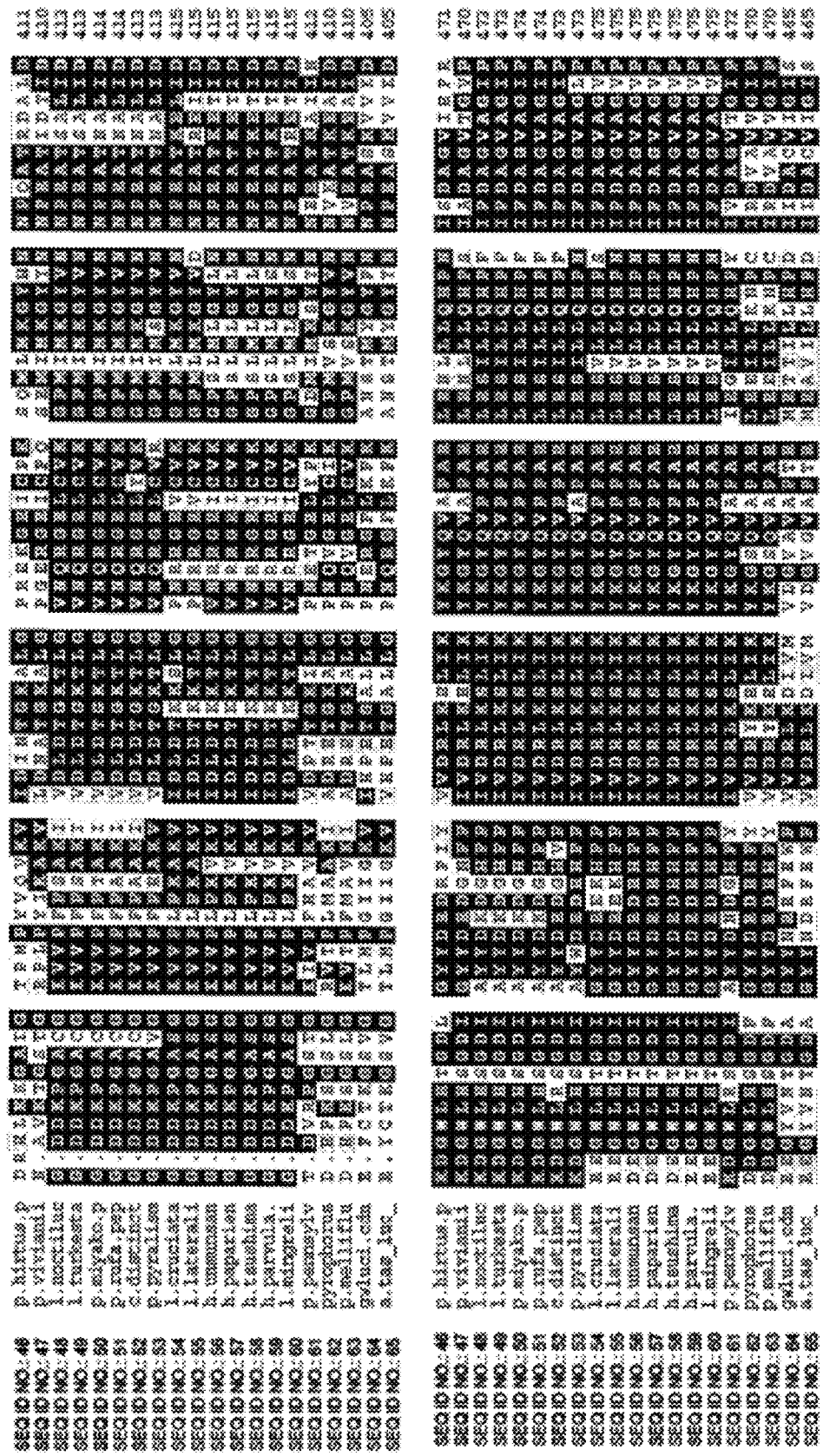
FIG. 6D Alignment of luciferase amino acid sequences from 18 species of luminescent beetles and *Arachnocampa richardsae* luciferase continued from FIG. 6C.

The following detailed descriptions of particular embodiments and examples are offered by way of illustration and not by way of limitation. Unless contraindicated or noted otherwise, in these descriptions and throughout this specification, the terms "a" and "an" mean one or more. Similarly the term "or" means "and/or".

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range.

Peptide Molecules

The present invention provides nucleotide sequences that encode peptide molecules that have been identified as being members of the luciferase enzyme family of proteins. The peptide sequences provided, as well as the obvious variants described herein, particularly congeneric variants as identified herein and using the information provided herein, will be referred to as the enzymes, enzyme peptides, peptides, or proteins of the present invention.

The present invention in one aspect provides isolated peptide and protein molecules that consist of, or consist essentially of, or comprise the amino acid sequences of the enzyme peptides disclosed in FIGS. 2, 3, 5, 11, 13, 15 or SEQ ID NO:s 2, 6, 8, and 10 or encoded by the nucleic acid molecules shown in FIGS. 1, 2, 4, 5, 10, 12, 14 or SEQ ID NO:s 1, 3, 11, 13, and 15 as well as all obvious variants of these that are within the art to make and use. Some of these variants are described in detail below.

As used herein, a peptide is said to be "isolated" or "purified" when it is substantially free of cellular material or free of chemical precursors or other chemicals. The peptides of the present invention may be purified to homogeneity or other degrees of purity. The level of purification will be based on the intended use. (Features of an isolated nucleic acid molecule are discussed below).

In some uses, "substantially free of cellular material" includes preparations of the peptide having less than about 30% (by dry weight) of other proteins (i.e., contaminating protein), less than about 20% other proteins, less than about 10% other proteins, or less than about 5% other proteins. When the peptide is recombinantly produced, it may also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated enzyme peptide may be purified from cells that naturally express it, purified from cells that have been altered to express it (recombinant), or synthesized using known protein synthesis methods. For example, a nucleic acid molecule encoding the enzyme peptide is cloned into an expression vector, the expression vector introduced into a host cell and the protein expressed in the host cell. The protein may then be isolated from the cells by an appropriate purification scheme using standard protein purification techniques. Many of these techniques are described in detail below.

In one aspect, the present invention provides proteins that consists of the amino acid sequences provided. A protein consists of an amino acid sequence when the amino acid sequence is the final amino acid sequence of the protein.

In an additional aspect, the present invention further provides proteins that consist essentially of the amino acid sequences provided. A protein consists essentially of an amino acid sequence when such an amino acid sequence is present with only a few additional amino acid residues, for example from about 1 to about 100 or so additional residues, typically from 1 to about 20 additional residues in the final protein.

In yet a further aspect, the present invention provides proteins that comprise the amino acid sequences provided. A protein comprises an amino acid sequence when the amino acid sequence is at least part of the final amino acid sequence of the protein. In such a fashion, the protein may be only the peptide or have additional amino acid molecules, such as amino acid residues (contiguous encoded sequence) that are naturally associated with it or heterologous amino acid residues or peptide sequences. Such a protein may have a few additional amino acid residues or may comprise several hundred or more additional amino acids. A brief description of how various types of these proteins may be made or isolated is provided below.

The enzyme peptides of the present invention may be attached to heterologous sequences to form chimeric or fusion proteins. Such chimeric and fusion proteins may comprise an enzyme peptide operatively linked to a heterologous protein having an amino acid sequence not substantially homologous to the enzyme peptide. "Operatively linked-" indicates that the enzyme peptide and the heterologous protein are fused such that the operability of each is not destroyed. The heterologous protein may be fused to the N-terminus or C-terminus of the enzyme peptide.

In some uses, the fusion protein does not affect the activity of the enzyme peptide per se. For example, the fusion protein may include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, may facilitate the purification of recombinant enzyme peptide. In certain host cells (e.g., mammalian host cells), expression or secretion of a protein may be increased by using a heterologous signal sequence.

In some uses, the fusion protein may be a component of a protein compelementation assay, or PCA, wherein an active enzyme is divided into two domains, each fused or attached to interactor domains that are brought together by attraction to a third molecule such that the activity of the original enzyme is restored. See, for example, U.S. Pat. Nos. 6,270,964 and 6,342,345.

A chimeric or fusion protein may be produced by standard recombinant DNA techniques. For example, DNA fragments coding for the different protein sequences are ligated together in-frame in accordance with conventional techniques. In another embodiment, the fusion gene may be synthesized by conventional techniques including automated DNA synthesizers. Alternatively, PCR amplification or ligation of gene fragments may be carried out using anchor primers which give rise to complementary overhangs between two consecutive gene fragments which may subsequently be annealed and re-amplified to generate a chimeric gene sequence (see Ausubel et al., Current Protocols in Molecular Biology, 1998). Moreover, many expression vectors are commercially available that already encode a fusion moiety (e.g., a GST protein). An enzyme peptide-encoding nucleic acid may be cloned into such an expression vector such that the fusion moiety is linked in-frame to the enzyme peptide, which is one means by which the fusion protein is made without destroying the operability of each component.

As mentioned above, the present invention also provides and enables obvious variants of the amino acid sequence of the proteins of the present invention, such as naturally occurring mature forms of the peptide, allelic or sequence variants of the peptides, non-naturally occurring recombinantly derived variants of the peptides, and orthologs and paralogs of the peptides. Orthologs and analogs of the present peptides that may be isolated from the genus *Arachnocampa* (Diptera) as understood by those of skill in the art are preferred embodiments of the peptides of the invention. Such variants may readily be generated using art-known techniques in the fields of recombinant nucleic acid technology and protein biochemistry. It is understood, however, that variants exclude any complete amino acid sequences disclosed prior to the invention.

Such variants may readily be identified or made using molecular techniques and the sequence information disclosed herein. Further, such variants may readily be distinguished from other peptides based on sequence or structural homology to the enzyme peptides of the present invention. The degree of identity present will be based primarily on whether the peptide is a functional variant or non-functional variant, the amount of divergence present in the paralog family and the evolutionary distance between the orthologs.

To determine the percent identity of two amino acid sequences or two nucleotide sequences, the sequences are aligned for optimal comparison purposes (e.g., gaps may be introduced in one or both of a first and a second amino acid or nucleotide sequence for optimal alignment and non-homologous sequences may be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity"is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

Variants preferably have at least 60% sequence identity with the amino acid sequence set out in FIGS. 2, 3 or 5 or in SEQ ID NO: 2, more preferably at least 70, 80, 90, 95, 98 or 99% sequence identity with the amino acid sequence set out in FIGS. 2, 3 or 5 or in SEQ ID NO: 2.

Alternatively, as mentioned above, the sequence identity can be calculated in relation to particular regions of the peptide, for example the luciferin binding pocket. A sequence comparison of the amino acid sequence of *Arachnocampa* spp luciferase set out in SEQ ID NO: 2 and that of *Photinus pyralis*, a representative member of the beetle luciferases, shows that the sequence identity over the luciferin binding pocket region, which is located at approximately amino acids 201 to 350 of SEQ ID NO: 2, is about 28% whereas sequence identity over the C-terminal region, amino acids 351 to 530 of SEQ ID NO: 2, is about 41% (Table 6). The sequence identity over the N-terminal amino acids 1 to 200 is about 29%. Accordingly, a peptide of the invention preferably comprises a contiguous amino acid sequence having at least 50% sequence identity with amino acids 201 to 350 of SEQ ID NO: 2, more preferably at least 60, 70, 80, 90, 95, 98 or 99% sequence identity with amino acids 201 to 350 of SEQ ID NO: 2. Alternatively, or in addition, a peptide of the invention preferably comprises a contiguous amino acid sequence having at least 50% sequence identity with amino acids 351 to 530 of SEQ ID NO: 2, more preferably at least 60, 70, 80, 90, 95, 98 or 99% sequence identity with amino acids 351 to 530 of SEQ ID NO: 2. A peptide of the invention may also comprise a contiguous amino acid sequence having at least 50% sequence identity with amino acids 1 to 201 of SEQ ID NO: 2, more preferably at least 60, 70, 80, 90, 95, 98 or 99% sequence identity with amino acids 201 to 350 of SEQ ID NO: 2.

A comparison of the luciferase amino acid sequences from 18 lumiscent beetles identifies 128 residues that are completely conserved. When the corresponding residues of *Arachnocampa* species are compared, 55 of those residues differ (plus 3 deletions). The 55 residues that differ in *A. richardsae* are set out in Table 5. Preferred peptides comprise an amino acid sequence comprising amino acid residues corresponding to the 55 amino acid residues set out in Table 5, namely Y26, A54, T64, D84, Y89, Y90, I92, C104, W110, D114, I140, P161, T197, Q211, S219, D221, K226, Q235, Y236, N238, M246, R248, Y266, F273, K291, E293, R304, S308, T311, V312, F332, S335, S336, H367, A372, F381, S400, Y409, V410, N419, I433, V434, M435, V436, D437, A440, T444, I450, L477, T478, R481, L497, K504, C507, A518. Other preferred peptides comprise comprise an amino acid sequence comprising amino acid residues corresponding to the amino acid residues set out in Table 5 which lie within the luciferin binding pocket at from approximately amino acids 201 to 350, namely Q211, S219, D221, K226, Q235, Y236, N238, M246, R248, Y266, F273, K291, E293, R304, S308, T311, V312, F332, S335, S336.

The comparison of sequences and determination of percent identity and similarity between two sequences may be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In preferred embodiments, multiple sequence aligments and phylogenetic trees are derived using the PROTML or PROTPARS programs: PROTML (Adachi, J. and Hasegawa, M. 1996: Molphy Version 2.3. Programs for molecular Phylogenetics based on maximum likelihod. Computer Science monographs No. 28. A publication of the Institute of Statistical Mathematics, Tokyo)); and PROTPARS (Felsenstein, J. 1989. PHYLIP—Phylogeny Inference Package (Version 3.2). Cladistics 5: 164-166).

Pariwise alignments and levels of sequence identity and homology are determined using the BestFit program in the GCG software package. The percent identity between two amino acid sequences may be determined using the algorithm of Needleman and Wunsch (J. Mol. Biol. 48:444-453 (1970)), which has been incorporated into the GAP program in the GCG software package. The algorithm is employed using either a Blossom 62 matrix or a PAM250 matrix, and a gap weight of 16, 14, 12, 10, 8, 6, or 4 and a length weight of 1, 2, 3, 4, 5, or 6. The percent identity between two nucleotide sequences may be determined using the GAP program (Devereux, J., et al., Nucleic Acids Res. 12(1):387 (1984)) with a NSWgapdna.CMP matrix and a gap weight of 40, 50, 60, 70, or 80 and a length weight of 1, 2, 3, 4, 5, or 6.

The nucleic acid and protein sequences of the present invention may further be used as a "query sequence" to perform a search against sequence databases to, for example, identify other family members or related sequences. Such searches may be performed using the NBLAST and XBLAST programs (version 2.0) of Altschul, et al. (J. Mol. Biol. 215:403-10 (1990)). BLAST nucleotide searches may be performed with the NBLAST program, score=100, wordlength=12 to obtain nucleotide sequences homologous to the nucleic acid molecules of the invention. BLAST protein searches may be performed with the XBLAST program, score=50, wordlength=3 to obtain amino acid sequences homologous to the proteins of the invention. To obtain gapped alignments for comparison purposes, Gapped BLAST may be utilized as described in Altschul et al. (Nucleic Acids Res. 25(17):3389-3402 (1997)). When utilizing BLAST and gapped BLAST programs, the default parameters of the respective programs (e.g., XBLAST and NBLAST) may be used.

Full-length pre-processed forms, as well as mature processed forms, of proteins that comprise one of the peptides of the present invention may readily be identified as having complete sequence identity to one of the enzyme peptides of the present invention as well as being encoded by a nucleic acid that encodes the enzyme peptide provided herein.

Allelic variants of an enzyme peptide may readily be identified as being an *Arachnocampa* luciferase peptide having a high degree sequence identity to at least a portion of the enzyme peptides disclosed herein. As used herein, two proteins (or a region of the proteins) have a high degree sequence identity when the amino acid sequences are typically at least about 70-80%, 80-90%, and most highly at least about 90-95% or more homologous. A significantly homologous amino acid sequence, according to the present invention, will be encoded by a nucleotide sequence that will hybridize to a nucleic acid molecule encoding an *Arachnocampa* luciferase peptide under stringent conditions as more fully described below.

Orthologs of an enzyme peptide may readily be identified as having some degree of significant sequence identity to at least a portion of the enzyme peptide as well as being encoded by a gene from another organism. Preferred orthologs will be isolated from organisms classified as members of the genus *Arachnocampa* (Diptera). Such orthologs will be encoded by a nucleotide sequence that will hybridize to a novel nucleic acid molecule herein disclosed under moderate to stringent conditions, as more fully described below, depending on the degree of relatedness of the two organisms yielding the proteins.

Non-naturally occurring variants of the enzyme peptides of the present invention may readily be generated using recombinant techniques. Such variants include, but are not limited to deletions, additions and substitutions in the amino acid sequence of the enzyme peptide. For example, one class of substitutions are conserved amino acid substitution. Such substitutions are those that substitute a given amino acid in an enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247:1306-1310 (1990).

Variant enzyme peptides may be unaltered in all functions in comparison to that of a functional peptide, for example that of SEQ ID NO:2, or may consist of an altered function or even lack of function in one or more activities, e.g. ability to bind substrate, or shift in the emission spectrum. Functional variants may contain only conservative variation or variation in non-critical residues or in non-critical regions. FIG. 6, Tables 3 and 5, and further details herein may be used to identify critical domains/regions. Functional variants may also contain substitution of similar amino acids that result in no change or an insignificant change in function.

In one embodiment, the variants have luciferase activity, which luciferase activity comprises catalysis of a luminescence reaction dependent on ATP, the luminescence reaction generates an emission spectrum with a maximum emission intensity at wavelengths less than or equal to 530 nm. Preferably the variants have at least 25% of the luciferase activity of the luciferase of SEQ ID NO: 2, more preferably at least 40, 50, 60, 70, 80, 90 or 95% of the luciferase activity of the luciferase of SEQ ID NO: 2. In a particularly preferred embodiment the variants have at least the luciferase activity of the luciferase of SEQ ID NO: 2, or greater activity.

Alternatively, amino acid substitutions may alter function in some degree. Such variants typically contain one or more non-conservative amino acid substitutions, deletions, insertions, inversions, or truncation or a substitution, insertion, inversion, or deletion in a critical residue or critical region. Similarly, FIG. 6, Tables 3 and 5, and the further details herein may be used to identify such alterations in critical domains/regions. Variants of altered function may also contain substitution of similar amino acids that result in no change or an insignificant change in function.

Amino acids that are essential for function may also be identified by methods known in the art, such as site-directed mutagenesis or alanine-scanning mutagenesis (Cunningham et al., Science 244:1081-1085 (1989). The latter procedure introduces single alanine mutations at every residue in the molecule. The resulting mutant molecules are then tested for biological activity, e.g. enzyme activity or shift is emission spectrum in assays. Sites that are critical for binding partner/substrate binding may also be determined by structural analysis such as crystallization, nuclear magnetic resonance or photoaffinity labeling (Smith et al., J. Mol. Biol. 224:899-904 (1992); de Vos et al. Science 255:306-312 (1992)). The crystal structure of *Photinus* luciferase is known (Conti et al. Structure 4:287-298 (1996) and may be referred to when performing identification of amino acids essential to function. See, for example, Nakatsu et al. (2006).

Peptide or enzyme peptide sequences are written and amino acid positions numbered from the initiating methionine, which is numbered "1", to the carboxy-terminal amino acid. A particular amino acid at a particular position is indicated with the one-letter designation of the amino acid, e.g. M for MET or methionine, followed by the position number of the relevant amino acid, e.g. M1 for the initiating methionine. As will be clear from the context, in some comparisons of peptide amino acid sequences of the invention with others, such as *Photinus* luciferases, the order in which the comparison is described indicates the relevant amino acid sequence to which the recited position refers. Thus, residues in *Arachnocampa richardsae* luciferase that differ from *Photinus pyralis* luciferase may be indicated as, for example, A343I351, which indicates that the Alanine at position 343 of the *Arachnocampa* sequence corresponds to the Isoleucine at position 351 of *P. pyralis*. Similarly, DEL 213-214 R218 indicates a deletion of Arginine at position 218 of *P. pyralis* that would, if the Arginine were present, fall between residues 213 and 214 of the *Arachnocampa* sequence. See, e.g., the alignments provided as FIG. 6A through FIG. 6E.

A substitution at a position in an amino acid sequence or peptide is indicated by the one letter designation for the amino acid, followed by the position number of the relevant non-substituted sequence or peptide, followed by one or more one letter designations for replacement amino acids. Thus, for example, substitution of Leucine at position 342 of the native *Photinus pyralis* luciferase with a Serine would be designated as L342S. Similar designations will be clear from the context and further details provided herein. For example, an alternative designation for L342S may be indicated as L342–>S. Similarly, the same change in additional luciferase sequences may be indicated with reference to any one such sequence as "substitution of Leu with Ser at the position aligning with $Leu_{342}$ of SEQ ID NO: 4".

The present invention further provides fragments of the peptides, in addition to proteins and peptides that comprise and consist of such fragments, particularly those comprising the residues identified in FIGS. 2, 3, 5 and SEQ ID NO: 2. The fragments to which the invention pertains, however, are not to be construed as encompassing fragments that may be disclosed publicly prior to the present invention.

Fragments of peptides of the invention including the N-terminus of the molecule may be generated by genetic engineering of translation stop sites within a coding region. Alternatively, treatment of polypeptide with proteolytic enzymes, known as proteases, can produce a variety of N-terminal, C-terminal and internal fragments. In certain embodiments, peptides may be synthesized by known methods. Examples of fragments may include contiguous residues of 5, 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, 300, 400, 500 or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

Such fragments may be chosen based on the ability to retain one or more of the biological activities of the enzyme peptide or could be chosen for the ability to perform a function, e.g. bind a substrate or act as an immunogen. Particularly important fragments are biologically active fragments, peptides that are, for example, about 10 or more amino acids in length. Such fragments will typically comprise a domain or motif of the enzyme peptide, e.g., active site, a transmembrane domain, a substrate-binding domain or an enzymatically active portion of the enzyme peptide. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis).

In one embodiment, the fragments have luciferase activity, which luciferase activity comprises catalysis of a luminescence reaction dependent on ATP, the luminescence reaction generates an emission spectrum with a maximum emission intensity at wavelengths less than or equal to 530 nm. Preferably the fragments have at least 25% of the luciferase activity of the luciferase of SEQ ID NO: 2, more preferably at least 40, 50, 60, 70, 80, 90 or 95% of the luciferase activity of the luciferase of SEQ ID NO: 2. In a particularly preferred embodiment the fragments have at least the luciferase activity of the luciferase of SEQ ID NO: 2, or greater activity.

Polypeptides of the invention may contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in enzyme peptides are described in basic texts, detailed monographs, and the research literature, and they are well known to those of skill in the art.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties, 2nd Ed., T. E. Creighton, W. H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al. (Meth. Enzymol. 182: 626-646 (1990)) and Rattan et al. (Ann. N.Y Acad. Sci. 663:48-62 (1992)).

Accordingly, the enzyme peptides of the present invention also encompass derivatives or analogs in which a substituted amino acid residue is not one encoded by the genetic code, in which a substituent group is included, in which the mature enzyme peptide is fused with another compound, such as a compound to increase the half-life of the enzyme peptide (for example, polyethylene glycol), or in which the additional amino acids are fused to the mature enzyme peptide, such as a leader or secretory sequence or a sequence for purification of the mature enzyme peptide or a pro-protein sequence.

Protein/Peptide Uses

The potential uses of the peptides of the present invention are based primarily on the source of the protein as well as the class/action of the protein. Such uses may readily be determined using the information provided herein, that which is known in the art, and routine experimentation. The proteins of the present invention (including variants and fragments that may have been disclosed prior to the present invention) are useful for biological assays related to enzymes that are related to members of the luciferases. Such assays involve any of the known enzyme functions or activities or properties of luciferases, generally. The peptides, fragments, or luciferases of the present invention may also be used in any method or composition known to those of skill in the art and to which a luciferase peptide or fragment may be suitably put. A non exclusive list of exemplary applications includes those disclosed in U.S. Pat. Nos. 6,927,037; 6,690,461; 6,602,658; 6,602,657; 6,586,196; 6,503,723; 6,297,018; 6,171,809; 6,143,502; and 6,068,979. Further, embodiments of the invention are suitable for application such as the excitatory partner in the technique known as Bioluminescence Resonance Energy Transfer (BRET) (See, e.g. WO/1999/066324).

The proteins of the present invention may be used to raise antibodies or to elicit another immune response; as a reagent (including the labelled reagent) in assays designed to quantitatively determine levels of the protein (or its binding partner or ligand) in biological fluids; and as markers for tissues in which the corresponding protein is preferentially expressed. Where the protein binds or potentially binds to another protein or ligand (such as, for example, in an enzyme-effector protein interaction or enzyme-ligand interaction), the protein may be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The polypeptides may be used to identify compounds that modulate enzyme activity of the protein in its natural state or an altered form. Both the enzymes of the present invention and appropriate variants and fragments may be used in high-throughput screens to assay candidate compounds for the ability to bind to the enzyme or participate in the luminescence reactions. These compounds may be further screened against a functional enzyme to determine the effect of the compound on the enzyme activity. Further, these compounds may be tested in animal or invertebrate systems to determine activity/effectiveness. Compounds may also be identified that activate (agonist) or inactivate (antagonist) the enzyme to a desired degree.

Further, the proteins of the present invention may be used to screen a compound for the ability to stimulate or inhibit interaction between the enzyme protein and a molecule that normally interacts with the enzyme protein, e.g. a substrate or a component of the signal pathway that the enzyme protein normally interacts, or co-factors involved in a luminescence reaction. Such assays typically include the steps of combining the enzyme protein with a candidate compound under conditions that allow the enzyme protein, or fragment, to interact with the target molecule, and to detect the formation of a complex between the protein and the target or to detect the biochemical consequence of the interaction with the enzyme protein and the target, such as a luminescence reaction of luciferases or an individual reaction step of the luminescence reaction.

Candidate compounds include, for example: (1) small organic and inorganic molecules (e.g., molecules obtained from synthetic combinatorial or natural product libraries); (2) antibodies (e.g., polyclonal, monoclonal, humanized, anti-idiotypic, chimeric, and single chain antibodies as well as Fab, F(ab').sub.2, Fab expression library fragments, and epitope-binding fragments of antibodies); (3) phosphopeptides (e.g., members of random and partially degenerate, directed phosphopeptide libraries, see, e.g., Songyang et al., Cell 72:767-778 (1993)); and (4) peptides such as soluble peptides, including Ig-tailed fusion peptides and members of random peptide libraries (see, e.g., Lam et al., Nature 354: 82-84 (1991); Houghten et al., Nature 354:84-86 (1991)) and combinatorial chemistry-derived molecular libraries made of D- or L-configuration amino acids.

One candidate compound is a variant peptide of the invention that competes for substrate binding against the peptide of, for example, SEQ ID NO:2. Other candidate compounds include mutant enzymes or appropriate fragments containing mutations that affect enzyme function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) enzyme activity. The assays typically involve an assay of events in the luminescence pathway that indicate enzyme activity. Any of the biological or biochemical functions mediated by the enzyme may be used as an endpoint assay. Specifically, a biological function of a cell or tissues that expresses the enzyme may be assayed.

The proteins of the present invention are useful in competition binding assays in methods designed to discover compounds that interact with the enzyme (e.g. binding partners, ligands, or substrates). Thus, a compound is exposed to an enzyme polypeptide under conditions that allow the compound to bind or to otherwise interact with the polypeptide. Soluble enzyme polypeptide is also added to the mixture. If the test compound interacts with the soluble enzyme polypeptide, it may increase or decrease the amount of complex formed or activity from the enzyme target. This type of assay is particularly useful in cases in which compounds are sought that interact with specific regions of the enzyme. Thus, the soluble polypeptide that competes with the target enzyme region is designed to contain peptide sequences corresponding to the region of interest.

To perform cell free screening assays of compounds or proteins of interest it is sometimes desirable to immobilize either the enzyme protein, or fragment, or its target molecule to facilitate separation of complexes from uncomplexed forms of one or both.

Agents that modulate one of the enzymes of the present invention may be identified using one or more of the above assays, alone or in combination. It is generally preferable to use a cell-based or cell free system first and then confirm activity in whatever other model system may be desired. Such model systems are well known in the art and may readily be employed in this context. This invention further includes novel agents or substrates identified by the above-described screening assays.

The peptides of the present invention also provide targets for diagnosing active protein activity, particularly activities and conditions that are known for other luciferases. Thus, the peptide may be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered enzyme activity in cell-based or cell-free assay, alteration in substrate or antibody-binding pattern, altered isoelectric point, direct amino acid sequencing, and any other of the known assay techniques useful for detecting mutations in a protein. Such an assay may be provided in a single detection format or a multi-detection format such as an antibody chip array. In vitro techniques for detection of peptide include enzyme linked immunosorbent assays (ELISAs), Western blots, immunoprecipitations and immunofluorescence using a detection reagent, such as an antibody or protein binding agent.

Multiple Reporter Assays

The present peptides of the invention are particularly suited to use in multiple reporter assays. Multiple, dual (or double) reporters are commonly used to improve experimental accuracy. The term "multiple reporter" refers to the simultaneous expression and measurement of two or more individual reporter enzymes within a single system. When used together, these individual reporter enzymes may be termed "co-reporters". In genetic reporting, examples that currently benefit from dual-reporter assays include individual cells or cell populations (such as cells dispersed in culture, segregated tissues, or whole animals) genetically manipulated to simultaneously express two different reporter genes. Most frequently, the activity of one gene reports the impact of the specific experimental conditions, while the activity of the second reporter gene provides an internal control by which all sets of experimental values can be normalized. Normalizing the activity of the experimental reporter to the activity of the internal control minimizes experimental variability caused by, for example, differences in cell viability or transfection efficiency. Other sources of variability, such as differences in pipetting volumes, cell lysis efficiency and assay efficiency, can be effectively eliminated. Thus, dual reporter assays often allow more reliable interpretation of the experimental data by reducing extraneous influences.

Examples that currently benefit from assays employing at least two reporters (i.e. dual reporter assays) include individual cells or cell populations (such as cells dispersed in culture, segregated tissues, or whole animals) genetically manipulated to simultaneously express two different reporter genes. Most frequently, the activity of one gene reports the impact of the specific experimental conditions, while the activity of the second reporter gene provides an internal control by which all sets of experimental values can be normalized.

Cell-free reconstituted systems that may benefit from multiple reporter technology are cellular lysates derived for the simultaneous translation, or coupled transcription and translation, of independent genetic materials encoding experimental and control reporter enzymes. Immuno-assays may, likewise, be designed for multiple reporting of both experimental and control values from within a single sample. See, for example, Promega Dual-Luciferase™ Reporter Assay system as well as Promega pGL3 Luciferase Reporter Vectors (available from Promega Corporation, Madison, Wis.) as well as U.S. Pat. Nos. 5,744,320 and 5,670,356.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

Many methods are known for generating or identifying antibodies to a given target peptide. Several such methods are described by Harlow, Antibodies, Cold Spring Harbor Press, (1989). In general, to generate antibodies, an isolated peptide is used as an immunogen and is administered to a mammalian organism, such as a rat, rabbit or mouse. The full-length protein, an antigenic peptide fragment or a fusion protein may be used. Particularly important fragments are those covering functional domains, such as the domains identified herein and domains of sequence homology or divergence amongst the family, such as those that may readily be identified using protein alignment methods and as presented in the FIG. 6.

Antibodies may be prepared from any region of the peptide as described herein. However, preferred regions will include those involved in function/activity or enzyme/binding partner interaction. FIG. 6A through FIG. 6E, and the information of Tables 3 and 5, along with the additional directions provided herein by way of the Examples may be used to identify particularly important regions and various sequence alignments may be used to identify conserved and unique sequence fragments.

An antigenic fragment will typically comprise at least 8 contiguous amino acid residues. The antigenic peptide may comprise, however, at least 10, 12, 14, 16 or more amino acid residues. Such fragments may be selected on a physical property, such as fragments correspond to regions that are located on the surface of the protein, e.g., hydrophilic regions or may be selected based on sequence uniqueness.

Detection of an antibody of the present invention may be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The antibodies may be used to isolate one of the proteins of the present invention by standard techniques, such as affinity chromatography or immunoprecipitation. The antibodies may facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism or over the course of development, whether normal or abnormal. Further, such antibodies may be used to detect protein in situ, in vitro, or in a cell lysate or supernatant in order to evaluate the abundance and pattern of expression. Antibody detection of free fragments of a full length protein may be used to identify turnover.

The antibodies are also useful for inhibiting protein function, for example, blocking the binding of the enzyme peptide to a binding partner such as a substrate. These uses may also be applied in an analytical context in which analysis involves inhibiting the protein's function. An antibody may be used, for example, to block binding, thus modulating (agonizing or antagonizing) the peptide's activity. Antibodies may be prepared against specific fragments containing sites required for function or against intact protein that is associated with a cell or organism.

The invention also encompasses kits for using antibodies to detect the presence of a protein in a biological sample. The kit may comprise antibodies such as a labeled or labelable antibody and a compound or agent for detecting protein in a biological sample; means for determining the amount of protein in the sample; means for comparing the amount of protein in the sample with a standard; and instructions for use. Such a kit may be supplied to detect a single protein or epitope or may be configured to detect one of a multitude of epitopes, such as in an antibody detection array. Arrays are described in detail below for nuleic acid arrays and similar methods have been developed for antibody arrays.

Nucleic Acid Molecules

The present invention provides isolated nucleic acid molecules as described in FIGS. 1, 2, 4, 5, and SEQ ID NO:s 1 and 3 and various modifications or fragments thereof. In particular embodiments, the invention provides isolated nucleic acid molecules that encode an enzyme peptide or protein of the present invention (cDNA, transcript and genomic sequence). Such nucleic acid molecules may consist of, consist essentially of, or comprise a nucleotide sequence that encodes one of the enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there may be some flanking nucleotide sequences, for example up to about 5 kilobasepairs (KB), 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it may be subjected to the specific manipulations described herein such as recombinant expression, preparation of probes and primers, and other uses specific to the nucleotide sequences.

Moreover, an "isolated" nucleic acid molecule, such as a transcript or cDNA molecule, may be substantially free of other cellular material, or culture medium when produced by recombinant techniques, or chemical precursors or other chemicals when chemically synthesized. However, the nucleic acid molecule may be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention as well as novel fragments thereof. Isolated nucleic acid molecules according to the present invention further include such molecules produced synthetically.

Accordingly, the present invention provides nucleic acid molecules that consist of the nucleotide sequences of the invention. A nucleic acid molecule consists of a nucleotide sequence when the nucleotide sequence is the complete nucleotide sequence of the nucleic acid molecule. The present invention further provides nucleic acid molecules that consist essentially of the nucleotide sequences of the invention. A nucleic acid molecule consists essentially of a nucleotide sequence when such a nucleotide sequence is present with only a few additional nucleic acid residues in the final nucleic acid molecule. The present invention further provides nucleic acid molecules that comprise the nucleotide sequences of the invention. A nucleic acid molecule comprises a nucleotide sequence when the nucleotide sequence is at least part of the final nucleotide sequence of the nucleic acid molecule. In such a fashion, the nucleic acid molecule may be only the nucleotide sequence or have additional nucleic acid residues, such as nucleic acid residues that are naturally associated with it or heterologous nucleotide sequences. Such a nucleic acid molecule may have a few additional nucleotides or may comprise several hundred or more additional nucleotides. A brief description of how various types of these nucleic acid molecules may be readily made or isolated is provided below.

The isolated nucleic acid molecules may encode a mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules may be in the form of RNA, such as mRNA, or in the form DNA, including cDNA and genomic DNA obtained by cloning or produced by chemical synthetic techniques or by a combination thereof. The nucleic acid, especially DNA, may be double-stranded or single-stranded. Single-stranded nucleic acid may be the coding strand (sense strand) or the non-coding strand (anti-sense strand).

The invention further provides nucleic acid molecules that encode fragments of the peptides of the present invention as well as nucleic acid molecules that encode obvious variants of the enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants may contain nucleotide substitutions, deletions, inversions and insertions. Variation may occur in either or both the coding and non-coding regions. The variations may produce both conservative and non-conservative amino acid substitutions.

As used in this application, the term "a nucleic acid molecule encoding a luciferase" refers to a nucleic acid molecule that has been isolated free of total cellular nucleic acid. The term "functionally equivalent codon" is used herein to refer to codons that encode the same amino acid, such as the six codons for arginine or serine (Table 2), and also refers to codons that encode biologically equivalent amino acids, as discussed in the following pages.

Allowing for the degeneracy of the genetic code, sequences are considered essentially the same as those set forth if they have at least about 50%, usually at least about 60%, more usually about 70%, most usually about 80%, preferably at least about 90% and most preferably about 95% of nucleotides that are identical to the nucleotide sequence of the invention. Sequences that are essentially the same as those set forth may also be functionally defined as sequences that are capable of hybridizing to a nucleic acid segment containing the complement of a polynucleotide under standard conditions. The term closely related sequences refers to sequences with either substantial sequence similarity or sequence that encode proteins that perform luciferase functions (i.e. one or more activity resulting in luminescence) or invoke similar antigenic responses as described herein. The term closely related sequence is used herein to designate a sequence with a minimum or 50% similarity with a polynucleotide or polypeptide with which it is being compared.

The DNA segments of the present invention include those encoding biologically functional equivalent luciferase proteins and peptides, as described above. Such sequences may arise as a consequence of codon redundancy and amino acid functional equivalency that are known to occur naturally within nucleotide sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes may be engineered through the application of site-directed mutagenesis techniques or may be introduced randomly and screened later for the desired function, as described below.

Naturally, the present invention also encompasses oligonucleotides that are complementary, or essentially complementary to the sequences of a polynucleotide encoding an *Arachnocampa* luciferase. Nucleic acid sequences that are "complementary" are those that are capable of base-pairing according to the standard Watson-Crick complementary rules. As used herein, the term "complementary sequences" means nucleotide sequences that are substantially complementary, as may be assessed by the same nucleotide comparison set forth above, or as defined as being capable of hybridizing to the nucleic acid segment of a polynucleotide under relatively stringent conditions such as those described herein.

Alternatively, the hybridizing segments may be shorter oligonucleotides. Sequences of 17 bases long should occur only once in a complex genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or 3500 bases and longer are contemplated as well. Such oligonucleotides or polynucleotides will typically find use, for example, as probes in Southern and Northern blots and as primers in amplification reactions, or for vaccines.

TABLE 2

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Naturally, the present invention also encompasses oligonucleotides that are complementary, or essentially complementary to the sequences of a nucleotide of the invention. Nucleic acid sequences that are "complementary" are those that are capable of base-pairing according to the standard Watson-Crick complementary rules. As used herein, the term "complementary sequences" means nucleotide sequences that are substantially complementary, as may be assessed by the same nucleotide comparison set forth above, or as defined as being capable of hybridizing to the nucleic acid segment of a polynucleotide under relatively stringent conditions such as those described herein.

The length of the fragment will be based on its intended use. For example, the fragment may encode epitope bearing regions of the peptide, or may be useful as DNA probes and primers. Such fragments may be isolated using the known nucleotide sequence to synthesize an oligonucleotide probe. A labeled probe may then be used to screen a cDNA library, genomic DNA library, or mRNA to isolate nucleic acid corresponding to the coding region. Further, primers may be used in PCR reactions to clone specific regions of gene. A probe/primer typically comprises substantially a purified oligonucleotide or oligonucleotide pair.

Orthologs, homologs, and allelic variants may be identified using methods well known in the art. As described in the Peptide Section, these variants comprise a nucleotide sequence encoding a peptide that is typically 60-70%, 70-80%, 80-90%, and more typically at least about 90-95% or more homologous to the nucleotide sequence shown in the Figure sheets or a fragment of this sequence. Such nucleic acid molecules may readily be identified as being able to hybridize under moderate to stringent conditions, to the nucleotide sequence shown in the Figure sheets or a fragment of the sequence. Allelic variants may readily be determined by genetic locus of the encoding gene.

As used herein, and as well known to those of skill in the art, "high stringency conditions", "moderate stringency conditions" and "low stringency conditions" for nucleic acid hybridizations are explained on pages 2.10.1-2.10.16 and pages 6.3.1-6 in Current Protocols in Molecular Biology (Ausubel, F. M. et al., "Current Protocols in Molecular Biology", John Wiley & Sons, (1998)). The exact conditions which determine the stringency of hybridization depend not only on ionic strength (e.g., 0.2×SSC, 0.1×SSC), temperature (e.g., room temperature, 42 degrees Celsius, 68 degrees Celsius) and the concentration of destabilizing agents such as formamide or denaturing agents such as SDS, but also on factors such as the length of the nucleotide sequence, base composition, percent mismatch between hybridizing sequences and the frequency of occurrence of subsets of that sequence within other non-identical sequences. Thus, high, moderate or low stringency conditions can be determined empirically. By varying hybridization conditions from a level of stringency at which no hybridization occurs to a level at which hybridization is first observed, conditions which will allow a given sequence to hybridize (e.g., selectively) with the most similar sequences in the sample can be determined.

Exemplary conditions are described in Krause, M. H. and S. A. Aaronson, Methods in Enzymology, 200:546-556 (1991). Also see Ausubel et al., "Current Protocols in Molecular Biology", John Wiley & Sons, (1998), which describes the determination of washing conditions for moderate or low stringency conditions. Washing is the step in which conditions are usually set so as to determine a minimum level of complementary of the hybrids. Generally, starting from the lowest temperature at which only homologous hybridization occurs, each degrees Celsius by which the final wash temperature is reduced (holding SSC concentration constant) allows an increase by 1% in the maximum extent of mismatching among the sequences that hybridize. Generally, doubling the concentration of SSC results in an increase in Tm of about 17 degrees Celsius Using these guidelines, the washing temperature can be determined empirically for high, moderate or low stringency, depending on the level of mismatch sought.

For example, a low stringency wash can comprise washing in a solution containing 0.2×SSC/0.1% SDS for 10 min at room temperature; a moderate stringency wash can comprise washing in a prewarmed solution (42 degrees Celsius) solution containing 0.2×SSC/0.1% SDS for 15 min at 42 degrees Celsius; and a high stringency wash can comprise washing in prewarmed (68 degrees Celsius) solution containing 0.1× SSC/0.1% SDS for 15 min at 68 degrees Celsius. Furthermore, washes can be performed repeatedly or sequentially to obtain a desired result as known in the art. Equivalent conditions can be determined by varying one or more of the parameters given as an example, as known in the art, while maintaining a similar degree of identity or similarity between the target nucleic acid molecule and the primer or probe used.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript RNA or cDNA and genomic DNA to isolate full-length cDNA and genomic clones encoding the peptides described and to isolate cDNA and genomic clones that correspond to variants (alleles, orthologs, etc.) producing the same or related peptides.

The probe may correspond to any sequence along the entire length of the nucleic acid molecules provided. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence. As mentioned above, antisense molecules expressly include RNA constructs effective in achieving modulation of expression by RNA interference.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene or gene product. For example, an endogenous coding sequence may be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic organisms expressing all, or a part, of the nucleic acid molecules and peptides.

The nucleic acid molecules are also useful as hybridization probes for determining the presence, level, form and distribution of nucleic acid expression. Accordingly, the probes may be used to detect the presence of, or to determine levels of, a specific nucleic acid molecule in cells, tissues, and in organisms. The nucleic acid whose level is determined may be DNA or RNA. Accordingly, probes corresponding to the peptides described herein may be used to assess expression or gene copy number in a given cell, tissue, or organism.

In vitro techniques for detection of mRNA include Northern hybridizations and in situ hybridizations. In vitro techniques for detecting DNA includes Southern hybridizations and in situ hybridization.

An assay for enzyme nucleic acid expression may involve direct assay of nucleic acid levels, such as mRNA levels, or on collateral compounds involved in the luminesence reaction. Further, the expression of genes that are up- or down-regulated in response to a signal or environmental agent or condition may also be assayed. In this embodiment the regulatory regions of these genes may be operably linked to a reporter gene encoding one or more luciferase peptides of the invention.

Thus, modulators of enzyme gene expression may be identified in a method wherein a cell is contacted with a candidate compound and the level of luminescence (i.e. intensity or spectrum) determined. The characteristics (spectrum, intensity distribution, absolute intensity, etc.) of luminescence in the presence of the candidate compound is compared to the characteristics of luminescence in the absence of the candidate compound. The candidate compound may then be identified as a modulator of nucleic acid expression based on this comparison and be used, for example to treat a disorder characterized by aberrant nucleic acid expression.

Alternatively, a modulator for enzyme nucleic acid expression may be a small molecule or drug identified using the screening assays described herein as long as the drug or small molecule inhibits the enzyme nucleic acid expression in the cells and tissues that express the protein.

The nucleic acid molecules are useful as antisense constructs to control enzyme gene expression in cells, tissues, and organisms. A DNA antisense nucleic acid molecule is designed to be complementary to a region of the gene involved in transcription, preventing transcription and hence production of enzyme protein. An antisense RNA or DNA nucleic acid molecule would hybridize to the mRNA and thus block translation of mRNA into enzyme protein. Techniques and methods of performing RNA interference are expressly included in these techniques.

The invention also encompasses kits for detecting the presence of an enzyme nucleic acid in a biological sample. For example, the kit may comprise reagents such as a labeled or labelable nucleic acid or agent capable of detecting enzyme nucleic acid in a biological sample; means for determining the amount of enzyme nucleic acid in the sample; and means for comparing the amount of enzyme nucleic acid in the sample with a standard. The compound or agent may be packaged in a suitable container. The kit may further comprise instructions for using the kit to detect enzyme protein mRNA or DNA.

Nucleic Acid Arrays

The present invention further provides nucleic acid detection kits, such as arrays or microarrays of nucleic acid molecules that are based on the sequence information provided.

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, WO/1995/011995, Lockhart, D. J. et al. (1996; Nat. Biotech. 14: 1675-1680) and Schena, M. et al. (1996; Proc. Natl. Acad. Sci. 93: 10614-10619). In other embodiments, such arrays are produced by the methods described in U.S. Pat. No. 5,807,522.

The microarray or detection kit is preferably composed of a large number of unique, single-stranded nucleotide sequences, usually either synthetic antisense oligonucleotides or fragments of cDNAs, fixed to a solid support. The oligonucleotides are preferably about 6-60 nucleotides in length, more preferably 15-30 nucleotides in length, and most preferably about 20-25 nucleotides in length. For a certain type of microarray or detection kit, it may be preferable to use oligonucleotides that are only 7-20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In an example of a sample analysis using a microarray or detection kit, the RNA or DNA from a biological sample may be made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementary. After removal of nonhybridized probes, a scanner is used to determine the levels and patterns of fluorescence. The scanned images are examined to determine degree of complementary and the relative abundance of each oligonucleotide sequence on the microarray or detection kit. The biological samples may be obtained from any suitable source of interest. A detection system may be used to measure the absence, presence, and amount of hybridization for all of the distinct sequences simultaneously. This data may be used for large-scale correlation studies on the sequences, expression patterns, mutations, variants, or polymorphisms among samples, species, or environmental samples.

The test samples of the present invention include cells, protein or membrane extracts of cells or even crude environmental samples. The test sample used in the above-described method will vary based on the assay format, nature of the detection method and the tissues, cells or extracts used as the sample to be assayed. Methods for preparing nucleic acid extracts or of cells are well known in the art and may be readily be adapted in order to obtain a sample that is compatible with the system utilized.

In another embodiment of the present invention, kits are provided which contain the necessary reagents to carry out the assays of the present invention.

Vectors/Host Cells

The invention also provides vectors containing the nucleic acid molecules described herein. The term "vector" refers to a vehicle, preferably a nucleic acid molecule, which may transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector may be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors may function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules may be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor may be produced from the vector itself. It is understood, however, that in some embodiments, transcription or translation of the nucleic acid molecules may occur in a cell-free system.

The regulatory sequence to which the nucleic acid molecules described herein may be operably linked include promoters for directing mRNA transcription. These include, but are not limited to, the left promoter from bacteriophage X, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors may also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., Molecular Cloning: A Laboratory Manual. 2nd. ed., Cold Spring Harbor Laboratory Press, Cold Spring Harbor, N.Y., (1989).

A variety of expression vectors may be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., Molecular Cloning: A Laboratory Manual. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules may be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule may be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors may increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide may ultimately be separated from the fusion moiety. Proteolytic enzymes include, but are not limited to, factor Xa, thrombin, and enteroenzyme. Typical fusion expression vectors include pGEX (Smith et al., Gene 67:31-40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., Gene 69:301-315 (1988)) and pET 11d (Studier et al., Gene Expression Technology: Methods in Enzymology 185:60-89 (1990)).

Recombinant protein expression may be maximized in host bacteria by providing a genetic background wherein the host cell has an impaired capacity to proteolytically cleave the recombinant protein. (Gottesman, S., Gene Expression Technology: Methods in Enzymology 185, Academic Press, San Diego, Calif. (1990)119-128). Alternatively, the sequence of the nucleic acid molecule of interest may be altered to provide preferential codon usage for a specific host cell, for example *E. coli*. (Wada et al., Nucleic Acids Res. 20:2111-2118 (1992)).

The nucleic acid molecules may also be expressed by expression vectors that are operative in yeast. Examples of vectors for expression in yeast e.g., *S. cerevisiae* include pYepSec1 (Baldari, et al, EMBO J. 6:229-234 (1987)), pMFa (Kujan et al., Cell 30:933-943(1982)), pJRY88 (Schultz et al., Gene 54:113-123 (1987)), and pYES2 (Invitrogen Corporation, San Diego, Calif.).

The nucleic acid molecules may also be expressed in insect cells using, for example, baculovirus expression vectors. Baculovirus vectors available for expression of proteins in cultured insect cells (e.g., Sf 9 cells) include the pAc series (Smith et al., Mol. Cell Biol. 3:2156-2165 (1983)) and the pVL series (Lucklow et al., Virology 170:31-39 (1989)).

In certain embodiments of the invention, the nucleic acid molecules described herein are expressed in mammalian cells using mammalian expression vectors. Examples of mammalian expression vectors include pCDM8 (Seed, B. Nature 329:840(1987)) and pMT2PC (Kaufman et al., EMBO J. 6:187-195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

The invention also encompasses vectors in which the nucleotide sequences described herein are cloned into the vector in reverse orientation, but operably linked to a regulatory sequence that permits transcription of antisense RNA. Thus, an antisense transcript may be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells. Host cells can include, but are not limited to, silk worm larvae, CHO cells, *E. coli*, and yeast.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989).

Host cells may contain more than one vector. Thus, different nucleotide sequences may be introduced on different vectors of the same cell. Similarly, the nucleic acid molecules may be introduced either alone or with other nucleic acid molecules that are not related to the nucleic acid molecules such as those providing trans-acting factors for expression vectors. When more than one vector is introduced into a cell, the vectors may be introduced independently, co-introduced or joined to the nucleic acid molecule vector.

In the case of bacteriophage and viral vectors, these may be introduced into cells as packaged or encapsulated virus by standard procedures for infection and transduction. Viral vectors may be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker may be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins may be produced in bacteria, yeast, mammalian cells, and other cells under the control of the appropriate regulatory sequences, cell-free transcription and translation systems may also be used to produce these proteins using RNA derived from the DNA constructs described herein.

Where secretion of the peptide is desired, which is difficult to achieve with multi-transmembrane domain containing proteins such as enzymes, appropriate secretion signals are incorporated into the vector. The signal sequence may be endogenous to the peptides or heterologous to these peptides.

Where the peptide is not secreted into the medium, the protein may be isolated from the host cell by standard disruption procedures, including freeze thaw, sonication, mechanical disruption, use of lysing agents and the like. The peptide may then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides may have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing an enzyme protein or peptide that may be further purified to produce desired amounts of enzyme protein or fragments. Thus, host cells containing expression vectors are useful for peptide production.

Host cells are also useful for conducting cell-based assays involving the enzyme protein or enzyme protein fragments, such as those described above as well as other formats known in the art. Thus, a recombinant host cell expressing a native enzyme protein is useful for assaying compounds that stimulate or inhibit enzyme protein function.

Host cells are also useful for identifying enzyme protein mutants in which these functions are affected. If the mutants naturally occur and give rise to a pathology, host cells containing the mutations are useful to assay compounds that have a desired effect on the mutant enzyme protein (for example, stimulating or inhibiting function) which may not be indicated by their effect on the native enzyme protein.

Transgenics

The *Arachnocampa* luciferase nucleic acids can be used to generate transgenic, non-human plants or animals or site specific gene modifications in cell lines. Transgenic cells of the subject invention include one or more nucleic acids according to the invention present as a transgene, where included within this definition are the parent cells transformed to include the transgene and the progeny thereof.

In many embodiments, the transgenic cells are cells that do not normally harbor or contain a nucleic acid according to the subject invention. In those embodiments where the transgenic cells do naturally contain the subject nucleic acids, the nucleic acid will be present in the cell in a position other than its natural location, i.e. integrated into the genomic material of the cell at a non-natural location.

Transgenic animals may be made through homologous recombination, where the endogenous locus is altered. Alternatively, a nucleic acid construct is randomly integrated into the genome. Vectors for stable integration include plasmids, retroviruses and other animal viruses, YACs, and the like.

Transgenic organisms of the subject invention include cells and multicellular organisms, e.g., plants and animals, that are endogenous knockouts in which expression of the endogenous gene is at least reduced if not eliminated. Transgenic organisms of interest also include cells and multicellular organisms, e.g., plants and animals, in which the protein or variants thereof is expressed in cells or tissues where it is not normally expressed or is expressed at levels not normally present in such cells or tissues. DNA constructs for homologous recombination will comprise at least a portion of the gene of the subject invention, wherein the gene has the desired genetic modification(s), and includes regions of homology to the target locus. DNA constructs for random integration need not include regions of homology to mediate recombination. Conveniently, markers for positive and negative selection may be included.

Methods for generating cells having targeted gene modifications through homologous recombination are known in the art. For various techniques for transfecting mammalian cells, see Keown et al. (1990), Meth. Enzymol. 185:527-537. For embryonic stem (ES) cells, an ES cell line may be employed, or embryonic cells 10 may be obtained freshly from a host, e.g. mouse, rat, guinea pig, eta Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a 15 selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the 20 blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny may be readily detected. The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies or screening for modulators, or other uses as provided or known to those of skill in the art.

Transgenic plants may be produced and used in a similar manner. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956. Methods of producing transgenic plants are also reviewed in Plant Biochemistry and Molecular Biology (eds. Lea & Leegood, John Wiley & Sons)(1993) pp 275-295.

In brief, a suitable plant cell or tissue is harvested, depending on the nature of the plant species. As such, in certain instances, protoplasts will be isolated, where such protoplasts may be isolated from a variety of different plant tissues, e.g. leaf, hypoctyl, root, etc. For protoplast isolation, the harvested cells are incubated in the presence of cellulases in order to remove the cell wall, where the exact incubation conditions vary depending on the type of plant or tissue from which the cell is derived. The resultant protoplasts are then separated from the resultant cellular debris by sieving and centrifugation. Instead of using protoplasts, embryogenic explants comprising somatic cells may be used for preparation of the transgenic host. Following cell or tissue harvesting, exogenous DNA of interest is introduced into the plant cells. A variety of different techniques are available for such introduction. With isolated protoplasts, the opportunity arise for introduction via DNA-mediated gene transfer protocols, including: incubation of the protoplasts with naked DNA, e.g. plasmids, comprising the exogenous coding sequence of interest in the presence of polyvalent cations, e.g. PEG or PLO; and electroporation of the protoplasts in the presence of naked DNA comprising the exogenous sequence of interest.

Protoplasts that have successfully taken up the exogenous DNA are then selected, grown into a callus, and ultimately into a transgenic plant through contact with the appropriate amounts and ratios of stimulatory factors, e.g. auxins and cytokinins. With embryogenic explants, a convenient method of introducing the exogenous DNA in the target somatic cells is through the use of particle acceleration or "gene-gun" protocols. The resultant explants are then allowed to grow into chimera plants, cross-bred and transgenic progeny are obtained.

Instead of the naked DNA approaches described above, another convenient method of producing transgenic plants is Agrobacterium mediated transformation. With Agrobacterium mediated transformation, co-integrative or binary vectors comprising the exogenous DNA are prepared and then introduced into an appropriate Agrobacterium strain, e.g. A. tumefaciens. The resultant bacteria are then incubated with prepared protoplasts or tissue explants, e.g. leaf disks, and a callus is produced. The callus is then grown under selective conditions, selected and subjected to growth media to induce root and shoot growth to ultimately produce a transgenic plant.

Any of the regulatory or other sequences useful in expression vectors may form part of the transgenic sequence. This includes intronic sequences and polyadenylation signals, if not already included. A tissue-specific regulatory sequence(s) may be operably linked to the transgene to direct expression of the enzyme protein to particular cells.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus may be considered to constitute preferred modes for its practice. However, those of skill in the art should, in light of the present disclosure, appreciate that many changes may be made in the specific embodiments which are disclosed and still obtain a like or similar result without departing from the spirit and scope of the invention.

Miscellaneous Materials and Methodology Employed in the Examples

Insects

Individuals of *Arachnocampa richardsae* were collected from the wild under informed consent obtained from the NSW National Parks and Wildlife Service. One hundred larval *A. richardsae* were collected from the Newnes Railway Tunnel, map no. 8931, grid reference E414 N187, New South Wales, Australia. The larvae were transferred to the laboratory and light organs were dissected from the rest of the carcass under a microscope.

*Arachnocampa* species may be cultured by means known in the art. See: Takaie, H. (1989) Breeding and display of the glow-worms, *Arachnocampa* spp. Insectarium, vol. 26 July: 214-219; Takaie, H. (1997) Ten years of the glow-worm (*Arachnocampa richardsae*) rearing at Tama Zoo—Fascination of a living milky way. Insectarium, vol 34 November: 336-342. Sakurai, Y., R. Komatani, K. Tabata and H. Takaie On the glow-worm breeding at Tama Zoo.

RNA Isolation: Total RNA was isolated from either one carcass or approximately 10 light organs using the RNAqueous™-Micro Kit (Ambion) according to the manufacturer's instructions, except that the tissue was ground in 300 µl Lysis Solution.

cDNA Library: cDNA libraries representative of the carcass and light organ were constructed using the Creator™ SMART™ cDNA Library Construction Kit (Clontech) with modification. First strand cDNA was synthesised by the long distance (LD) PCR method described using one microgram total RNA and cDNA amplified using 20 cycles. Two micrograms of amplified ds cDNA underwent Proteinase K and SfiI digestion as described by the manufacturer and was fractionated on a cDNA size fractionation column (Invitrogen) according to the manufacturer's instructions. Individual fractions (up to 100 ng ds cDNA) were ligated with 100 ng SfiI-digested pDNR-LIB and were subsequently electroporated into ElectroMAX™ DH10β™ T1Phage Resistant *E. coli* (Invitrogen). A glycerol stock of each cDNA library was prepared by diluting the unamplified library 1:2 with 50% (v/v) glycerol-LB. Additionally, glycerol stocks of 1056 individually picked clones from each light organ cDNA library were prepared in 96-well polystyrene flat bottomed plates with low evaporation lids (Becton Dickinson) by inoculating 100 µl 10% (v/v) glycerol-LB with a single colony and incubating overnight at 37° C. These were stored frozen at −80° C.

Plasmid Isolation: For each of the two light-organ cDNA libraries (fraction 10 library and fraction 9 library), plasmid DNA was prepared from 96 randomly-picked clones.

96-well Plasmid DNA Preparation: Plasmid DNA was prepared according to a method modified from information supplied by Millipore Corporation (Beckman Coulter—Biomek 2000 Workstation™—Millipore Protocols, August 2002). Individual colonies were inoculated into 1.1 ml 2× Luria Broth containing 30 µg mL-1 chloramphenicol in sterile 96 deep-well plates. Plates were covered with AeraSeal™ (Excel Scientific, Wrightswood Calif.) and incubated at 37° C. in an orbital shaker set at 320 rpm for 24 hours. The plates were centrifuged at 1500 g for five minutes at room temperature and supernatant was decanted and excess fluid was removed from the pellet by tapping the plate firmly on a tissue.

Using the BioMek2000™ robotic workstation (Beckman Coulter), 150 µl of Solution 1 (30 mM glucose, 15 mM Tris-HCl (pH 8.0), 30 mM Na2EDTA, 60 µg/ml RNaseA) was added to each well and mixed. The plate was manually vortexed for three minutes. 150 µl of Solution 2 (0.2N NaOH, 1% (w/v) SDS) was added, followed by 150 µl of Solution 3 (3.6M Potassium; 6M Acetate). Well contents were mixed thoroughly. 300 µl of the crude lysates were transferred to a MultiScreen™ clearing plate (Millipore), which was placed over a Plasmid™ plate (Millipore) on a vacuum manifold. The lysate was filtered under vacuum (seven minutes 203 mm Hg). The clearing plate was discarded and the lysate was vacuum-filtered over the Plasmid plate (8 minutes; 508 mm Hg). The Plasmid plate was washed for six minutes under the same vacuum with 200 µl water per well. The vacuum was released, 35 µl of 10 mM Tris (pH8.0) was added to each well of the Plasmid plate, which plate was shaken at 600 rpm for 15 minutes. The well contents, containing the plasmid DNA, were collected with a multichannel pipette.

Sequencing: Clones were sequenced using the CEQ 2000 Dye Terminator Cycle Sequencing™ with Quick Start Kit™ (Beckman Coulter) and 100 fmol of plasmid DNA.

Dot blotting for screening of clones from *A. richardsae* light organ cDNA library: Clones from the glowworm light organ cDNA library (fraction 9) glycerol stocks were spotted onto Hybond-XL™ membranes (Amersham) using a 96-well replicator (V & P Scientific, Inc.). Membranes were then denatured, neutralised and fixed according to the manufacturer's instructions.

Dot blots were probed with a 796 bp $\alpha^{32}$P-dATP-labelled PCR probe prepared using the following primers:

```
forward primer GWLucScreenU
                            (SEQ ID NO: 11)
5'-GATGATAATGCACCAGAAAAG-3' directed to nucleo-
tides 142-162 of clone 1E1 reverse primer GWLucScreenL
                            (SEQ ID NO: 12)
5'-TTATAATATCCAGCATCACCA-3' directed to nucleo-
tides 938-918 of clone 1E1.
```

The PCR probe was generated with Taq DNA Polymerase (Invitrogen), using cDNA clone 1E1 as template following the method of Millican and Bird (Millican and Bird 1997). Blots were hybridised and washed according to the membrane manufacturer's instructions, then exposed to X-ray film. Plasmid DNA was purified from clones that hybridised to 1E1 and the insert was sequenced.

Construction of full length cDNA encoding luciferase of *A. richardsae*: Two versions of the *Arachnocampa richardsae* luciferase cDNA were prepared. GWLuc#1 (Sequence 4) contained the consensus coding sequence, while GWLuc#2 contains a single, silent, departure from the consensus at position 1308. GWLuc#1 and GWLuc#2 also differ at a single base in the 3' UTR.

GWLuc#1 was constructed using the 5' region of clone 8F5 and the 3' region of clone 4F12. Clone 8F5 is a full length cDNA isolated from the Fraction 9 Glowworm light organ cDNA library (Plate 8; Position F5). It contains three differences from the consensus in the region 3' of a unique BamHI site (1030). Clone 4F12 is a partial cDNA, 1.5 kb in length, which 3' of the same BamH1 site, conforms exactly to the consensus coding sequence. Accordingly, the 3' end of clone 8F5 between the BamHI site and the XhoI site in the MCS of pDNR-LIB was removed and the corresponding fragment from clone 4F12 was spliced to clone 8F5.

GWLuc#2 was constructed using the same 8F5 clone as described above, in this case with the region 3' of the unique BamHI site being replaced with the corresponding fragment inserted from clone 1B6 (replacing a T with a C).

Constructs were amplified by PCR using Platinum Pfx™ DNA polymerase (Invitrogen) following the manufacter's instructions.

Preparation of luciferin extract: An *Arachnochampa* luciferin (hereinafter "GWLuciferin") containing fraction was prepared from light organs of *Arachnocampa* according to Viviani (Viviani, Hastings et al. 2002)). 90 light organs from *A. richardsae* were homogenized in hot 0.1 M citrate buffer pH 5. The suspension was incubated at 95° C. for 5 minutes, and acidified to pH 2.5-3.0 with 0.1 M HCl. The extract was extracted with an equal volume of ethyl acetate and dried under nitrogen. The residue was dissolved in water.

Multiple sequence alignments: Multiple sequence alignments and phylogenetic trees were derived using the PROTML or PROTPARS programs: PROTML (Adachi, J. and Hasegawa, M. 1996: Molphy Version 2.3. Programs for molecular Phylogenetics based on maximum likelihood. Computer Science monographs No. 28. A publication of the Institute of Statistical Mathematics, Tokyo)); PROTPARS (Felsenstein, J. 1989. PHYLIP—Phylogeny Inference Package (Version 3.2) Cladistics 5: 164-166). Pairwise alignments and levels of sequence identity and homology were determined using BestFit (GCG). Sequence alignment programs were used through the BioManager interface provided by the Australian National Genomic Information Service.

Example 1

Isolation of Nucleic Acids Encoding *Arachnocampa* Luciferases

Carcass cDNA libraries were constructed from Fractions 8-10 of the fractionated carcass ds cDNA and light organ cDNA libraries were constructed from Fractions 9 and 10 of the fractionated ds cDNA, respectively.

Of the 96 clones isolated from each light organ cDNA library, 92 and 95 clones, respectively, sequenced successfully. Each sequence was queried against the NCBI databases using the tBLASTx program. No clones from the Fraction 10 light organ cDNA library were identified as having any homology to any luciferase, but five clones from the Fraction 9 light organ cDNA library had homologies to luciferases of luminescent beetles. Clones 1E1 (1275 bp); 1B6 (1163 bp); 1F7 (948 bp); 1G12 (768 bp); and 1C5 (494 bp) were fully sequenced and were shown to be independently-derived 5'-truncated partial cDNAs representing the same open reading frame and, in tBLASTx searches, all five showed homology to luciferases from *Phrixothrix vivianii* and *Phrixothrix hirtus*. These species of beetle (*Coleoptera*: Family Phengodidae) have luminescent larvae and are known as "railroad worms". All five cDNAs sequences were truncated to varying extents at the 5' end. Sequence analysis of the five clones identified 11 base substitutions at the 3' end, of which three are silent.

Despite the use of proof-reading DNA polymerase for cDNA amplifications (Advantage 2 Polymerase Mix, Clontech) a high level of putative sequence variation was obtained after each amplification step. This necessitated sequencing of multiple independent amplicons to determine an authentic sequence and to isolate an amplicon with this sequence. A similar phenomenon was observed when amplifying the *P. pyralis* luciferase with another proof-reading DNA polymerase (Pfx, Invitrogen). The luciferases of firefly and *Arachnocampa* share the unusual feature that there is a high proportion of nucleotide diads, which may possibly explain the relatively poor fidelity of PCR with these sequences as target.

Clones from the glowworm light organ cDNA library (fraction 9) glycerol stocks were spotted onto Hybond-XL membranes (Amersham), using a 96-well replicator (V & P Scientific, Inc.). Membranes were denatured, neutralised and fixed according to the manufacturer's instructions.

Of the 960 light-organ cDNA-containing colonies screened with the 1E1-derived probe, 29 (ca. 3%) gave a positive signal. Since the efficiency of contacting the membrane with the replicator was not absolute, this may have been an underestimate of the total number of positives. Of the approximately 1,000 colonies from the Fraction 9 carcass cDNA library screened with the 1E1 probe, none were found to be positive.

Twenty-one clones, those giving the strongest hybridisation signal, were screened by PCR using pDONRLIBM13F, directed against 5' vector sequence as the forward primer and GWLuc484, which is directed to nucleotide 804-788 of 1E1, as the reverse primer. Amplicons were obtained from ten of the target clones, confirming their overlap with the 5' end of 1E1. Four of the amplicons were shown to be longer than 1E1. One of them, obtained from clone 4F12, was 1.1 kilobase pairs long, indicating a total clone length of 1.5 kilobase pairs. The three other amplicons, obtained from clones 11B11, 8F5 and 6B6, were all the same length, 1.3 kilobase pairs, indicating each of the clones is 1.7 kilobase pairs long.

The sequence of the complete open reading frame of *A. richardsae* luciferase was deduced by sequencing of clones 1E1, 1B6, 1F7, 1C5, 1G12 and 11B11, 8F5 and 6B6. Sequences from at least three independent clones were compared at all nucleotide positions. The consensus nucleotide sequence is shown in FIG. 1A through FIG. 1B or SEQ ID NO: 1. In a small number of cases, a single one of the three or more sequenced clones had a different sequence from the consensus. These variations are listed in Table 3.

TABLE 3

Unique nucleotide variations in sequenced partial or full-length clones of *Arachnocampa richardsae*.

| nucleotide position in cDNA | Consensus | Variant |
|---|---|---|
| 190 | G | C |
| 215 | T | C |
| 613 | T | C |
| 654 | T | C |
| 702 | T | C |
| 920 | A | T |
| 1122 | A | G |
| 1159 | A | C |
| 1245 | T | C |

TABLE 3-continued

Unique nucleotide variations in sequenced partial or full-length clones of *Arachnocampa richardsae*.

| nucleotide position in cDNA | Consensus | Variant |
|---|---|---|
| 1291 | A | G |
| 1308 | T | C |
| 1310 | T | C |
| 1346 | T | C |
| 1491 | A | C |
| 1493 | A | T |

A PCR screen was performed in order to identify any additional untranslated sequence upstream of the 5' terminus that is common to clones 11B11, 8F5 and 6B6. cDNA clones representing the 5' end of the luciferase gene were obtained by semi-anchored PCR, using the *Arachnocampa* light organ cDNA as template. In construction of the *Arachnocampa* light organ cDNA (Creator SMART cDNA Library Construction Kit (Clontech), LD-PCR synthesis), the SMART IV Oligo primer had been added to all cDNA amplified. A portion of the SMART IV Oligo primer was therefore used to anchor the 5' end of the PCR reaction: 5'-CAACGCAGAGTGGCCATTA-3'(SEQ ID NO: 13). A luciferase gene-specific primer, directed to nucleotides 514-494 of the luciferase cDNA: 5'-TGGCTTTTCTGGTGCATTATC-3' (SEQ ID NO: 14) was used as the reverse primer. An aliquot of the *Arachnocampa* light organ cDNA pool, prepared as described earlier but prior to digestion and size-fractionation, was used as template. DNA was amplified with HotStarTaq DNA Polymerase (Qiagen). Amplicons (approximately 500 bp) were cloned into pGEMTeasy (Promega). Thirteen clones, identified as possessing the luciferase cDNA, were sequenced. Of these, eight had exactly the same 5' UTR sequence as the putative full-length luciferase cDNA clones 11B11, 8F5 and 6B6.

The cDNA shows a single long open reading frame in one translation frame. This sequence corresponds to that of SEQ ID NO: 2. The ORF commences with an AUG, in the correct AXXAUGG context for ribosome initiation (Kozak 1986; Kozak 1987) and ends with a UAA termination codon at nucleotide position 1621. The protein is 530 amino acids long, a similar length to other insect luciferases and luciferase-like proteins.

The luciferase has a calculated molecular weight of 58,955 and a calculated isoelectric point of 7.36. As such it is marginally smaller than the luciferase of *Photinus pyralis* (de Wet et al. 1987) and a number of other firefly luciferases. The calculated molecular weight of the *Arachnocampa* luciferase differs substantially from the value determined by gel filtration. Viviani, Hastings et al. (2002) teach a molecular weight of 36 kDa.

Example 2

Comparison of *Arachnocampa* Luciferase Sequence with Sequences of Other Insect Luciferases tBLASTX searches of the NCBI databases with the *Arachnocampa* luciferase sequence recovered hits with luciferase-like proteins from *D. melanogaster* and *Anopheles gambiae* and luciferases from *Phrixothrix viviani*, fireflies and other luminescent beetles. The amino acid homology between *Arachnocampa* luciferase and beetles commences at Asn 9 of the *Arachnocampa* sequence, corresponding to the conserved asparagine found between positions 5 and 9 in beetle luciferases (FIG. 6).

At the nucleotide level, the highest level of identity (58.1%) is with the luciferase of *P. viviani* but the level of identity with *Photinus pyralis* (57.1%) is almost as high (Table 4).

TABLE 4

Summary of pairwise sequence comparisons between *A. richardsae* luciferase, luciferases of two representative luminescent beetles and luciferase-like proteins of two non-luminescent flies. *Phrixothrix viviani* is the highest scoring luciferase hit generated using the *A. richardsae* as the query in a tBLASTx search of the NCBI sequence databases.

|  | Nucleotide level | Amino acid level | |
| --- | --- | --- | --- |
|  | % identity | % homology | % identity |
| *Phrixothrix viviani* luciferase (545 amino acids) | 58.1 | 48.3 | 34.9 |
| *Photinus pyralis* luciferase (550 amino acids) | 57.1 | 45.7 | 33.0 |
| *Drosophila melanogaster* luciferase-like protein (DroCG6178) (544 amino acids) | 55.6 | 51.2 | 38.8 |
| *Anopheles gambiae* luciferase-like protein (AgCP8896) (partial sequence of 493 amino acids). | 54.5 | 48.8 | 36.8 |

Luciferase-like proteins of *Drosophila* and *Anopheles* have marginally lower levels of nucleotide identity. At the amino acid level, the highest level of identity (38.8%) and homology (51.2%) is with the luciferase-like protein of *D. melanogaster*. The highest level of identity (34.9%) and homology (48.3%) with a functional luciferase is with the enzyme from *Phrixothrix viviani* (Table 4). Clearly, the luciferase of *Arachnocampa* species belong to the same gene superfamily as do the luciferases of fireflies and other beetles. It is also evident that the *Arachnocampa* luciferase is a novel member of the family, only distantly related to the beetle luciferases. This is emphasised by the observation that, at the amino acid level, the sequence similarity is greater with luciferase-like proteins that have no luminescent activity in vivo or in vitro.

Based on an alignment of luciferase sequences from 18 species of luminescent beetles, representing one genus from the family Elateridae, one genus from the family Phengodidae and eight genera from the family Lampyridae, beetle luciferases share 128 absolutely conserved amino acid residues (FIG. 6). Firefly luciferases are consistently approximately 550 amino acid residues in length. Accordingly approximately 23% of residues are absolutely conserved amongst all members of the beetle luciferase group sequenced to date. In contrast, only seven residues are completely conserved amongst all members of the luciferase, acyl-CoA ligase and peptide synthase superfamily (Conti et al. 1996). The sequence of the *A. richardsae* luciferase differs from that of the beetle luciferase consensus at 58 out of 128 positions (Table 3). The *A. richardsae* luciferase sequence therefore represents a profoundly different solution to the problem of luminescence from that exhibited by the fireflies.

TABLE 5

Listing of those 58 residues which are completely conserved amongst all beetle luciferases but at which the *A. richardsae* sequence diverges.

| Residue no. in *P. pyralis*[A] | Consensus residue in all Beetle luciferases | Residue in *A. richardsae* | Residue no. in *A. richardsae*[B] | Classification relative to the two dipteran luciferase-like proteins[#] |
| --- | --- | --- | --- | --- |
| 22 | A | Y | 26 | Anopheles sequence not available |
| 53 | Y | A | 54 | 1 |
| 63 | L | T | 64 | 3 |
| 83 | E | D | 84 | 3 |
| 88 | F | Y | 89 | 3 |
| 89 | F | Y | 90 | 4 |
| 91 | P | I | 92 | 4 |
| 103 | A | C | 104 | 3 |
| 109 | Y | W | 110 | 3 |
| 113 | E | D | 114 | 3 |
| 139 | V | I | 140 | 3 |
| 160 | G | P | 161 | 4 |
| 198 | S | T | 197 | 3 |
| 212 | H | Q | 211 | 2 |
| 218 | R | deletion | 213-214 | 4 |
| 224 | D | S | 219 | 4 |
| 225 | P | deletion | 219-220 | 4 |
| 228 | G | D | 221 | 5 |
| 233 | P | K | 226 | 4 |
| 242 | P | Q | 235 | 3 |
| 243 | F | Y | 236 | 5 |
| 245 | H | N | 238 | 3 |
| 253 | L | M | 246 | 5 |
| 255 | Y | R | 248 | 4 |
| 273 | F | Y | 266 | 3 |
| 280 | Y | F | 273 | 3 |
| 298 | S | K | 291 | 5 |
| 300 | L | E | 293 | 4 |
| 311 | E | R | 304 | 4 |
| 315 | G | S | 308 | 3 |
| 318 | P | T | 311 | 3 |
| 319 | L | V | 312 | 3 |
| 339 | G | F | 332 | 3 |
| 342 | L | S | 335 | 4 |
| 343 | T | S | 336 | 2 |
| 375 | D | H | 367 | 3 |
| 380 | K | A | 372 | 4 |
| 389 | E | F | 381 | 3 |
| 408 | T | S | 400 | 1 |
| 417 | W | Y | 409 | 3 |
| 418 | L | V | 410 | 3 |
| 427 | D | N | 419 | 3 |
| 441 | L | I | 433 | 3 |
| 442 | I | V | 434 | 3 |
| 443 | K | M | 435 | 3 |
| 444 | Y | V | 436 | 3 |
| 445 | K | D | 437 | 3 |
| 448 | Q | A | 440 | 3 |
| 452 | A | T | 444 | 3 |
| 458 | L | I | 450 | 3 |
| 485 | V | L | 477 | 3 |
| 486 | V | T | 478 | 3 |
| 490 | G | R | 481 | 4 |
| 506 | V | L | 497 | 4 |
| 513 | R | K | 504 | 4 |
| 516 | V | C | 507 | 3 |
| 527 | T | A | 518 | 5 |
| 549 | K | deletion | 530 et seq. | 3 |

Notes to Table 5:
[A] *P. pyralis* (M15055) luciferase length 550 amino acids.
[B] *A. richardsae* luciferase length 530 amino acids.
[#] Of the 57 changes where we have sequence for the Anopheles luciferase-like gene:
1. *A. richardsae* residue is the same as one of the two dipteran luciferase-like sequences but not the other.
2. Residue is the same for *A. richardsae*, *D. melanogaster* and *A. gambiae* but it is different from the beetle consensus.
3. *A. richardsae* residue is different from beetle consensus but *D. melanogaster* and *A. gambiae* luciferase-like proteins both have the same residue as the beetle consensus.
4. All three dipteran genes have different residues at this position.
5. *A. richardsae* residue is different from the beetle consensus and *D. melanogaster* and *A. gambiae* luciferase-like proteins both have the same residue, which is not the beetle consensus.

Example 3

Identification of Critical Amino Acids and Positions

All beetle luciferases tested to date use the same D-luciferin. Mutagenesis studies have revealed the importance of a number of residues in the substrate binding or catalytic mechanism of beetle luciferases. The luciferase of *A. richardsae* differs in sequence at a subset of these key residues. Arginine 218 of firefly luciferase has been shown to be an essential luciferin binding site residue (Branchini, Magyar et al. 2001). Replacement of R218 with glutamine, lysine or alanine, resulted in a 15-20 fold increase in the $K_M$ value for luciferin. The flash height (intensity) was reduced to 33%, 5% and 3.6%, respectively, of the wild-type value and $k_{cat}$ values were decreased. The wavelengths of the emission maximum were also reduced in all three mutants. R218 represents one of the aforementioned residues that is absolutely conserved in all 18 beetle luciferases examined. However, in the corresponding region of the *Arachnocampa* luciferase, four amino residues are deleted. The deletion, between *A. richardsae* N213 and L214 (Table 3) encompasses the position where the arginine, equivalent to R218 of *P. pyralis*, would be expected to occur (FIG. 6). *A. richardsae* residues K205, G206, V207 and H216, which span the deletion, are absolutely conserved between *Arachnocampa* and all 18 beetle luciferases (FIG. 6). Residues N213, L214 and I215, which directly border the deletion, are common with, respectively, 10, 2 and 2 other beetle luciferases. Therefore, the substrate binding characteristics of the *Arachnocampa* luciferase depart substantially from the properties of beetle luciferases in this region.

In a broader study (Branchini, Southworth et al. 2003), 15 residues (R218, H245, G246, F247, F250, T251, G315, G316, G341, L342, T343, S347, A348, I351, K529) believed to be positioned within 5 Å of the active site of *P. pyralis* luciferase, were mutated. The 11 residues in bold showed a fourfold or greater change in $K_M$ for D-luciferin. The residue at the corresponding position in *A. richardsae* luciferase differs in 10 of the 15 cases identified by Branchini (op.cit.; DEL 213-214 R218, N238H245, A239G246, T243F250, A244T251, S308G315, S335L342, S336T343, L339S347, A343I351; also see FIG. 6). The nature of the amino acid substitution or deletion in *Arachnocampa*, at each of these ten positions, is different from the experimental manipulations tested by Branchini et al., which were limited to the following: R218->K, Q, A (Branchini, Magyar et al. 2001; Branchini, Southworth et al. 2003); H245->F, D, A (Branchini, Magyar et al. 1998; Branchini, Magyar et al. 2001; Branchini, Southworth et al. 2003); G246->A; F247->Y, L, A; F250->S, G; T251->A; G315->A; G316->A; G341->A; L342->A; T343->A; S347->A; A348->V; I351->A; K529->A (Branchini, Southworth et al. 2003).

There is therefore no precedent for the *Arachnocampa* versions of these residues, even as individual substitutions. Furthermore, eight of the binding site residues tested by Branchini et al. (R218, H245, F247, G315, G341, L342, T343 and K529) are absolutely conserved amongst all 18 beetle luciferases that were used in the alignment. At the corresponding positions in *A. richardsae* (FIG. 6), five of these residues are subset of invariant residues that line the substrate binding pocket in beetle luciferases, the corresponding *Arachnocampa* residue is different in over 60% of cases as is reflected by the percentage similarity/identity between specified segments of *Arachnocampa* spp luciferase and *Photinus pyralis* sequence:

| | Polypeptide segment (residue number) | | |
|---|---|---|---|
| | 1-200 | 201-350 | 351-530(end) |
| *A. richardsae* | 43.4/28.6 | 38.0/27.3 | 52.8/41.1 |
| *A. tasmaniensis* | 44.1/30.8 | 38.0/28.7 | 54.4/41.1 |

Results were obtained using GAP (GCG/ANGIS). Note that BESTFIT results obtained were substantially the same.

Example 4

Similarities to Luciferase-Like Proteins of Other Diptera and Evolutionary Origins of *Arachnocampa* Luciferase Fifty-seven of the 58 amino acid residues where the luciferases of the invention differ from the concensus sequence of beetle luciferase fall in regions where sequence is available for "luciferase-like" proteins of both *D. melanogaster* and *A. gambiae*. At 33 of these 57 residues, the luciferase-like proteins conform to the sequence of the beetle luciferase (Table 5), even though the organisms do not luminesce. Based on these consensus residues, it appears that the luciferase of *A. richardsae* has been subject to evolutionary pressure to diverge away from the ancestral family. Based on our sequence data, it is not possible to conclude whether the luciferases of luminescent beetles and flies evolved from a common luminescent ancestor, or whether luminescence evolved independently in *Coleoptera* and *Diptera* from a luciferase-like protein of the acyl-CoA ligase family.

Example 5

Figure 7:
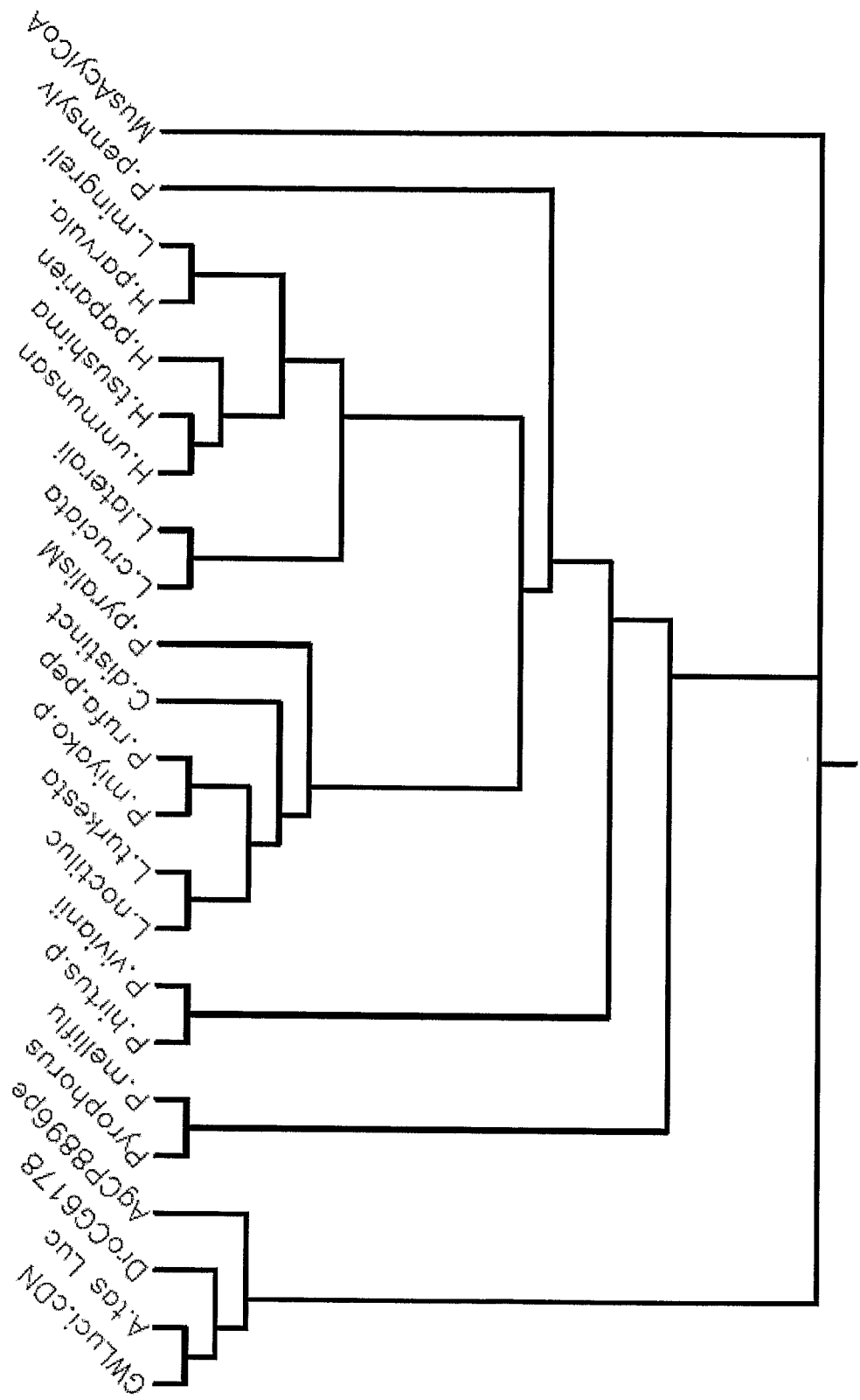
FIG. 7 Position of *Arachnocampa* luciferase in the molecular phylogeny of other luciferases of the acyl-CoA ligase superfamily.

Position of *Arachnocampa* Luciferase in the Molecular Phylogeny of Other Luciferases of the Acyl-CoA Ligase Superfamily An unanchored phylogenetic analysis using the PROTML program (FIG. 7) of 18 unique luciferase sequences from luminescent coleopterans, the luciferase-like proteins of *D. melanogaster* and *A. gambiae*, an acyl-CoA ligase from mouse and a novel luciferase from *A. richardsae* separates fireflies (Lampyridae: e.g. *Hotaria, Photinus, Lampyris, Luciola* and *Pyrocoelia*) from railroad worms (Phengodidae: i.e. *Phrixothrix* species) and click beetles (Elateridae: i.e. *Pyrophorus* species). The luciferase of *A. richardsae* was clearly separated from those of all three luminescent beetle families, although more closely related to the beetle luciferases than to the luciferase-like proteins of *diptera*. However, in a molecular phylogeny of the same sequences, anchored with the mouse acyl-Co ligase using the PROTPARS program (not shown), the *Arachnocampa* luciferase was placed as an outgroup to the *dipteran* luciferase-like proteins. The relationships among all other luciferases were unchanged.

Example 6

Expression of *Arachnocampa* Luciferase

Construction of pETDuet-1:GWLuc#1

The full length cDNA of GWLuc #1 was amplified using Platinum Pfx DNA polymerase (Invitrogen) following the manufacturer's recommendations using 10 pmol per reaction of the pETGWLucF and pETGWLucR PCR primers:

pETGWLucF:
GACACACCATGGCTTGTACTTCAGT            (SEQ ID NO: 15)

pETGWLucR:
GACGACCCTAGGTTACAATGTTCCTCTTAAA      (SEQ ID NO: 16)

These primers introduce NcoI and AvrII restriction sites 5' and 3' of the full length *Arachnocampa* luciferase cDNA. The purified PCR product was A-tailed as described in the pGEM T-easy Vector System I manual (Promega) and ligated into pGEM T-easy. The constructs were electroporated into the DH5α strain of *E. coli* and were sequenced using the CEQ 2000 Dye Terminator Cycle Sequencing with Quick Start Kit (Beckman Coulter) and 50 fmol plasmid DNA. Constructs containing an error-free *Arachnocampa* luciferase cDNA sequence were excised with NcoI and AvrII and inserted into the Novagen pET-Duet1 vector (EMD/Merck Biosciences, San Diego/Darmstadt) using the NcoI site of MCS1 and the AvrII site of MCS2. The resulting plasmid was designated pETDuet-1:GWLuc#1. The plasmids were electroporated in to the BL21(DE3) strain of *E. coli* and sequenced again.

Beetle Luciferase (*Photinus pyralis*) Control

A full length construct (1653 nucleotides) of the *P. pyralis* luc gene was inserted into the pETDuet-1 vector to give pETDuet-1:FFLuc, which was subsequently electroporated into *E. coli* strain BL21(DE3) as described for pETDuet-1: GWLuc#1.

Control Expression Vector

A control expression vector, pETDuet-1:Control was prepared from pETDuet-1 by excising MCS1 5' of the NcoI site through to the AvrII site of MCS2, which removes the His and S tags from MCS1 and MCS2, respectively. The resultant 5' overhangs were end-filled using DNA Polymerase I (Klenow, NEB) with 25 mM of each dNTP. The reaction was incubated at 25° C. for 15 minutes and was terminated by the addition of 10 mM EDTA and incubation at 75° C. for 20 minutes. The vector was purified and self-ligated using T4 DNA ligase (Fermentas) in the presence of 5% (w/v) PEG8000 according to Fermentas's recommendations for blunt ended ligations. The control vector was subsequently electroporated into *E. coli* strain BL21(DE3) as described for pETDuet-1:GWLuc#1.

Preinduction

Two milliliter (mL) cultures of the empty control vector pETDuet-1: control vector (in BL21(DE3)); pETDuet-1: FFLuc (firefly luciferase) construct (in BL21(DE3)); pETDuet-1: GWLuc (glow-worm luciferase) #1 construct (in BL21(DE3)) and untransformed BL21(DE3) cells were incubated overnight in LB media containing 1 M glucose at 37° C., 200 rpm. The next day, the cultures were centrifuged for three minutes at 1,500 rpm at room temperature and the pellet resuspended in 2 mL LB. 50 mL of LB was inoculated with a 1:50 dilution of each culture following the addition of 50 µL of 1000×ampicillin. These inoculated solutions were incubated at 37° C. for 1 hour before induction commenced. The absorbance of the cultures was measured at 600 nm (Abs600 nm) and upon achieving an Abs600 nm≧0.6 four 1 mL aliquots were removed, centrifuged at 10,000 g for five minutes at room temperature and the cell pellets stored at −80° C.

Induction

From the remaining culture volumes, two 9 mL aliquots were transferred to 50 mL conical centrifuge tubes. One aliquot was induced by the addition of IPTG (0.4 mM final concentration) and the second was not induced (added equivalent amount of water instead). The untransformed BL21(DE3) culture was not induced and 20 mL was transferred to a 250 mL conical flask. All of the cultures were then incubated at 20° C., 150 rpm for 48 hours at which time the Abs600 nm was measured. Three 250 µL aliquots were removed from each culture and centrifuged at 10,000 g for 5 minutes at room temperature and the pellets were stored at −80° C. for protein analysis. 5 mL of pETDuet-1: control vector; pETDuet-1: FFLuc and pETDuet-1: GWLuc#1 and 15mL of BL21 (DE3) cultures were transferred into clean centrifuge tubes and centrifuged at 4° C. for 10 minutes at 3,000 rpm. The supernatant was decanted, each pellet was resuspended in the respective starting volume of ice cold phosphate buffer saline (pH 7.4) (137 mM NaCl, 2.7 mM KCl, 4.3 mM $Na_2HPO_4$)) and centrifuged again at 4° C. for 10 minutes at 3,000 rpm. The PBS was decanted and the pellets resuspended in ice cold PBS adjusted to give the same Abs 600 nm as the most concentrated sample.

Protein Analysis

Protein analysis was performed using Invitrogen's NuPAGET™ Novex Bis-Tris gel system using the manufacturer's instructions. Frozen bacterial pellets were lysed by the addition of 1× NUPAGET™ Lauryl Dodecyl Sulphate (LDS) sample buffer containing 50 mM DTT and heated for 10 minutes at 70° C. Chromosomal DNA was sheared by passing the bacterial lysate through a 30 G needle several times. Bacterial samples of approximately equal protein concentrations, estimated by measuring the bacterial density (Abs600× dilution factor), and the SeeBlue™ pre-stained standard (Invitrogen) were loaded onto NUPAGET™ 12% Bis-Tris gels and electrophoresed for approximately 50 minutes at a constant 200 V using NUPAGE™ MOPS SDS running buffer (pH 7.7, 50 mM MOPS, 50 mM Tris, 0.1% (w/v) SDS, 1 mM EDTA) to which 1×NUPAGE™ antioxidant had been added in the upper chamber only of the XCell SureLock™ Mini-cell (Invitrogen).

Figure 8:
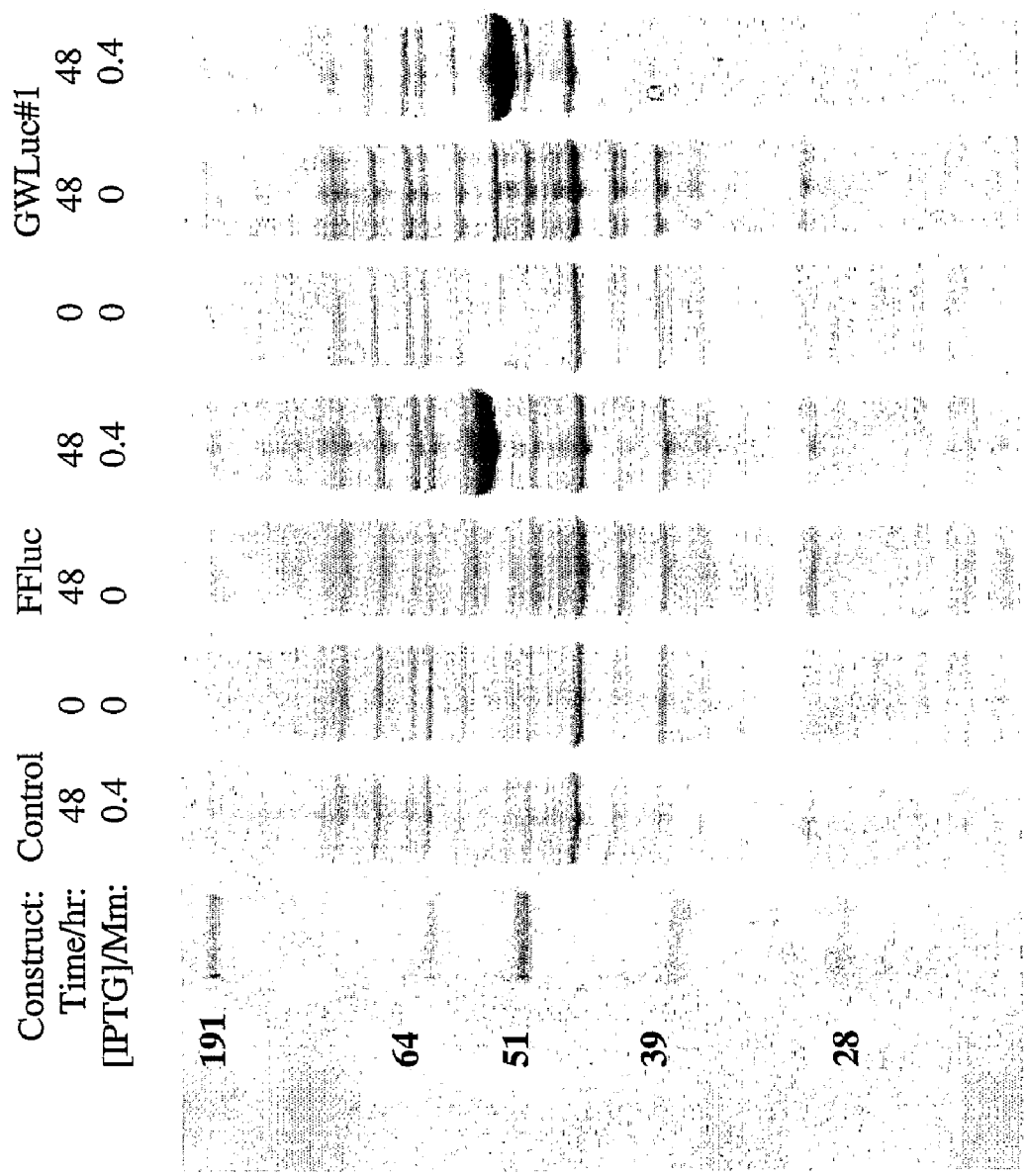
FIG. 8 Expression of peptides of the invention from GWLuc#1. Lane numbers are from left to right. The first lane displays molecular weight standards, labeled in kiloDaltons (kD). Other lanes display *E. coli* strain BL21(DE3) transformed with pETDuet-1:FFLuc (Lanes 3-5) and pETDuet-1:GWLuc#1 (Lanes 6-8). Lanes 4 and 7 display samples of cultures incubated for 48 hours without IPTG. Lanes 3 and 6 display pre-induction samples of the cultures. Lanes 5 and 8 display samples of cultures incubated for 48 hours in the presence of 0.4 mM IPTG and expressing the relevant constructs.

The gel was removed from the cassette and washed three times in 45% (v/v) methanol—10% (v/v) acetic acid for 10 minutes at room temperature with gentle agitation. Following the final wash, the gel was submerged in Fast stain (16% (v/v) Fast Stain stock solution (Fisher Biotec), 9% (v/v) methanol, 2% (v/v) acetic acid) and stained overnight at room temperature with gentle agitation. The stain solution was decanted and the gel initially rinsed in 10% (v/v) acetic acid for 10 minutes at room temperatures before being stored in 10% (v/v) acetic acid. The gels were photographed with transmitted fluorescent illumination using a video capture imaging system. FIG. 8 shows the LDS polyacrylamide gel electrophoresis of the induced pellets transformed with either pETDuet1: FFLuc (track 5) or the pETDuet1: GWLuc#1 (track 8) constructs exhibited similar patterns of protein expression. Transformed bacteria (with pETDuet1: FFLuc vector) induced with IPTG exhibited a new band midway between the 51 and 64 kDa (track 5) characteristic of firefly luciferase. Similarly IPTG induced bacteria transformed with pETDuet1:GWLuc#1 vector exhibit a new band (track 8) indicating the successful expression of *Arachnocampa* luciferase.

Preparation of Lysates

40 µL BL21(DE3) non-transformed cells were mixed with 50 µL of the pETDuet-1: control, pETDuet-1:FFLuc or pETDuet-1:GELuc#1 cultures, and 10 µL of 1M $H_2HPO_4$ (pH 7.8), 20 mM EDTA was added. Aliquots of the cell mix were snap frozen on dry ice and stored at −80° C. Frozen cells were thawed by placing the tube in a room temperature water bath. Cell aliquots were mixed with 300 µL freshly prepared lysis mix (1× luciferase cell culture lysis reagent (CCLR, Promega), 1.25 mg/mL lysozyme (Sigma), 2.5 mg/mL bovine serum albumin (BSA) (Sigma). Following incubation at room temperature for 10 minutes, the lysate was aliquoted and stored at −80° C. or used immediately.

Luciferin Assay

This luciferin assay used the cell lysates (above) containing *Arachnocampa* derived luciferase ("glow worm luciferase" or "GW luciferase"). 10 µL aliquots of the cell lysate (unless otherwise stated) were added to the wells of an OptiPlate™-96 plate. A 90 µL (or appropriate volume to give final volume of 100 µL) of a buffer mixture containing Tris-acetate buffer (pH 7.75), ATP, magnesium acetate$_2$ and D-luciferin (Sigma) was added to the lysate to give the respective final concentrations of 25 mM, 2 mM, 4 mM and 0.4 mM. Alternatively, 100 µL of commercially available luciferase assay reagent (Promega) was prepared by mixing 10 mL of luciferase assay buffer to the vial containing the lyophilized luciferase assay substrate, was added to 20 µL of the specified cell lysate. Total light output was measured using the Wallac1420 Victor 2 luminometer (Perkin-Elmer) flash kinetics mode. The integration time was set to 0.5 s and the number of repeats set as 100.

Example 7

*Arachnocampa* Luciferase Activity

Figure 16:
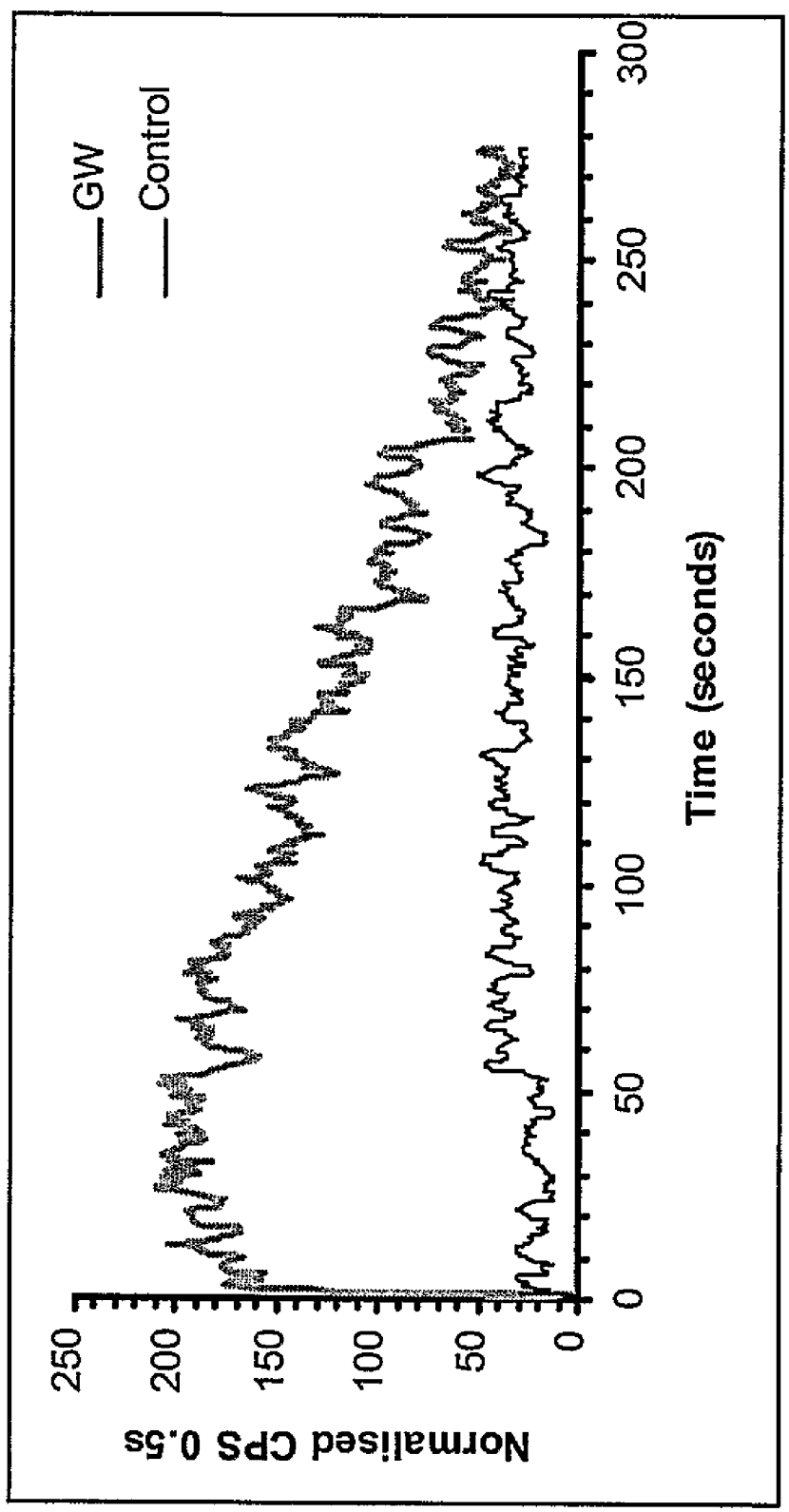
FIG. 16 Enhancement of bioluminescence by luciferases of the invention.
Figure 17:
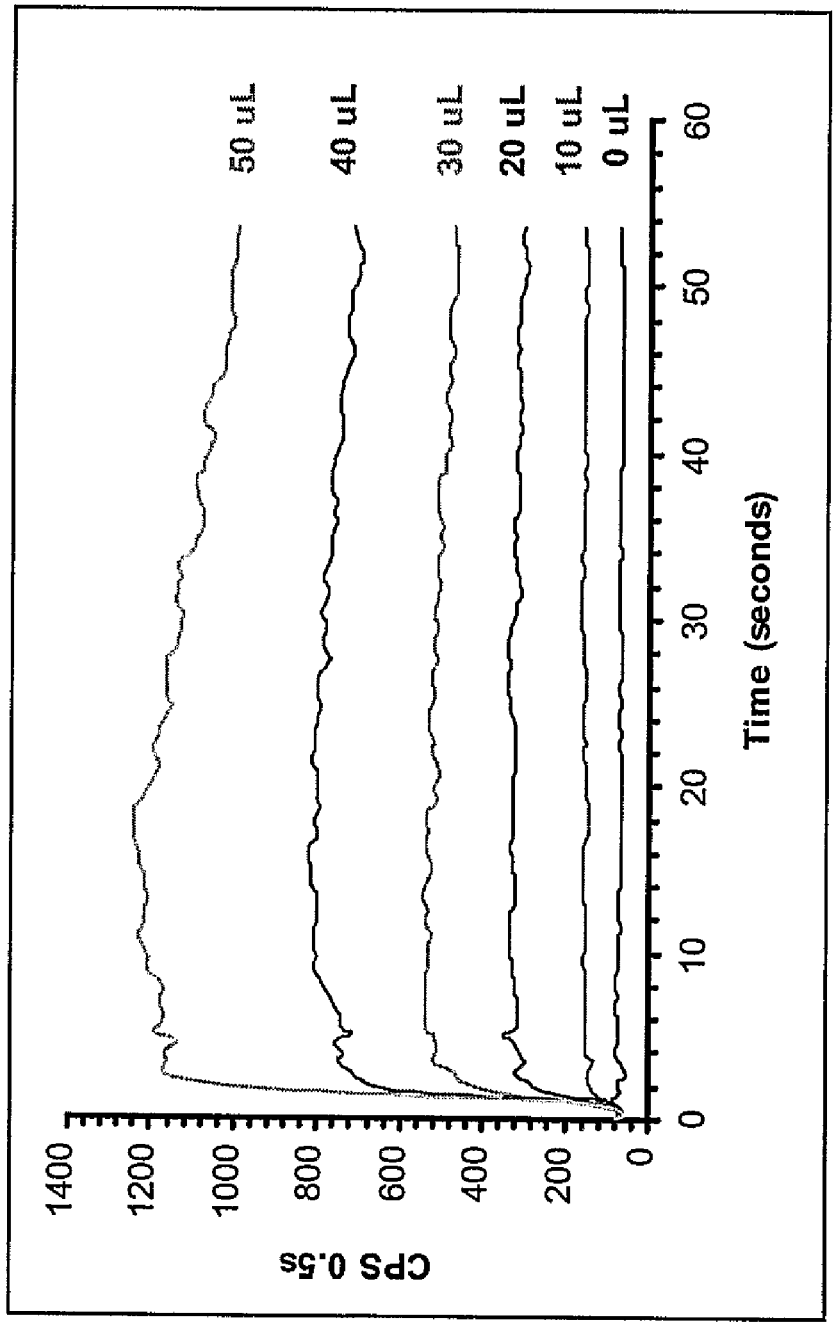
FIG. 17 Quantitative response of bioluminescence by increasing amounts of luciferases of the invention.
Figure 18:
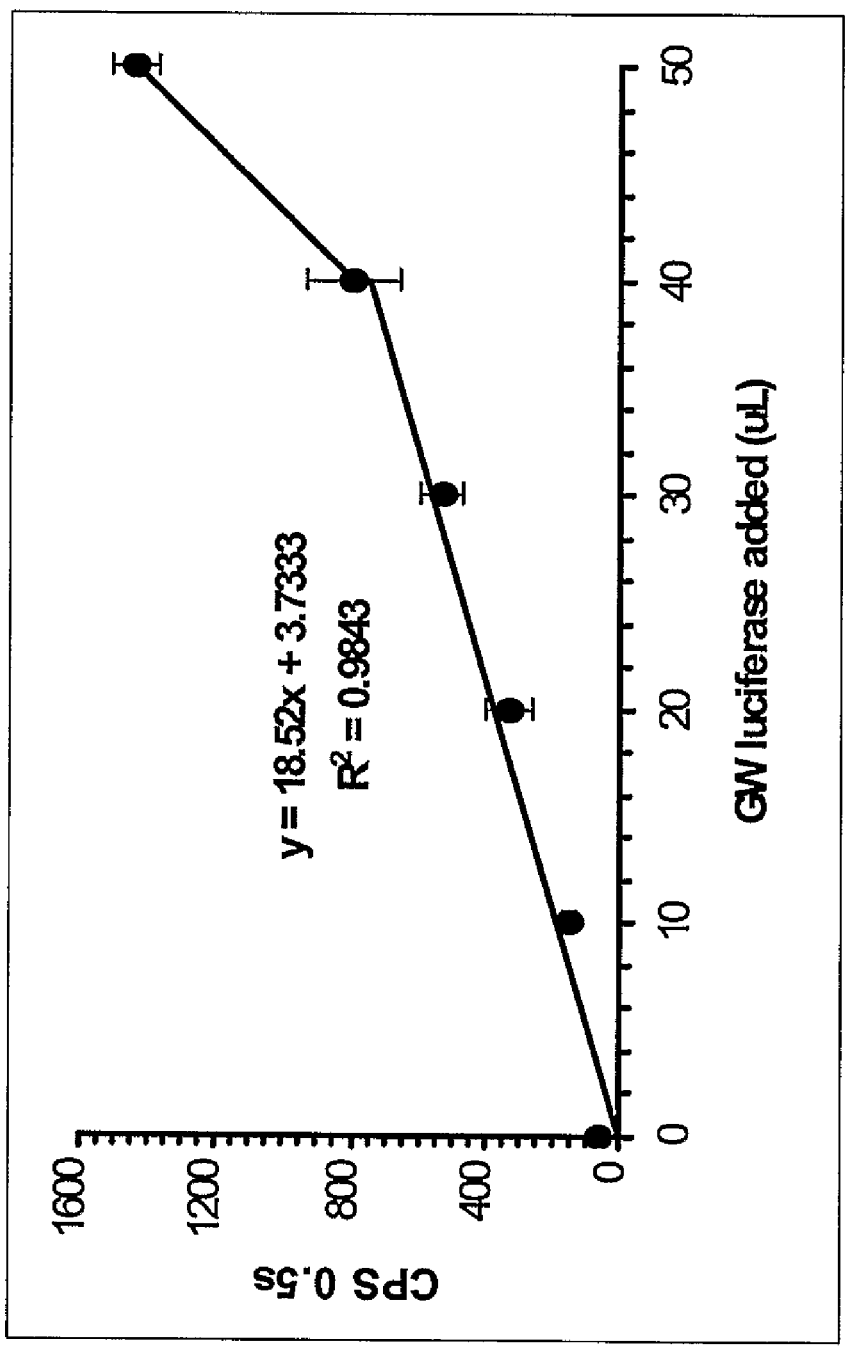
FIG. 18 Calibration plot.

Addition of D-luciferin to a 10 µL cell lysate of *Arachnocampa* derived luciferase ("glow worm luciferase" or "OW luciferase") resulted in enhancement of the bioluminescent activity compared to that of the control cell lysate (FIG. 16). It has been reported that absolutely no cross-reactivity exists between the beetle bioluminescent system and the *Arachnocampa* bioluminescent system. Different and increasing amounts of GW luciferase were added to D-luciferin and demonstrate that this response was quantitative (FIG. 17). In all cases care was taken to ensure there was no cross-talk between wells by spacing the used wells apart. The GW luciferase present in the lysate mixture could be quantified using beetle D-luciferin (sensitivity was 18.52 CPS/µL GW luciferase lysate added) (FIG. 18). The assay is sensitive enough to quantify glow-worm luciferase prepared in the manner described.

Controls

Figure 19:
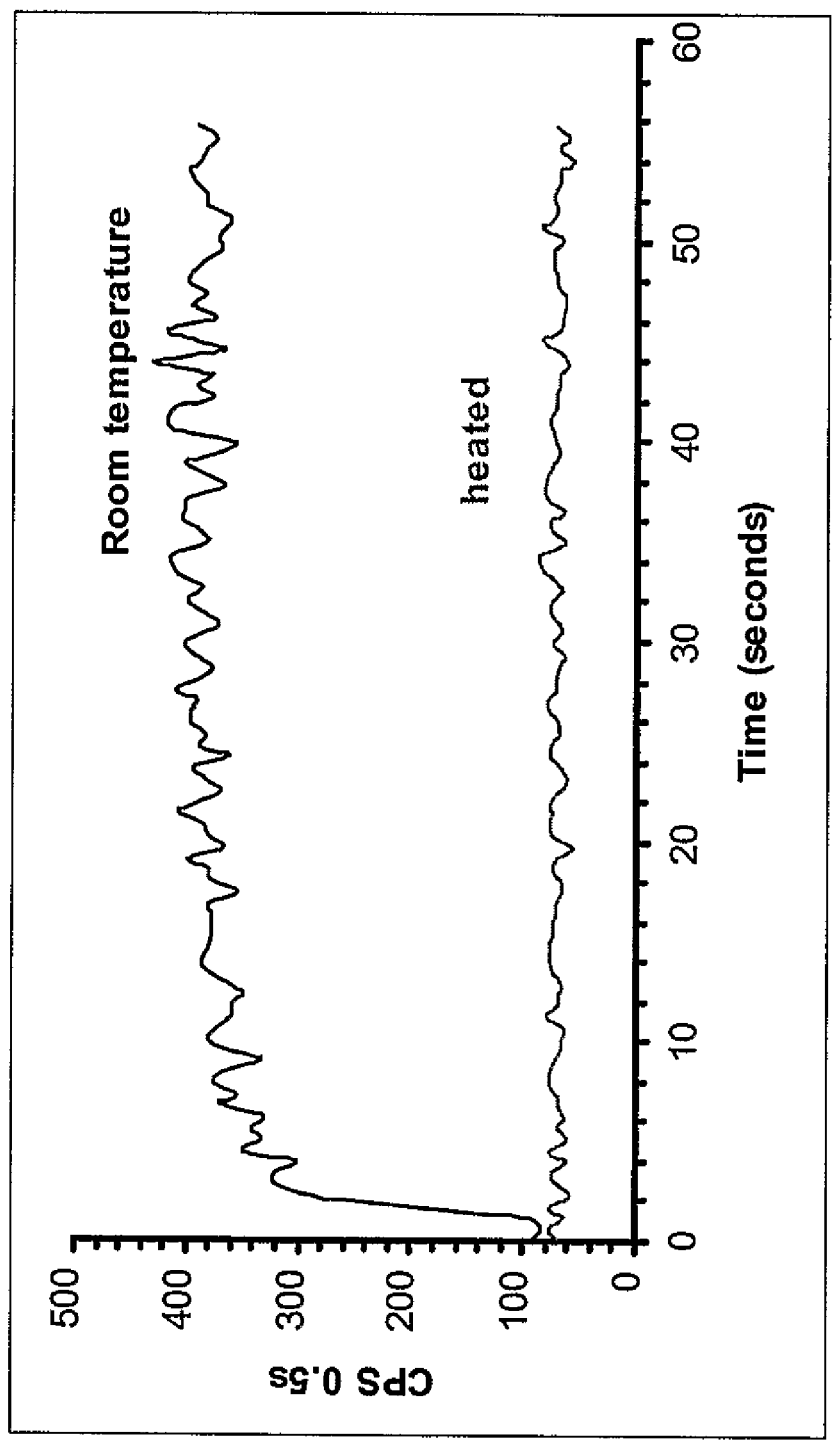
FIG. 19 Heat denaturation eliminates bioluminescence activity.

To ensure that the bioluminescent enhancement observed was due to the interaction of GW luciferase with D-luciferin a number of control experiments were carried out. The first control experiment simply involved heating the GW luciferase cell lysate for 5 minutes at 95° C. prior to mixing with D-luciferin. Heating the GW luciferase containing cell lysate prior to the addition of D-luciferin completely abolished the bioluminescent enhancement (FIG. 19).

Figure 20:
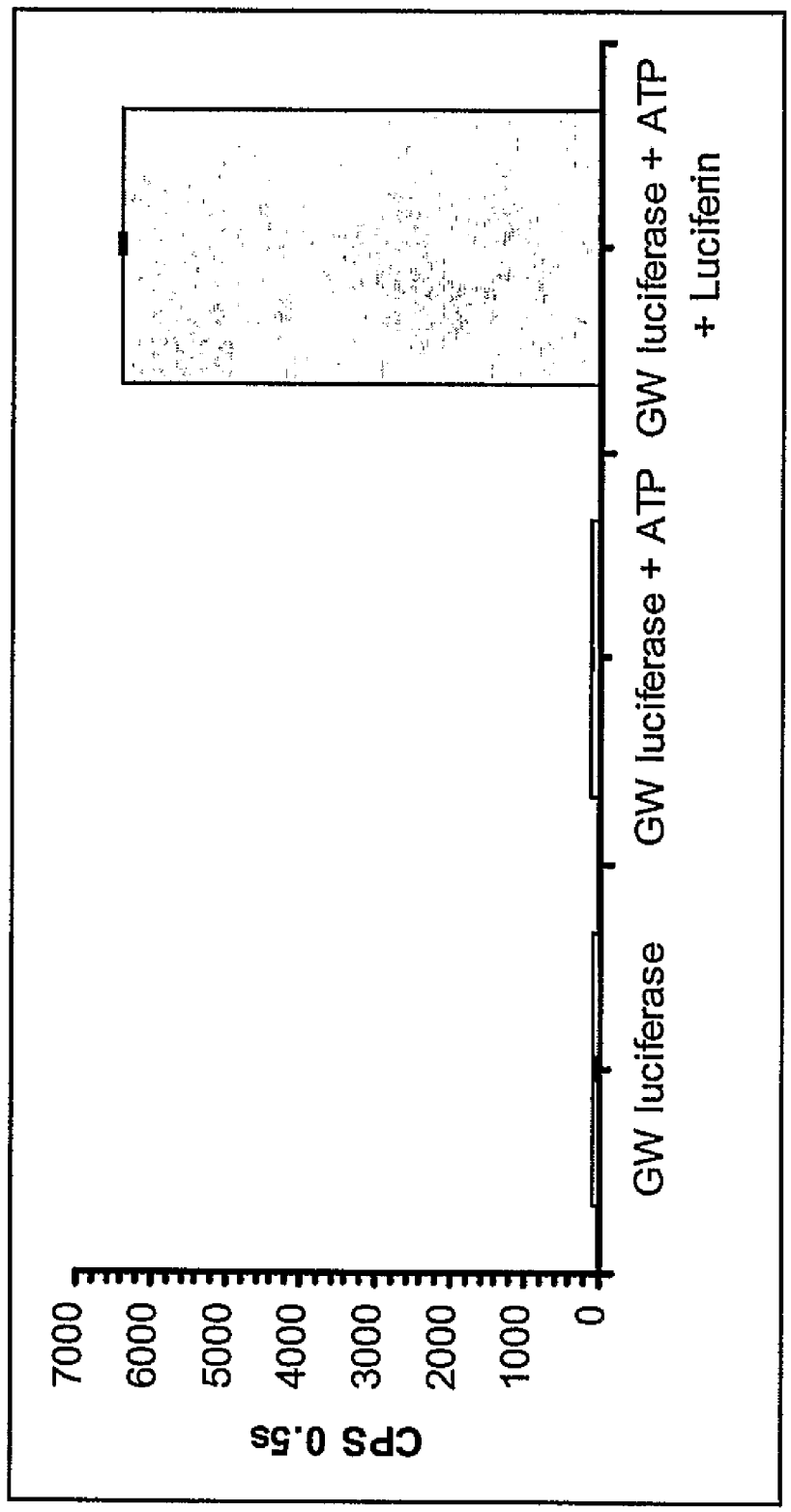
FIG. 20 Bioluminescence is dependent upon luciferin and ATP.

The second control looked at the response of the GW luciferase to ATP/Mg (2 mM and 4 mM concentrations, respectively). FIG. 20 shows the response of 50 µL of GW luciferase lysate to the addition of ATP/Mg with and without the simultaneous addition of D-luciferin. Enhancement in bioluminescence is not caused by ATP or Mg but by the presence of D-Luciferin.

Figure 21:
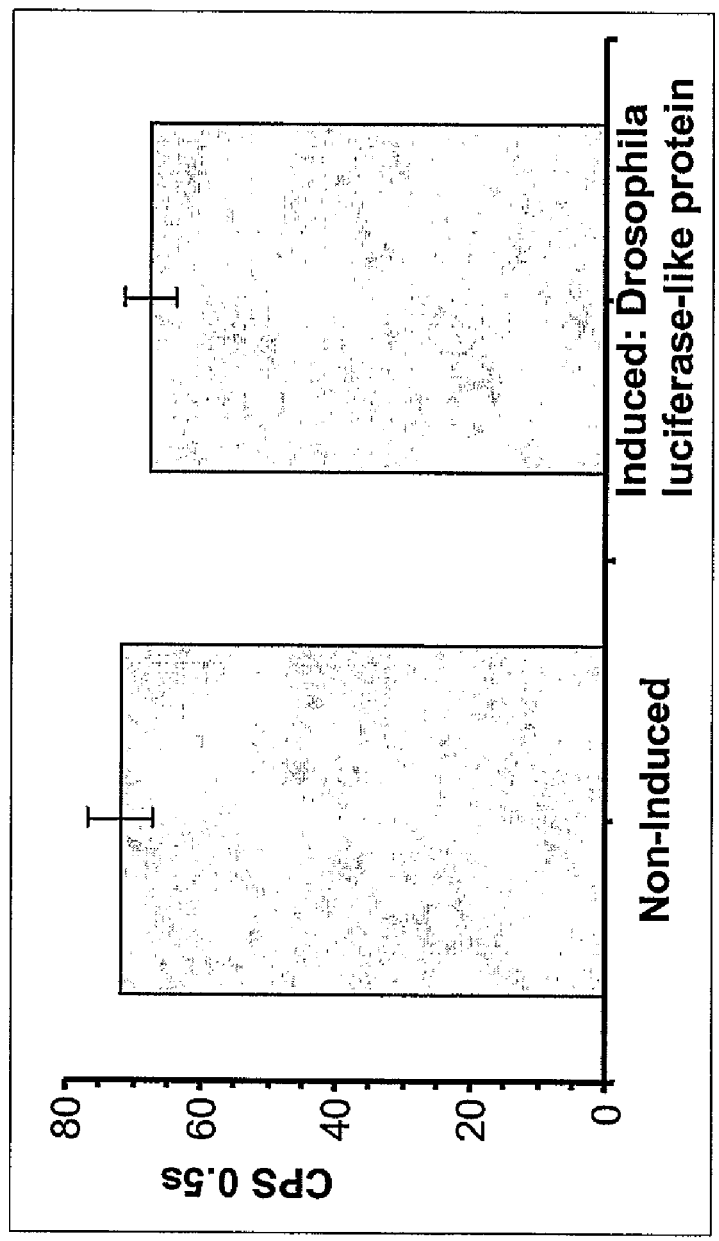
FIG. 21 Bioluminescence activity is specific to peptides of the invention.
Figure 22:
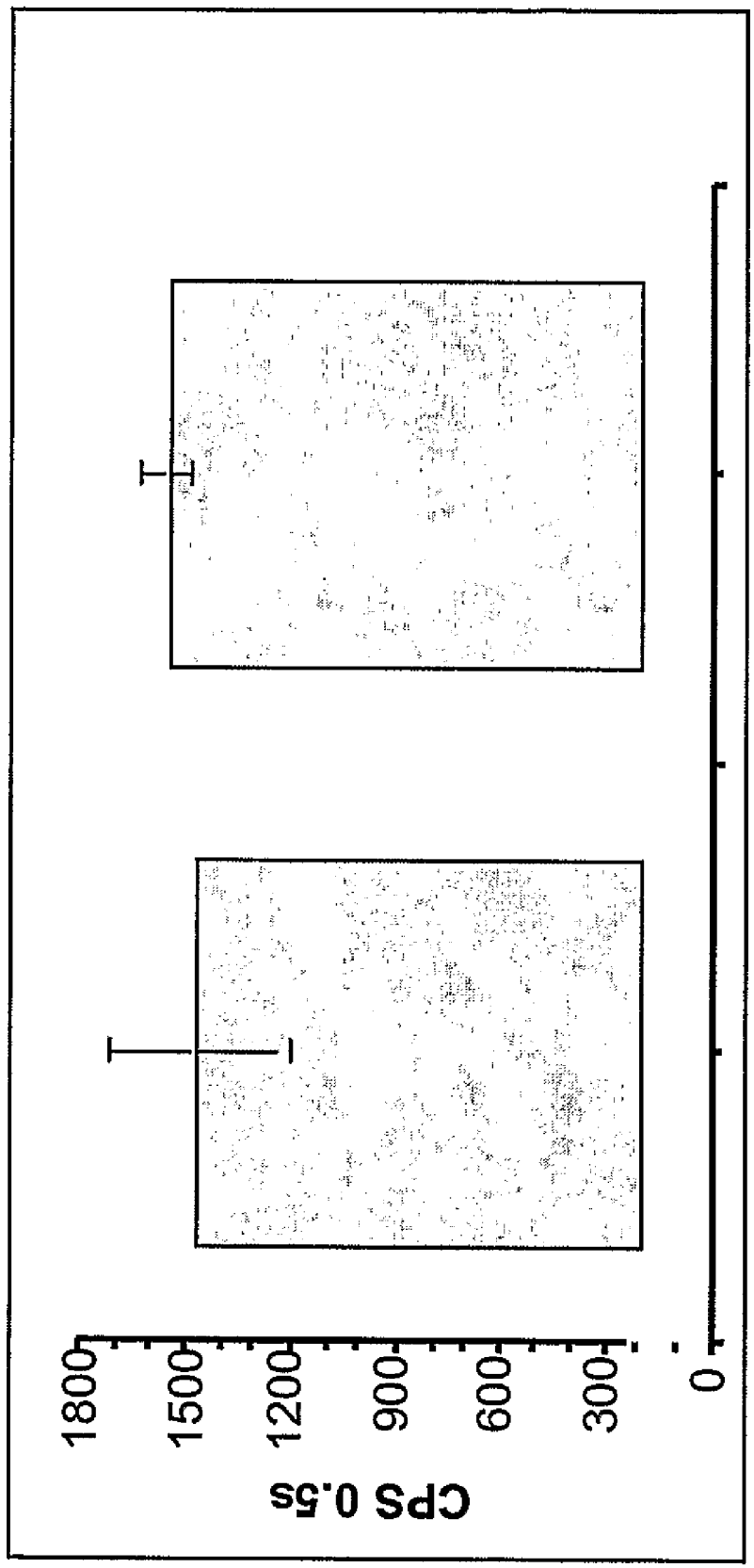
FIG. 22 Peptides of the invention do not utilize coelenterazine as substrate.

Further controls were carried out using a different luciferase with D-luciferin and a different substrate with GW luciferase. Replacing GW luciferase with an IPTG induced *drosophilia*-like luciferase did not result in any significant enhancement of the bioluminescence upon addition of D-luciferin compared to a non-induced cell lysate (FIG. 21). Replacement of D-luciferin with the most bioluminescent efficient coelentarazine substrate (CLZN-hcp (1µ/100 µl) did not result in any bioluminescent enhancement upon addition with GW luciferase compared to that of a control cell lysate (FIG. 22).

The bioluminescent enhancement reaction observed upon mixing of GW luciferase and D-luciferin is due to a specific interaction involving these two components in the presence of ATP.

Example 8

*Arachnocampa Richardsae* Bioluminescence System

Crude Extract Preparation: Method 1

This method was adapted from that described by Viviani et al. (2002). Crude extracts of *Arachnocampa* were prepared by homogenising 5 light organs in 0.5 mL of cold extraction buffer (27 mM Tricine, 7 mM MgSO$_4$, 0.2 mM EDTA, 10% glycerol and 1% TRITON-X-100™, pH 7.4. After homogenisation the extracts were centrifuged at 15,000 g for 15 minutes at 4° C. The hot extract was prepared by heating the supernatant at 98° C. for five minutes and adding 1 mM ATP (final concentration). Luciferase activity was determined by mixing 10 µL of hot extract with 90 µL of reaction buffer solution containing 0.84 mL of Tris-HCl buffer (pH 8), 0.11 mL of either glow-worm of firefly luciferase and 0.05 mL of ATP/Mg (40/80 mM).

Crude Extract Preparation: Method 2

In the second method the crude extract was prepared by adding 100 µL of ethyl acetate to five frozen light organs in an eppendorf tube and following homogenisation the extracts were centrifuged at 15,000 g for 5 minutes. The eppendorf containing the light organs was kept on dry ice whilst the homogenisation process was carried out. In Vitro bioluminescence assays were carried out by mixing 20 µL of crude extract with reaction buffer solution containing tris-acetate buffer (25 mM), magnesium actetate (4 mM) and ATP (2 mM) (all final concentrations) to give a final volume of 100 µL.

GW Luciferase Assay.

Reaction buffer containing tris-acetate buffer (25 mM), magnesium actetate (4 mM), ATP (2 mM) (all final concentrations) and GW luciferase cell lysate to give a final volume of 100 µl were added to 20 µL of crude extract.

Crude Extract Activity

Initial investigations trying to replicate the hot-cold extract experiments with GW luciferase described by Viviani et al. (2002) were unsuccessful. Addition of GW luciferase, without the simultaneous addition of ATP, to crude extract samples prepared as described resulted in a flash of bioluminescent activity. This effect was repeatable upon the further addition of GW luciferase with the simultaneous addition of ATP. This type of flash is characteristic of the type of flash usually seen upon the addition of excessive luciferase and ATP to D-luciferin.

Luminescence Spectra

Following the positive demonstration of the GW luciferase activity in the presence of D-luciferin the fluorescence and bioluminescence spectra of both the GW and FF luciferases upon the addition of D-luciferin were recorded.

Solution Preparation. A 0.5 mL solution was prepared by mixing 450 µL of assay buffer solution or the commercial assay reagent (Promega), with 50 µL of the corresponding luciferase as indicated. The mixing was carried out in a 1 mL fluorimeter cuvette and the spectra recorded by a Cary Eclipse fluorescence fluorimeter using the wavelength scan mode. The bioluminescence spectra were recorded immediately after mixing of the solutions and the fluorescence spectra were recorded before and after addition of the respective luciferase, as indicated.

Bioluminescence Spectra

Figure 23:
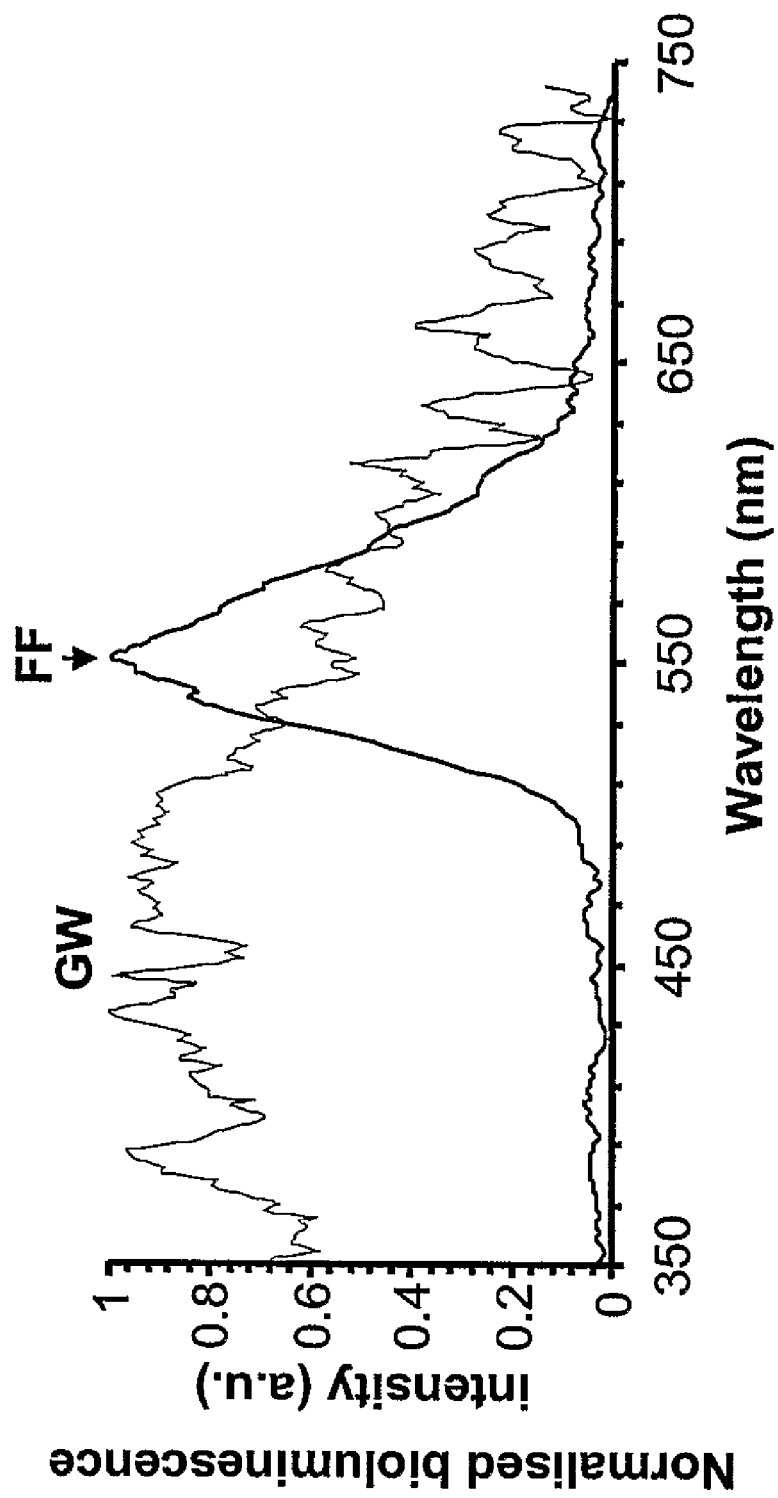
FIG. 23 Maximum bioluminescence produced by peptides of the invention occurs at less than 530±5 nm wavelengths.

The normalised bioluminescent spectra of both GW (*Arachnocampa*) and FF (firefly, *Photinus*) luciferase upon the addition of D-luciferin are shown in FIG. 23. The maximum bioluminescence induced by the GW luciferase addition lies between 440 and 480 nm. Use of GW luciferase in place of FF luciferase results in a hypsochromic shift in the emission spectra from 555 nm to below 530 nm. The reported maxima for FF luciferase is 562 nm at pH 7.6. The maximum intensities of the spectra varied considerably being 90.98 arbitrary units (a.u.) and 3.12 a.u. for FF and GW luciferases, respectively.

Example 9

Isolation of Homologous Luciferases from Other *Arachnocampa* Species

As reviewed in Baker (2004), for a number of years, four Australasian species of luminescent *Arachnocampa* were recognised. These were *Arachnocampa flava*, *Arachnocampa richardsae*, *Arachnocampa tasmaniensis* and *Arachnocampa luminosa*, which is endemic to New Zealand. The first pair of species is assigned to sub-genus *Campara* and the latter pair to sub-genus *Arachnocampa*. In her doctoral research Baker (op cit.) obtained convincing evidence that the Australasian bioluminescent *Diptera* are represented by at least nine biological species. In addition to the four species already mentioned, Baker (op. cit.) described five new Australian species, namely: *Arachnocampa buffaloensis*, *Arachnnocampa tropicus*, *Arachnocampa girraweenensis*, *Arachnocampa gippslandensis* and *Arachnocampa otwayensis*. Apart from *Arachnocampa* spp. and the North American *Orfelia fultoni* (Fulton, 1941; Viviani, 2002), there have been occasional reports of other luminescent species of *Diptera*, generally *Keroplatus* spp. (e.g. summarised in Sivinski, 1998; Baker, 2004). These reports are generally poorly documented and relate to species that usually are not found in the locally abundant aggregations characteristic of the Australasian fauna. We set out to demonstrate the viability of isolating sequences encoding luciferases from other bioluminescent *Diptera*, using the sequence of *A. richardsae* to design PCR primers and some, readily available, Australian species of *Arachnocampa* as examples.

Methods and Results

Homologues of the *A. richardsae* luciferase gene from three other species of *Arachnocampa* were isolated, cloned and sequenced. The three species were *Arachnocampa flava* and *Arachnocampa girraweenensis* of subgenus *Campara*, and *Arachnocampa tasmaniensis* of subgenus *Arachnocampa*. For each of these species, two to five larval specimens were collected from their native habitats, and transferred alive to the laboratory within 24 hours. Specimens of each species were dissected under phosphate- or tris-buffered saline. Excised light organs, with some surrounding tissues attached, were pooled and snap-frozen at −80 OC.

A. RNA Extraction

For each of the three species, total RNA from two or three light organs was extracted using the RNAqueous-Micro Kit (Ambion, cat. no. 1931), following the manufacturer's instructions.

B. cDNA Synthesis

1. First strand cDNA synthesis: Single stranded cDNA was synthesised using primers from the Creator SMART cDNA Library Construction Kit (Clontech/BD Biosciences, cat. no. K1053-1). Reactions were performed following the manufacturer's instructions. Reverse Transcriptase provided in the kit was directly substituted with fresh PowerScript Reverse Transcriptase (BD Biosciences, cat. no. 639500).

2. Second strand cDNA synthesis: Double stranded (ds) cDNA was synthesised by Long Distance PCR, using the primers provided with the Creator SMART cDNA Library Construction Kit. Using 2 μL of the first strand cDNA, synthesised as described in the preceding section, 25 thermal cycles of amplification were performed, following the kit instructions. DNA Polymerase in the kit was directly substituted with fresh Advantage cDNA Polymerase Mix (BD Biosciences, cat. no. 50595).

C. Cloning Luciferase cDNAs by PCR

1. *A. flava* and *A. girraweenensis*

Portions of the *A. flava* and *A. girraweenensis* luciferase cDNAs were amplified from their respective ds cDNA pools. PCR reactions were performed using HotStarTaq DNA Polymerase (Qiagen, cat. no. 203203), with PCR primers designed to complement the *A. richardsae* luciferase gene (Table 6).

TABLE 6

Sequences of *A. richardsae* luciferase cDNA primers mentioned in the text and Table 7.

| Primer name | | Primer sequence | SEQ ID NO: |
|---|---|---|---|
| F1 | GWLO8F5F250 | 5'-AGAAAGGGCGATCGTGTTG-3' | 17 |
| F2 | GWLucScreenU | 5'-GATGATAATGCACCAGAAAAG-3' | 18 |
| F3 | GWLO91E1F250 | 5'-ACCATTGCCACTGTTTTATTGA-3' | 19 |
| F4 | GWLO91B6F12 | 5'-CATTTAATGGCACCAGGGTACT-3' | 20 |
| F5 | GWLO91F7F228 | 5'-ACCCGAAATTGCGAACTATGA-3' | 21 |
| R5 | GWLucRS873 | 5'-AGTAAAACCAAACGCATTAG-3' | 22 |
| R6 | GWLucRS757 | 5'-AAGGGAGGGTGAACACTGA-3' | 23 |
| R7 | GWLucRS601 | 5'-CCATAAAATTGACGTACGACC-3' | 24 |
| R8 | GWLucRS484 | 5'-CCAAGAAGGGCACCAGTTT-3' | 25 |
| R9 | GWLucScreenL | 5'-TTATAATATCCAGCATCACCA-3' | 26 |
| R10 | GWLucRS326 | 5'-CAACGAACCATTCAAATCT-3' | 27 |
| R11 | GWLucRS182 | 5'-AATGCAAATAATACTTCACCACC-3' | 28 |
| R12 | GWLucRS90 | 5'-GCCACCTTTAAGATGCTTG-3' | 29 |
| R13 | GWLucRS42 | 5'-AACATTTTGCCAGCTGGATTC-3' | 30 |

For *A. flava*, 30 combinations of primer pairs were tested (Table 7), and 40 thermal cycles of amplification were performed following the manufacturer's instructions. Twenty-nine of the 30 primer pair combinations amplified unique products of the expected size. Two PCR products (Table 7) were purified with microCLEAN DNA Clean up reagent (Astral, cat. no. 2MCL-5) and sequenced with primers specific for the *A. richardsae* luciferase cDNA sequence. A BESTFIT comparison showed the *A. flava* nucleotide sequence was 96% identical to the previously determined cDNA sequence of *A. richardsae* luciferase. This confirmed the identity of the *A. flava* sequence as a homologue of the *A. richardsae* luciferase.

For *A. girraweenensis*, only four combinations of the *A. richardsae* luciferase gene specific primers were tested (Table 7) using the same PCR conditions as described in the preceding section. All four primer pair combinations amplified unique products of the expected size. Two PCR products (Table 7) were purified and sequenced with *A. richardsae* luciferase cDNA sequence specific primers. A BESTFIT comparison showed the *A. girraweenensis* nucleotide sequence was 96.5% identical to the previously determined cDNA sequence of *A. richardsae* luciferase. This confirmed the identity of the *A. girraweenensis* sequence as a homologue of the *A. richardsae* luciferase.

The 5' and 3' ends of the *A. flava* and *A. girraweenensis* luciferase cDNAs were amplified separately by semi-anchored PCR: each primer pair included an *A. richardsae* luciferase cDNA sequence specific primer, and a second primer that complemented a portion of the SMART primer used in the cDNA synthesis of *A. flava* and *A. girraweenensis* ds cDNA (Table 8). Double stranded cDNA was used as template and touchdown PCR reactions were performed with Pfx50 DNA Polymerase and 40 thermal cycles of amplification, following the manufacturer's instructions.

For the 5' end amplification, two combinations of primer pairs were tested with both species (Table 9). Both primer pairs amplified unique products of the expected size for both *A. flava* and *A. girraweenensis* (Table 9).

For the 3' end amplification, two combinations of primer pairs were tested for both species (Table 10). Both primer pairs amplified unique products of the expected size for both *A. flava* and *A. girraweenensis* (Table 10). For both species, one product from each 3' and 5' end amplification was sequenced, which revealed the sequence of both the 5' end and the 3' end of the luciferase cDNA. For both *A. flava* and *A. girraweenensis* luciferase genes, the first 40 nucleotides and the last 40 nucleotides of the ORF were identical to those of the *A. richardsae* luciferase cDNA ORF. The complete ORF for both *A. flava* and *A. girraweenensis* luciferase genes was amplified by touchdown PCR with the two primers pETG-WLucF and pETGWLucR, described in Virginia's expression section. The reactions were performed with single stranded cDNA as template and pfx50 DNA Polymerase (Invitrogen, cat. no. 12355-012) and amplified following the manufacturer's instructions. The 1.6 kb amplicons were sequenced in their entirety. The *A. flava* and *A. girraweenensis* luciferase peptide sequences were found to be 99.6% and 99.8% identical, respectively, to the luciferase gene from *A. richardsae*.

2. *A. tasmaniensis*

Both the 5' and 3' ends of the *A. tasmaniensis* luciferase cDNA were directly amplified by semi-anchored PCR. A number of primer pairs were tested for each end (Table 11; Table 12). Double stranded cDNA was used as template and touchdown PCR reactions were performed with Pfx50 DNA Polymerase and 40 thermal cycles of amplification, following the manufacturer's instructions.

For the amplification of the 5' end, six primer pair combinations were tested. Two of these amplified unique products of the expected size. One of the products (Table 11) was directly cloned into pJET1/blunt Cloning Vector (Fermentas, cat. no. K1221) following the manufacturer's instructions.

To amplify the 3' end, two primer pair combinations were tested. One pair (Table 12) amplified a unique product of the expected size, that was directly cloned into pJET1/blunt Cloning Vector. Four clones from each of the two cloned products were sequenced with pJET1 sequencing primers. A BESTFIT DNA sequence comparison to the *A. richardsae* luciferase cDNA showed 83% identity at the 5' end, and 88% identity at the 3' end. A BESTFIT peptide sequence comparison to the *A. richardsae* luciferase gene showed 89% identity and 93% identity at the 5' end and 3' end, respectively. These data confirmed that the two PCR amplicons were derived from a likely homologue of the *A. richardsae* luciferase cDNA. Both the beginning and end of the ORF had been identified. Primers were designed that were complementary to the start and end of the *A. tasmaniensis* luciferase ORF, in order to amplify the complete ORF:

A.tasLucORF-F:
5'-ATGACTTCTACATCTGTGGA-3';           (SEQ ID NO: 31)

A.tasLucORF-R:
5-TTACAATGTTGATCTTAAAATAC-3';        (SEQ ID NO: 32)

TABLE 7

*A. richardsae* cDNA primer combinations tested with *A. flava* ds cDNA

| Forward primer | Reverse primer | | | | | | | | |
|---|---|---|---|---|---|---|---|---|---|
| | R5 | R6 | R7 | R8 | R9 | R10 | R11 | R12 | R13 |
| F1 | Y | Y | Y | Y | Y | Y | Y | Y, 1.3 kb *g | Y, 1.3 kb #*f, g |
| F2 | — | — | Y | Y | Y | Y | Y | Y, 1.0 kb *g | Y, 1.1 kb #*f, g |
| F3 | — | — | — | Y | Y | Y | Y | Y | Y |
| F4 | — | — | — | — | N | Y | Y | Y | Y |
| F5 | — | — | — | — | — | — | Y | Y | Y |

Y: unique product of expected size amplified
N: no product of expected size amplified
—: primer combination not tested
*g: Primer combination also tested with *A. girraweenensis*, and unique product of expected size amplified
*f, g: *A. flava* and *A. girraweenensis* product sequenced

TABLE 8

Primer sequences used for amplification of 5' and 3' ends of luciferase cDNAs

| Primer Name | Primer sequence | SEQ ID NO: |
|---|---|---|
| #SMART-nF1 | 5'-AAGCAGTGGTATCAACGCAG-3' | 33 |
| #SMART-nF2 | 5'-CAACGCAGAGTGGCCATTA-3' | 34 |
| #CDSIII-R | 5'-ATTCTAGAGGCCGAGGCG-3' | 35 |
| *GWLucRS1120 | 5'-TGGCTTTTCTGGTGCATTATC-3' | 36 |
| *GWLucRS1000 | 5'-CCCGTAGTACCAGATGTCAA-3' | 37 |
| *GWLuc1E1R10 | 5'-CATGTCGGCTTCAGTCCA-3' | 38 |
| *GWLucRS757 | 5'-AAGGGAGGGTGAACACTGA-3' | 39 |
| *GWLO91G12F236 | 5'-TTGGTACACTTATGCCTGGA-3' | 40 |
| *GWLO91C5F84 | 5'-CAATCCTGAAGCCTCCAAA-3' | 41 |

SMART-derived primers
*A. richardsae* luciferase cDNA sequence primers

TABLE 9

Primer combinations tested for 5' end luciferase amplification from *A. flava* and *A. girraweenensis*

| | SMART-nF1 | SMART-nF2 |
|---|---|---|
| GWLucRS1120 | — | Y, 0.5 kb*f, g |
| GWLucRS1000 | Y | — |

Y: unique product of expected size amplified
—: primer combination not tested
*f, g: product sequenced, for both *A. flava* and *A. girraweenensis*

TABLE 10

Primer combinations tested for 3' end luciferase
amplification from A. flava and A. girraweenensis

|  | CDSIII-R |
| --- | --- |
| GWLO91C5F84 | Y, 0.5 kb*f, g |
| GWLO91G12F236 | Y |

Y: unique product of expected size amplified
*f, g: product sequenced, for both A. flava and A.girraweenensis

TABLE 11

Primer combinations tested for
amplification of 5' end of A. tasmaniensis luciferase

|  | SMART-nF1 | SMART-nF2 |
| --- | --- | --- |
| GWLucRS1120 | — | N |
| GWLucRS1000 | N | — |
| GWLuc1E1R10 | Y, 0.4 kb* | Y |
| GWLucRS757 | N | N |

Y: unique product of expected size amplified
N: no product of expected size amplified
—: primer combination not tested
*unique product cloned and sequenced

TABLE 12

Primer combinations tested for
amplification of 3' end of A. tasmaniensis luciferase

|  | CDSIII-R |
| --- | --- |
| GWLO91C5F84 | N |
| GWLO91G12F236 | Y, 0.6 kb* |

Y: unique product of expected size amplified
N: no product of expected size amplified
*unique product cloned and sequenced

TABLE 13

Pairwise comparison of amino acid identity/similarity for the four
Arachnocampa species

|  | A. richardsae | A. flava | A. girraweenensis | A. tasmaniensis |
| --- | --- | --- | --- | --- |
| A. richardsae | 100 | 99.6 | 96.8 | 91.5 |
| A. flava | 99.8 | 100 | 99.8 | 91.7 |
| A. girraweenensis | 100 | 99.8 | 100 | 91.7 |
| A. tasmaniensis | 94.7 | 94.9 | 94.7 | 100 |

Using the PCR approaches described in the preceding sections it was straightforward to isolate not only luciferase cDNAs from A. flava and A. girraweenensis, but also from A. tasmaniensis. Given the high levels of sequence homology we observed among species within sub-genus Campara, it would also be straightforward to use the techniques described herein to isolate luciferases from Arachnocampa (Campara) gippslandensis, Arachnocampa (Campara) otwayensis, Arachnocampa (Campara) tropicus and indeed any other species of genus Arachnocampa sub-genus Campara that may be described in the future. Furthermore we have demonstrated that, using PCR primers specific for A. richardsae it is possible without undue experimentation to isolate the luciferase from A. tasmaniensis. We would therefore conclude that it would be straightforward to recover homologous luciferases from other species classified in sub-genus Arachnocampa, including Arachnocampa luminosa and Arachnocampa buffaloensis and indeed any other species of genus Arachnocampa that may be described in the future. Of course it would be even more straightforward to use primers specific for the sequence of A. tasmaniensis luciferase to recover homologous luciferases from other species of the sub-genus Arachnocampa using the strategies and methods previously described. It was not necessary to resort to screening cDNA libraries in order to isolate the luciferases of A flava, A. girraweenenis or A tasmaniensis. However, the library screening approach, as described previously, would be a viable way of recovering homologous luciferases not only from other members of the genus Arachnocampa but also from other, more distantly related, blue-luminescing Diptera, such as Orfelia fultoni or Keroplatus spp.

Because we were readily able to isolate sequences encoding homologous luciferases from as few as two Arachnocampa spp. light organs, we are also confident that it would be possible, using the methods disclosed, to amplify and isolate a homologous luciferase from even a single specimen of a blue-luminescing dipteran, such as those species, mentioned by Sivinski (1998), for which only single specimens are ever encountered.

Example 10

Bacterial Expression of Glow Worm Luciferase:
Expression Vectors, Host Cells, Induction Regimes
and Fusion Tags Alternate induction regimes and expression constructs for the bacterial expression of GWLuc#1.

In an attempt to optimise the expression and subcellular partitioning of bacterially expressed GWLuc#1, the following variables of the induction regime were manipulated as described in the following section; (i) induction period, (ii) induction temperature, (iii) IPTG concentration and (iv) E. coli strain (Reviewed in Derewenda, 2004). A second strategy utilised was to create N-terminal fusions between the GWLuc#1 and the tags, thioredoxin (Trx; e.g. pET48b(+) expression vector) and NusA (e.g. pET50b(+) expression vector). These tags have been demonstrated to have positive effects on both protein expression and solubility (Reviewed in Hammarström, Hellgren, van den Berg, Berglund and Härd, 2002). An N-terminal 6His fusion construct with GWLuc#1 was also created to further demonstrate the ability to create GWLuc#1 fusion proteins. The His tag was chosen because it is amenable to purification using metal-ion chelate chromatography.

Analysis of the partitioning of bacterially expressed GWLuc#1 and FFLuc.

Frozen bacterial pellets were lysed with 100 µl freshly prepared lysis mix (1×Luciferase Cell Culture Lysis Reagent (CCLR), 1.25 mg ml-1 lysozyme). Following incubation at room temperature for 10 minutes, the lysate was centrifuged for 20 minutes at 16,000 g at room temperature. The supernatant was removed and to it 1× NuPAGE®Lauryl Dodecyl Sulphate Sample Buffer containing 50 mM DTT was added. The pellet was lysed by the addition of 1× NuPAGE® Lauryl Dodecyl Sulphate Sample Buffer containing 50 mM DTT and the chromosomal DNA sheared by passing the bacterial lysate through a 30 G needle several times. Supernatant and pellet samples were analysed using Invitrogen's NuPAGE® Novex Bis-Tris Gel system as described previously.

Alternate induction regimes for the bacterial expression of native GWLuc#1.

The pETDuet-1 constructs of native P. pyralis and A. richardsae luciferases expressed in the E. coli strain BL21(DE3), were subjected to alternate induction regimes. From the pre-induction cultures prepared as previously described, 5 ml aliquots were each transferred to 50 ml conical centrifuge tubes. Aliquots were either not induced (water added to an equivalent volume of 0.4 mM IPTG) or induced by the addition of IPTG to a final concentration of 0.1 mM, 0.2 mM or 0.4 mM. These cultures were incubated at either 10° C. or 20° C., 150 rpm for 24, 48 (10° C. and 20° C.) or 120 (10° C. only) hours, at which times the Abs600 nm of each culture was measured. Three or four 0.25-0.5 ml aliquots were removed from each culture and centrifuged at 10,000 g for 5 minutes at room temperature. The pellet was stored at −80° C. for protein analysis.

The pETDuet-1 constructs of native *P. pyralis* and *A. richardsae* luciferases were electroporated into the Rosetta-gami™ B(DE3) (Novagen) strain of *E. coli* as previously described for the DH5α and BL21(DE3) *E. coli* strains. The cultures were preinduced as previously described for pET-Duet-1:GWLuc#1 in BL21(DE3). Upon achieving an Abs600 nm of 0.6-1.0, 5 ml aliquots were each transferred to 50 ml conical centrifuge tubes. Aliquots were either not induced (water added to an equivalent volume of 0.4 mM IPTG) or induced by the addition of IPTG to a final concentration of 0.2 mM or 0.4 mM. These cultures were incubated at either 10° C. or 20° C., 150 rpm for 4 (20° C. only), 24, 48 (10° C. and 20° C.) or 120 (10° C. only) hours, at which times the Abs600 nm of each culture was measured. Three or four 0.25-0.5 ml aliquots were removed from each culture and centrifuged at 10,000 g for 5 minutes at room temperature. The pellet was stored at 80° C. for protein analysis.

Construction of an N-terminal 6His GWLuc#1 fusion protein in pETDuet-1.

The full length cDNA of GWLuc#1 was amplified for 20 cycles using Platinum Pfx DNA polymerase following the manufacturer's recommendations using 2 ng template and 10 pmol of the primers NHis-GWLuc#1 (5'-GAgaattcGAT-TGAGGGACGCATGGCTTGTACTTCAGT-3'; SEQ ID NO: 42) and pETGWLucR (5'-GACGACcctaggTTACAAT-GTTCCTCTTAAA-3'; SEQ ID NO: 16). These primers introduce EcoRI and AvrII restriction sites (lowercase letters) 5' and 3' of the full length *A. richardsae* luciferase cDNA. The purified product was A-tailed as described previously and ligated into pGEM T-easy. The constructs were electroporated into the DH5α strain of *E. coli* and were sequenced using the CEQ 2000 Dye Terminator Cycle Sequencing with Quick Start Kit and 50 fmol of plasmid DNA. The full length, error-free construct was excised with EcoRI (Fermentas) and AvrII and inserted into EcoRI/AvrII linearised pETDuet-1 and the resulting plasmid was designated pETDuet:NHis-GWLuc#1. These plasmids were electroporated into the BL21(DE3) strain of *E. coli* as previously described and sequenced.

Construction of pET-48b(+)AmpR:GWLuc#1 and pET-50b(+)AmpR:GWLuc#1.

Ampicillin resistance was conferred on the expression vectors, pET-48b(+) (Trx N-terminal tag) and pET-50b(+) (NusA N-terminal tag) (Novagen, EMD Biosciences), by inserting the ampicillin resistance gene from pTAL-Luc into the SphI restriction enzyme site present in each vector. The ampicillin resistance gene from pTAL-Luc (bp4148-3218 on the negative strand +10 bp immediately 5' and 3' to the gene) was amplified for 20 cycles using Platinum Pfx DNA polymerase following the manufacturer's recommendation, using 2 ng template and 10 pmol of the primers AmpRCasSphIF (5'-TAGCGAAgcatgcGGTCTGACAGTTACCAA-3'; SEQ ID NO: 43) and AmpRCasSphIR (5'-CGTAAGCgcat-gcTCTAAATACATTCAAATATG-3'; SEQ ID NO:44). Each primer introduced a SphI restriction enzyme site (lowercase letters) at the 5' and 3' end of the ampicillin resistance gene. The PCR product was purified using microCLEAN, digested with SphI (New England Biolabs) and purified again using microCLEAN. The SphI digested ampicillin resistance gene PCR product was ligated into dephosphorylated, SphI linearised pET-48b(+) or pET-50b(+), electroporated into the DH5α strain of *E. coli* and sequenced using the CEQ 2000 Dye Terminator Cycle Sequencing with Quick Start Kit and 25 fmol of plasmid DNA. The resulting plasmids were designated pET-48b(+)AmpR and pET-50b(+)AmpR respectively.

The full length cDNA of GWLuc#1 was amplified for 20 cycles using Platinum Pfx DNA polymerase following the manufacturer's recommendations using 2 ng template and 10 pmol of the primers GWLuc1FHRV3C (5'-gggacccATG-GCTTGTACTTCAG-3'; SEQ ID NO: 45) and pETGWLucR (5'-GACGACcctaggTTACAATGTTCCTCTTAAA-3'; SEQ ID NO: 16). These primers introduce SanDI and AvrII restriction sites (lowercase letters) 5' and 3' of the full length *A. richardsae* luciferase cDNA. The purified product was A-tailed as described previously and ligated into pGEM T-easy. The constructs were electroporated in to the DH5□ strain of *E. coli* and were sequenced using the CEQ 2000 Dye Terminator Cycle Sequencing with Quick Start Kit and 50 fmol of plasmid DNA. The full length, error-free construct was excised with SanDI (Stratagene, La Jolla Calif.) and AvrII and inserted into either SanDI/AvrII linearised pET-48b (+)AmpR or pET-50b(+)AmpR and the resulting plasmids were designated pET-48b(+)AmpR:GWLuc#1 and pET-50b (+)AmpR:GWLuc#1 respectively. These plasmids were electroporated in to the BL21(DE3) strain of *E. coli* as previously described and sequenced. An error free construct of each expression vector; pET-48b(+)AmpR, pET 48b(+)AmpR: GWLuc#1, pET-50b(+)AmpR and pET-50b(+)AmpR: GWLuc#1, was electroporated in to the Rosetta-gami™ B(DE3) strain of *E. coli*.

Induction regimes for pETDuet:NHis-GWLuc#1, pET-48b(+)AmpR:GWLuc#1 and pET-50b(+)AmpR:GWLuc#1.

Preinduction cultures of pETDuet-1:NHis-GWLuc#1 in BL21(DE3) were as previously described for pETDuet-1: GWLuc#1 in BL21(DE3). Aliquots (10 ml) were either not induced (water added to an equivalent volume of 0.4 mM IPTG) or induced by the addition of IPTG to a final concentration of 0.4 mM. These cultures were incubated at either 20° C. or 37° C., 150 rpm for 1, 2, 3, 5 and 24 hours at 37° C. or 2, 5, 24, 30 and 48 hours at 20° C., at which times the Abs600 nm of each culture was measured. Five 0.5 ml and three 1.5 ml aliquots were removed from each culture and centrifuged at 10,000 g for 5 minutes at room temperature. The pellet was stored at 80° C. for protein analysis.

Preinduction cultures of pET-48b(+)AmpR, pET-48b(+) AmpR:GWLuc#1, pET-50b(+)AmpR and pET-50b(+) AmpR:GWLuc#1 in Rosetta-gami™ B(DE3) are as previously described for pETDuet-1:GWLuc#1 in BL21(DE3). Upon achieving an Abs600 nm of 0.6-1.0, 5 ml aliquots from each preinduction culture were transferred to 50 ml conical centrifuge tubes. Aliquots were either not induced (water added to an equivalent volume of 0.4 mM IPTG) or induced by the addition of IPTG to a final concentration of 0.1 mM, 0.2 mM or 0.4 mM. These cultures were incubated at either 10° C. or 20° C., 150 rpm for 24 or 48 hours, at which times the Abs600 nm of each culture was measured. Four or five 0.20-1.0 ml aliquots were removed from each culture and centrifuged at 10,000 g for 5 minutes at room temperature. The pellet was stored at 80° C. for protein analysis.

Bioluminescent assays of GWLuc#1 bacterially expressed with alternative induction regimes and expression constructs.

The bioluminescent assays were carried out as described previously by adding either 100 μL of Promega reagent buffer to 20 μL cell lysate or home-made buffer to cell lysate samples. Bioluminescence was recorded with either the Wallac1420 Victor 2 luminometer (Perkin-Elmer) using flash kinetics mode (integration time=0.5 s and the no. of repeats=100) or a POLARstar OPTIMA (BMG) operated in bioluminescence mode (interval time=0.2 s, gain for PMT=4095, no. of intervals=200, normalization time=0.5 s).

Results.

Both native luciferases were bacterially expressed under a range of induction regimes. Trx and NusA N-terminal GWLuc#1 fusion constructs were successfully expressed in the Rosetta-gami™ B(DE3) *E. coli* strain and the 6His N-terminal GWLuc#1 fusion construct was successfully expressed in BL21(DE3) as early as one hour at 37° C. and two hours at 20° C.

Expressed *A. richardsae* luciferase in Rosetta-gami™ B(DE3) *E. coli* strain with pETDuet-1 construct induced under alternative regimes was assayed to determine the bioluminescence activity upon the addition of home-made buffer. The most active cell lysates were produced by incubating the cultures for 48 hours at 20 oC when compared to samples prepared from cultures which had been incubated at 10 oC or 20 oC for 24 hours. If the bioluminescent activity of *A. richardsae* luciferase expressed in Rosetta-gami™ B(DE3) *E. coli* strain was compared to that expressed in the *E. coli* strain BL21(DE3) there was an enhancement by a factor of approximately two. It must be noted here that *A. richardsae* luciferase was expressed at a much higher level in *E. coli* BL21(DE3) than in Rosetta-gami™ B implying that the specific activity of the expressed luciferase protein is much higher in the Rosetta-gami™ B system. The thioredoxin and NusA. tagged *A. richardsae* luciferase expressed in Rosetta-gami™ B(DE3) *E. coli* strain did not produce any significant bioluminescent activity (P=0.05) compared to that of the control vector sample under any of the induction regimes described here.

The subcellular partitioning of the bacterially expressed native *P. pyralis* (FFLuc) and *A. richardsae* (GWLuc#1) luciferases was determined. Based on protein staining of gels FFLuc partitioned predominantly to the supernatant, with only a small amount being retained in the pellet fraction. The GWLuc#1 partitioned very differently, with a significant proportion partitioning to the pellet. Its presence was not observed in the supernatant based on protein staining of gels. Under no induction regime was the partitioning of the native *A. richardsae* luciferase observed to shift from the pellet to the supernatant fraction based on protein staining. This observation could explain why the sensitivity of bioluminescence measurements of FFLuc ('Firefly luciferase) was much greater than for GWLuc#1 upon addition of D-luciferin.

Example 11

Expression of *A. richardsae* Luciferase in the Eukaryote *Saccharomyces cerevisiae*

Construction of pYES2:GWLuc#1 for inducible expression in *Saccharomyces cerevisiae*.

The EcoRI fragment from the pGEM T-easy clone containing the full length, error-free cDNA construct of GWLuc#1, previously used and described, in the "Construction of pET-48b(+)AmpR:GWLuc#1 and pET-50b(+)AmpR: GWLuc#1", was excised and inserted into dephosphorylated, EcoRI linearised pYES2 (Invitrogen). This plasmid, designated pYES2:GWLuc#1, was electroporated into the DH5α strain of *E. coli*. Transformants containing the GWLuc#1 in the correct orientation were identified by standard PCR screening using the primers T7 (5'-TAATACGACTCACTAT-AGGG-3') and pETGWLucR. Plasmid DNA from both pYES2 and pYES2:GWLuc#1 was isolated using the QIAprep Spin Miniprep Kit (Qiagen) and 1 μg plasmid was used to transform the *S. cerevisiae* strain S288C (Invitrogen) using the Yeast Transformation Kit (Sigma). Yeast transformants were selected for uracil prototrophy by selection on Yeast Synthetic Drop-Out Media Supplement without Uracil (SCCM-U) (Sigma) supplemented with 2% (w/v) glucose (Sigma) for 48 hours at 30° C. The presence of the pYES2: GWLuc#1 was reconfirmed by extracting plasmid DNA using the Y-DER™Extraction Reagent Kit (Pierce, Rockford Ill.) and repeating the PCR screen described above using T7 and pETGWLucR.

Induction of pYES2:GWLuc#1.

Fifteen ml cultures of pYES2 in S288C and pYES2: GWLuc#1 in S288C in SCCM-U containing 2% (w/v) glucose were grown overnight at 28° C. with constant agitation. The Abs600 nm of each overnight culture was determined to calculate the culture volume required to obtain an $Abs_{600}nm$ of 0.5 in 5 ml. The required volume of each culture was removed and centrifuged for five minutes at 1500 g to pellet the cells. The pelleted yeast cells were resuspended in either 5 ml of non induction medium (SCCM-U containing 2% (w/v) raffinose (Sigma)) or induction medium (SCCM-U containing 2% (w/v) galactose (Sigma) and 2% (w/v) raffinose). The cultures were incubated at 28° C. for 24, 48 and 72 hours with constant agitation, and at the end of the incubation the Abs600 nm of each culture was measured. Aliquots (0.1-0.5 ml) were removed from each culture and centrifuged at 10,000 g for 5 minutes at room temperature. The pellet was stored at 80° C. for protein analysis.

Protein analysis of the *S. cerevisiae* expressed GWLuc#1 was performed as described with the following modification. The lysed samples were heated at 100° C. for five minutes due to the presence of the yeast cell wall.

Preparation of cell lysates for luciferase assay.

1× passive lysis buffer (Promega) was added to cell pellets to give a yeast cell number of $1.446 \times 10^7$ with calculations based on $Abs_{600}nm$ $1=3 \times 10^7$ cells/ml. The passive lysis buffer was added immediately prior the assay with a mixing time of approximately 15-20 s.

Bioluminescence assay of *A. richardsae* luciferase in *Saccharomyces cerevisiae*.

Following the addition of the lysis buffer 25 μL of the cell lysate mix was mixed with 75 μL of the home-made assay buffer and the light output monitored as a function of time with a Wallac1420 Victor 2 luminometer (Perkin-Elmer) as described previously.

Results.

Protein staining of the gels did not reveal any differences between the yeast strain(s) carrying the GWLuc#1 construct and those that did not. However, the pYES2 expression system, unlike the pET-*E. coli* expression system, is not an over-expression system. Further experiments to identify the *A. richardsae* luciferase protein were not pursued. Instead, luciferase assays were conducted to compare the strains(s) carrying GWLuc#1 and a control strain that did not. This is a much more sensitive method to screen for the presence of active luciferase than SDS-PAGE and protein staining.

Figure 24:
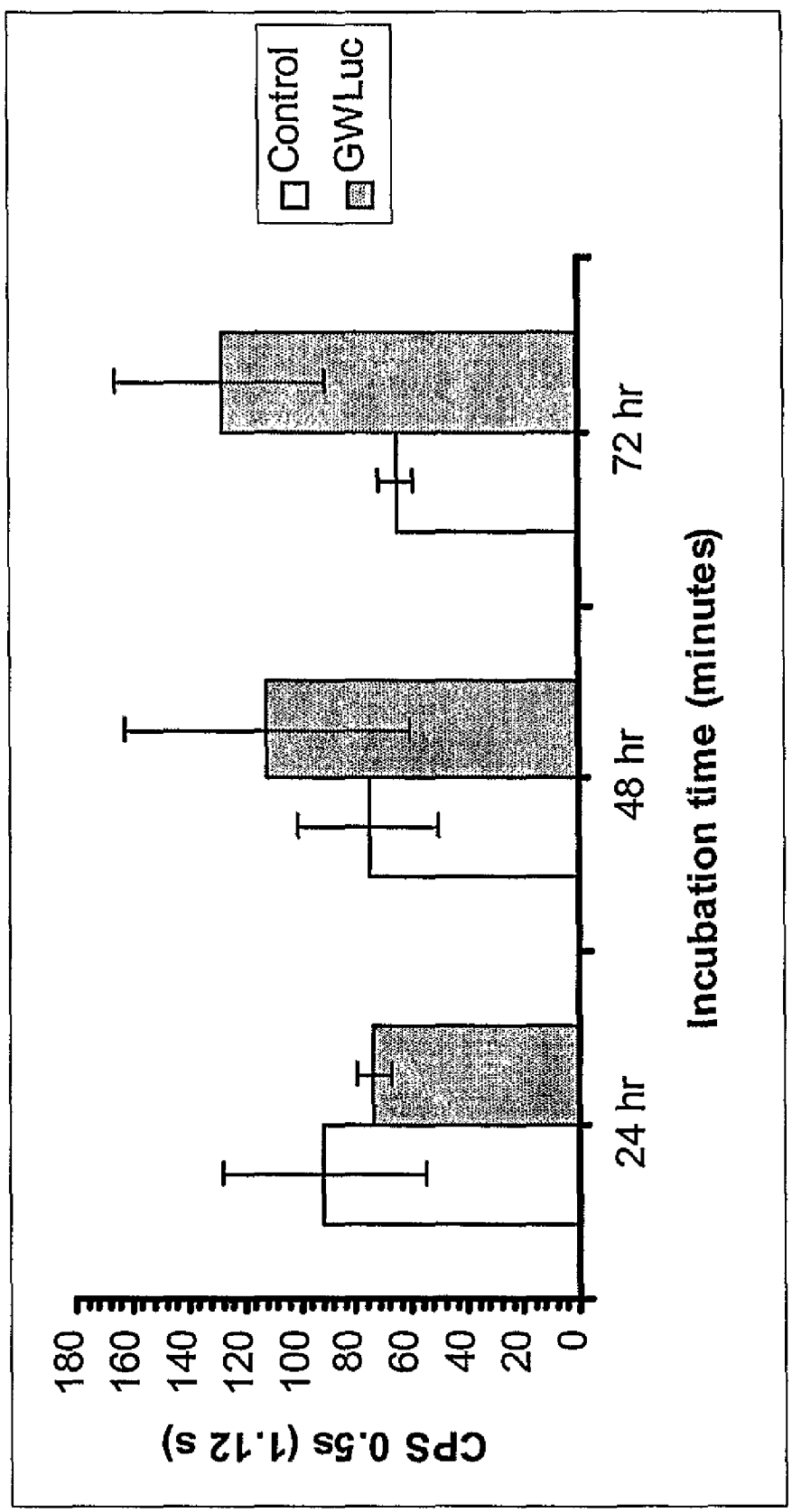
FIG. 24 Expression of bioluminescence activity of the invention in yeast.

The bioluminescence appeared as a short burst of activity as would be expected if low concentrations of any luciferase were assayed with a large excess of D-luciferin/ATP. FIG. 24 shows the bioluminescent intensity (CPS 0.5 s) of either GWLuc#1 or the control vector, measured 1.12 s after the recording began, prepared from cultures incubated at 28 degrees for 24, 48 or 72 hours. The greatest bioluminescent activity was achieved with cell lysates prepared from cultures incubated for 72 hours and the activity of GWLuc#1 was significantly higher (P=0.05) than that of the control sample. This indicates that GWLuc#1 was expressed successfully in S. cerevisiae and also exhibited appreciable activity. Although the bioluminescent intensity (CPS) is of a similar magnitude when A. richardsae luciferase is expressed in either E. coli strain BL21(DE3) or S. cerevisiae (FIG. 24) the expression level in the former is much higher than in the latter, suggesting that the specific activity of the expressed luciferase is much greater in S. cerevisia than in the BL21 (DE3) bacterial strain.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

REFERENCES

The following references, to the extent that they provide exemplary procedural or other details supplementary to those set forth herein, are specifically incorporated herein by reference.

U.S. Pat. No. 5,484,956
U.S. Pat. No. 5,538,879
U.S. Pat. No. 5,576,198
U.S. Pat. No. 5,595,896
U.S. Pat. No. 5,629,470
U.S. Pat. No. 5,633,155
U.S. Pat. No. 5,656,466
U.S. Pat. No. 5,670,356
U.S. Pat. No. 5,670,356
U.S. Pat. No. 5,674,731
U.S. Pat. No. 5,689,045
U.S. Pat. No. 5,689,049
U.S. Pat. No. 5,739,409
U.S. Pat. No. 5,744,320
U.S. Pat. No. 5,744,320
U.S. Pat. No. 5,750,870
U.S. Pat. No. 5,767,367
U.S. Pat. No. 5,807,522
U.S. Pat. No. 5,837,832
U.S. Pat. No. 6,068,979
U.S. Pat. No. 6,143,502
U.S. Pat. No. 6,171,809
U.S. Pat. No. 6,270,964
U.S. Pat. No. 6,297,018
U.S. Pat. No. 6,342,345
U.S. Pat. No. 6,503,723
U.S. Pat. No. 6,586,196
U.S. Pat. No. 6,602,657
U.S. Pat. No. 6,602,658
U.S. Pat. No. 6,690,461
U.S. Pat. No. 6,927,037
U.S. Patent Application 20030166905 (2003)
Adachi, J. Hasegawa, M. MOLPHY: programs for molecular phylogenetics, ver 2.3. Institute of Statistical Mathematics, Tokyo (1996).
Altschul, et al. J. Mol. Biol. 215:403-10 (1990)
Amann et al., Gene 69:301-315 (1988)
Angers, S., A. Salahpour, et al. Proc Natl Acad Sci USA 97(7): 3684-9 (2000).
Ausubel et al., "Current Protocols in Molecular Biology", John Wiley & Sons, (1998).
Baker, C. (2004). Australian glow-worms (Diptera: Keroplatidae: Arachnocampa spp.): distribution, diversity, identity and management. Ph. D. Thesis, Department of Zoology and Entomology, University of Queensland, Brisbane: 186 pp.
Baldari, et al, EMBO J. 6:229-234 (1987).
Berger, S. L. and A. R. Kimmel eds., 1987 "Methods in Enzymology: Guide to Molecular Cloning Techniques", Academic Press.
Bowie et al., Science 247:1306-1310 (1990).
Branchini, B. R., R. A. Magyar, et al. Biochemistry 37(44): 15311-9 (1998).
Branchini, B. R., R. A. Magyar, et al. Biochemistry 40(8): 2410-8 (2001).
Branchini, B. R., T. L. Southworth, et al. Biochemistry 42(35): 10429-36 (2003).
Conti et al. Acta Crystallogr D Biol Crystallogr. 1996 Jul. 1; 52(Pt 4):876-8.
Conti, E., N. P. Franks, et al. Structure 4(3): 287-298 (1996).
Creighton, T. E., Proteins—Structure and Molecular Properties, 2nd Ed., W. H. Freeman and Company, New York (1993).
Cunningham et al., Science 244:1081-1085 (1989)
Day, J. C., L. C. Tisi, et al., Luminescence 19(1): 8-20 (2004).
de Vos et al. Science 255:306-312 (1992)
de Wet, J. R., K. V. Wood, et al. Molecular and Cellular Biology 7(2): 725-37 (1987).
Derewenda, Z. S. (2004) Methods 34: 354-363.
Devereux, J., et al., Nucleic Acids Res. 12(1):387 (1984)
Elion E. A. (2003) Unit 3.17—Constructing recombinant DNA molecules by the polymerase chain reaction. In Ausubel F. M., Brent R., Kingston R. E., Moore D. D., Seidman J. G., Smith J. A. and Struhl K. (Eds) Current Protocols in Molecular Biology. John Wiley & Sons, Inc., USA.
Felsenstein, J. Cladistics 5: 164-166, 1989
Flanagan, W. M. et al. (1991) J. Virology: 65, 769-786
Fulton, B. B. Annals of the Entomological Society of America 34: 289-302 (1941).
Gottesman, S., Gene Expression Technology: Methods in Enzymology 185, Academic Press, San Diego, Calif. (1990)119-128)
Gribskov, M. and Devereux, J., eds., Sequence Analysis Primer, M Stockton Press, New York, 1991
Griffin, A. M., and Griffin, H. G., eds., Computer Analysis of Sequence Data, Part 1, Humana Press, New Jersey, 1994
Hammarström M., et al. (2002) Protein Science 11: 313-321.
Harlow, Antibodies, Cold Spring Harbor Press, (1989)
Harrison, R. A. Pacific Insects 8(4): 877-833 (1966).
Houghten et al., Nature 354:84-86 (1991)
Jain, V. K. and Magrath, I. T., BioTechniques: 12, 681-683 (1992)
Kaufman et al., EMBO J. 6:187-195 (1987)
Keown et al. (1990), Meth. Enzymol. 185:527-537.
Kozak, M., Cell 44(2): 283-92 (1986).
Kozak, M., Nucleic Acids Res 15(20): 8125-48 (1987).

Krause, M. H. and S. A. Aaronson, Methods in Enzymology, 200:546-556 (1991)
Kujan et al., Cell 30:933-943(1982)
Lam et al., Nature 354:82-84 (1991)
Leckie, F. et al. BioTechniques: 17, 52-57 (1994)
Lee, J. Photochemistry and Photobiology 24: 279-285 (1976).
Lesk, A. M., ed., Computational Molecular Biology, Oxford University Press, New York, 1988
Lockhart, D. J. et al., Nat. Biotech. 14: 1675-1680, 1996.
Lucklow et al., Virology 170:31-39 (1989)
Lundin, A. Methods Enzymol 305: 346-70 (2000).
Masuda et al., Gene 77, 265-270 (1989) and
Millican, D. S. and I. M. Bird, Anal Biochem 249(1): 114-7 (1997).
Nakatsu, T. et al. Nature 440:372-376 (2006).
Needleman and Wunsch (J. Mol. Biol. 48:444-453 (1970)
Nucleic Acids Res. 25(17):3389-3402 (1997)
Plant Biochemistry and Molecular Biology (eds. Lea & Leegood, John Wiley & Sons) (1993) pp 275-295.
Promega: Instructions for use of Products E2920, E2940, and E2980, revised 1/06, Part Number TM058. and Promega pGL3 Luciferase Reporter Vectors (available from Promega Corporation, Madison, Wis.)
Pugsley, C. W., New Zealand Entomologist 7(4): 419-424 (1983).
Rattan et al. (Ann. N.Y Acad. Sci. 663:48-62 (1992)
Sakurai, Y., R. Komatani, K. Tabata and H. Takaie On the glow-worm breeding at Tama Zoo
Sambrook et al., Molecular Cloning: A Laboratory Manual. 2nd. ed., Cold Spring Harbor Laboratory Press, Cold Spring Harbor, N.Y., (1989)
Schena, M. et al. (1996 Proc. Natl. Acad. Sci. 93: 10614-10619)
Schultz et al., Gene 54:113-123 (1987)
Seed, B. Nature 329:840(1987)
Seifter et al. (Meth. Enzymol. 182: 626-646 (1990)) and
Seliger, H. H. and W. D. McElroy, Arch Biochem Biophys 88: 136-41 (1960).
Shimomura, Johnson et al. 1966
Shimomura, O., F. H. Johnson, et al., Observations on the biochemistry of luminescence in the New Zealand glow-worm, *Arachnocampa luminosa*. Bioluminescence in Progress. F. H. Johnson and Y. Haneda. Princeton, Princeton University Press: 487-494 (1966).
Smith et al., Gene 67:31-40 (1988)
Smith et al., J. Mol. Biol. 224:899-904 (1992)
Smith et al., Mol. Cell Biol. 3:2156-2165 (1983)
Smith, D. W., ed., Biocomputing: Informatics and Genome Projects, Academic Press, New York, 1993
Songyang et al., Cell 72:767-778 (1993)
Studier et al., Gene Expression Technology: Methods in Enzymology 185:60-89 (1990)
Sivinski, J. M. (1998). Florida Entomologist 81(3): 282-292.
Takaie, H. (1989) Breeding and display of the glow-worms, *Arachnocampa* spp. Insectarium, vol.26 July: 214-219
Takaie, H. (1997) Ten years of the glow-worm (*Arachnocampa richardsae*) rearing at Tama Zoo-Fascination of a living milky way. Insectarium, vol 34 November: 336-342.
Viviani, Hastings et al. Photochem Photobiol. 75(1):22-7 (2002)
Viviani, V. R., Cell. Mol. Life Sci. 59:1833-1850 (2002)
von Heinje, G., Sequence Analysis in Molecular Biology, Academic Press, (1987)
Wada et al., Nucleic Acids Res. 20:2111-2118 (1992)
WO/1995/011995
WO/1999/066324
WO/2000/024878
WO1999/049019
Wold, F., Posttranslational Covalent Modification of Proteins, B. C. Johnson, Ed., Academic Press, New York 1-12 (1983)
Wood, K. V., (1998) *The Chemistry of Bioluminescent Reporter Assays*, Promega Notes 65, page 14.
Wood et al., Science 244, 700-702 (1989)
Wood, K. V., Evolution of bioluminescence in insects. VII International *Symposium* on Bioluminescence and Chemiluminescence, Wiley, Chichester, UK (1983).
Xu, Y., D. W. Piston, et al., Proc Natl Acad Sci USA 96(1): 151-6 (1999).

---

SEQUENCE LISTING

```
<160> NUMBER OF SEQ ID NOS: 66

<210> SEQ ID NO 1
<211> LENGTH: 1713
<212> TYPE: DNA
<213> ORGANISM: Arachnocampa richardsae

<400> SEQUENCE: 1
atcaattgtc ttgtgaaatt ctcagtgaca atggcttgta cttcagtgaa taatattgta      60
tatggtccta agccgacctt tgatgtcttg aaggaggcta attcgtatgg tgaatatgca     120
tttaaacgat tgagagccag aggtgatgaa gtttcagtta ttgatgccct aacaggagag     180
gaaattcgtg catccgatat ttatgctaag accgtgcgaa cagctgagtg tcttcaagct     240
tatggcatca gaaagggcga tcgtgttggt atttgcagtg ataccatgat tgaatactat     300
tacattgtaa tgggaacaat ggcagttggt gctattatct gtccaattat tatttcatgg     360
actgaagccg acatgaacca tgcttttaat atttcatgtc caacggtttt ctttgtttcg     420
aaaagtattt tgccaacgat tgctcgaatt gctaagagaa atccttatgt aaaggacatt     480
attgtctttg atgataatgc accagaaaag ccattgataa gctttaaaga ttttttggct     540
```

```
aatccaaaag tgccatcaaa accacatttt gattgtgaac cacaagacat ggaaaatacc    600
attgccactg ttttattgac atctggtact acgggtattt ctaaaggtgt tgctatatcg    660
caatataatc tgatccactt catgtcactg gacactaaga cttacaagaa gggcctattt    720
ttgtgtgtag cacagtactc taatgcgttt ggttttactg cattgatgag acgtgcattt    780
aatggcacca gggtacttca tttgccaaga tatgacgaga agagttactt agaatgcgtt    840
caaaaattca aggtcaatta catcagtgtt caccctccct tgatgttgtc attagctaag    900
aaacccgaaa ttgcgaacta tgatttgtct agtcttgaac gtatttattg ctctggtaca    960
acagtgagtg ttcgaatttt atatcaagta gctgagagaa ttggcgtcaa ggtcgtacgt   1020
caatttatg gatccagtga atgtttggcg gtcgttgctc aaagtgatga attttgtacc   1080
aaaggaagtg ttggtacact tatgcctgga attattggca aagttataca tccagaaact   1140
ggtgccctte ttgggccaaa tgaacgcggt ttcttgaaat ttaaggctaa cagcactatg   1200
tatggttatt caacaatcc tgaagcctcc aaagttgtta agatgaaga gggttatgtt    1260
aatactggtg atgctggata ttataatgaa agatttgaat ggttcgttgt tgatagatta   1320
aaggatatag ttatggtcga tggtgtagcc gttgcaccaa cagaaatgga aactaccata   1380
ttgcttcatc ccgatattat tgatgcttgt gtcattggta tctctgatgg tgaaggtggt   1440
gaagtattat ttgcattctt gactaagact aggaaagagg ttactgaaaa agatgtcatg   1500
gacttcgttg cagaaaaact accttatccc aagcatctta aggtggctg ccaatttgtt    1560
gatgaaatac ccaagaatcc agctggcaaa atgttgcgtc gtattttaag aggaacattg   1620
taaattgaaa aaataatttg tttcttattt aatttgaaat aaatgcgatt gcatataaaa   1680
gaaaaaaaaa aaagaaaaa aaaaaaaaaa aaa                                 1713
```

<210> SEQ ID NO 2
<211> LENGTH: 530
<212> TYPE: PRT
<213> ORGANISM: Arachnocampa richardsae

<400> SEQUENCE: 2

```
Met Ala Cys Thr Ser Val Asn Asn Ile Val Tyr Gly Pro Lys Pro Thr
1               5                   10                  15

Phe Asp Val Leu Lys Glu Ala Asn Ser Tyr Gly Glu Tyr Ala Phe Lys
            20                  25                  30

Arg Leu Arg Ala Arg Gly Asp Glu Val Ser Val Ile Asp Ala Leu Thr
        35                  40                  45

Gly Glu Glu Ile Arg Ala Ser Asp Ile Tyr Ala Lys Thr Val Arg Thr
    50                  55                  60

Ala Glu Cys Leu Gln Ala Tyr Gly Ile Arg Lys Gly Asp Arg Val Gly
65                  70                  75                  80

Ile Cys Ser Asp Thr Met Ile Glu Tyr Tyr Ile Val Met Gly Thr
                85                  90                  95

Met Ala Val Gly Ala Ile Ile Cys Pro Ile Ile Ser Trp Thr Glu
            100                 105                 110

Ala Asp Met Asn His Ala Phe Asn Ile Ser Cys Pro Thr Val Phe Phe
        115                 120                 125

Val Ser Lys Ser Ile Leu Pro Thr Ile Ala Arg Ile Ala Lys Arg Asn
    130                 135                 140

Pro Tyr Val Lys Asp Ile Ile Val Phe Asp Asp Asn Ala Pro Glu Lys
145                 150                 155                 160

Pro Leu Ile Ser Phe Lys Asp Phe Leu Ala Asn Pro Lys Val Pro Ser
```

```
                   165                 170                 175
Lys Pro His Phe Asp Cys Glu Pro Gln Asp Met Glu Asn Thr Ile Ala
                180                 185                 190
Thr Val Leu Leu Thr Ser Gly Thr Gly Ile Ser Lys Gly Val Ala
            195                 200                 205
Ile Ser Gln Tyr Asn Leu Ile His Phe Met Ser Leu Asp Thr Lys Thr
        210                 215                 220
Tyr Lys Lys Gly Leu Phe Leu Cys Val Ala Gln Tyr Ser Asn Ala Phe
225                 230                 235                 240
Gly Phe Thr Ala Leu Met Arg Arg Ala Phe Asn Gly Thr Arg Val Leu
                245                 250                 255
His Leu Pro Arg Tyr Asp Glu Lys Ser Tyr Leu Glu Cys Val Gln Lys
            260                 265                 270
Phe Lys Val Asn Tyr Ile Ser Val His Pro Pro Leu Met Leu Ser Leu
        275                 280                 285
Ala Lys Lys Pro Glu Ile Ala Asn Tyr Asp Leu Ser Ser Leu Glu Arg
    290                 295                 300
Ile Tyr Cys Ser Gly Thr Thr Val Ser Val Arg Ile Leu Tyr Gln Val
305                 310                 315                 320
Ala Glu Arg Ile Gly Val Lys Val Val Arg Gln Phe Tyr Gly Ser Ser
                325                 330                 335
Glu Cys Leu Ala Val Val Ala Gln Ser Asp Glu Phe Cys Thr Lys Gly
            340                 345                 350
Ser Val Gly Thr Leu Met Pro Gly Ile Ile Gly Lys Val Ile His Pro
        355                 360                 365
Glu Thr Gly Ala Leu Leu Gly Pro Asn Glu Arg Gly Phe Leu Lys Phe
    370                 375                 380
Lys Ala Asn Ser Thr Met Tyr Gly Tyr Phe Asn Asn Pro Glu Ala Ser
385                 390                 395                 400
Lys Val Val Lys Asp Glu Glu Gly Tyr Val Asn Thr Gly Asp Ala Gly
                405                 410                 415
Tyr Tyr Asn Glu Arg Phe Glu Trp Phe Val Val Asp Arg Leu Lys Asp
            420                 425                 430
Ile Val Met Val Asp Gly Val Ala Val Ala Pro Thr Glu Met Glu Thr
        435                 440                 445
Thr Ile Leu Leu His Pro Asp Ile Ile Asp Ala Cys Val Ile Gly Ile
    450                 455                 460
Ser Asp Gly Glu Gly Gly Glu Val Leu Phe Ala Phe Leu Thr Lys Thr
465                 470                 475                 480
Arg Lys Glu Val Thr Glu Lys Asp Val Met Asp Phe Val Ala Glu Lys
                485                 490                 495
Leu Pro Tyr Pro Lys His Leu Lys Gly Gly Cys Gln Phe Val Asp Glu
            500                 505                 510
Ile Pro Lys Asn Pro Ala Gly Lys Met Leu Arg Arg Ile Leu Arg Gly
        515                 520                 525
Thr Leu
    530

<210> SEQ ID NO 3
<211> LENGTH: 1711
<212> TYPE: DNA
<213> ORGANISM: Arachnocampa richardsae

<400> SEQUENCE: 3
atcaattgtc ttgtgaaatt ctcagtgaca atggcttgta cttcagtgaa taatattgta     60
```

-continued

```
tatggtccta agccgacctt tgatgtcttg aaggaggcta attcgtatgg tgaatatgca      120
tttaaacgat tgagagccag aggtgatgaa gtttcagtta ttgatgccct aacaggagag      180
gaaattcgtg catccgatat ttatgctaag accgtgcgaa cagctgagtg tcttcaagct      240
tatggcatca gaaagggcga tcgtgttggt atttgcagtg ataccatgat tgaatactat      300
tacattgtaa tgggaacaat ggcagttggt gctattatct gtccaattat tatttcatgg      360
actgaagccg acatgaacca tgcttttaat atttcatgtc aacggttttt ctttgtttcg      420
aaaagtattt tgccaacgat tgctcgaatt gctaagagaa tcccttatgt aaaggacatt      480
attgtctttg atgataatgc accagaaaag ccattgataa gctttaaaga ttttttggct      540
aatccaaaag tgccatcaaa accacatttt gattgtgaac cacaagacat ggaaaatacc      600
attgccactg ttttattgac atctggtact acgggtattt ctaaaggtgt tgctatatcg      660
caatataatc tgatccactt catgtcactg gacactaaga cttacaagaa gggcctattt      720
ttgtgtgtag cacagtactc taatgcgttt ggttttactg cattgatgag acgtgcattt      780
aatggcacca gggtacttca tttgccaaga tatgacgaga agagttactt agaatgcgtt      840
caaaaattca aggtcaatta catcagtgtt caccctccct tgatgttgtc attagctaag      900
aaacccgaaa ttgcgaacta tgatttgtct agtcttgaac gtatttattg ctctggtaca      960
acagtgagtg ttcgaatttt atatcaagta gctgagagaa ttggcgtcaa ggtcgtacgt     1020 caatttatg gatccagtga atgtttggcg tcgttgctc aaagtgatga attttgtacc      1080
aaaggaagtg ttggtacact tatgcctgga attattggca agttatacat ccagaaaact     1140
ggtgcccttc ttgggccaaa tgaacgcggt ttcttgaaat ttaaggctaa cagcactatg     1200
tatggttatt caacaatcc tgaagcctcc aaagttgtta agatgaaga gggttatgtt      1260 aatactggtg atgctggata ttataatgaa agatttgaat ggttcgttgt tgatagatta     1320
aaggatatag ttatggtcga tggtgtagcc gttgcaccaa cagaaatgga aactaccata     1380
ttgcttcatc ccgatattat tgatgcttgt gtcattggta tctctgatgg tgaaggtggt     1440
gaagtattat ttgcattctt gactaagact aggaaagagg ttactgaaaa agatgtcatg     1500
gacttcgttg cagaaaaact accttatccc aagcatctta aaggtggctg ccaatttgtt     1560
gatgaaatac ccaagaatcc agctggcaaa atgttgcgtc gtattttaag aggaacattg     1620
taaattgaaa aataatttg tttcttattt aatttgaaat aaatgcgatt gcatataaag     1680
caaaaaaaaa aaaaaaaaa aaaaaaaaaa a                                     1711
```

<210> SEQ ID NO 4
<211> LENGTH: 550
<212> TYPE: PRT
<213> ORGANISM: Photinus pyralis

<400> SEQUENCE: 4

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80
```

```
Cys Ser Glu Asn Ser Leu Gln Phe Phe Met Pro Val Leu Gly Ala Leu
                 85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
            115                 120                 125

Ser Lys Lys Gly Leu Gln Lys Ile Leu Asn Val Gln Lys Lys Leu Pro
            130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
            195                 200                 205

Ala Leu Pro His Arg Thr Ala Cys Val Arg Phe Ser His Ala Arg Asp
            210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
            275                 280                 285

Pro Thr Leu Phe Ser Phe Phe Ala Lys Ser Thr Leu Ile Asp Lys Tyr
            290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
            355                 360                 365

Phe Glu Ala Lys Val Val Asp Leu Asp Thr Gly Lys Thr Leu Gly Val
            370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
            450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510
```

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
        530                 535                 540

Gly Gly Lys Ser Lys Leu
545                 550

<210> SEQ ID NO 5
<211> LENGTH: 1593
<212> TYPE: DNA
<213> ORGANISM: Arachnocampa flava

<400> SEQUENCE: 5

```
atggcttgta cttcagtgaa taatattgta tatggtccta aaccgacctt tgatgtcttg      60
aaggaggcta attcgtatgg tgaatatgca tttaaacgat tgagagccag aggtgacgaa     120
gtttcagtta ttgatgccct aacaggagag gaaattcgtg catccgatat ttatgctaag     180
accgtgcgaa cagctgagtg tcttcaagct tatggcatca ggaagggcga tcgtgttggt     240
atttgcagtg ataccatgat tgaatactat tacattgtaa tgggaacaat ggcagttggt     300
gctattatct gtccaattat tatttcatgg actgaagccg acatgaacca tgcttttaat     360
atttcatgtc caacggtttt ctttgtttca aaaagtattt tgccaacgat tgctcgaatt     420
gctaagagaa tccttatgt aaaggacatt attgtctttg atgatgatgc accagaaaag     480
ccattaataa gctttaaaga ttttttggct aatcccaaag tgccatcaaa accacatttt     540
gattgtgaac cacaagacat ggaaaatacc attgccactg ttttattgac atctggtaca     600
acgggtattt ctaaaggtgt tgctatatcg caatataatc tgatccactt tatgtcattg     660
gacactaaga cttacaagaa gggcttgttt ttgtgtgtag cacagtactc taatgctttt     720
ggtttcactg cattgatgag acgtgcgttt aatggcacca gggtactcca tttaccaaga     780
tatgacgaaa agagttactt ggaatgtgtt caaaaattca aggtcaatta catcagtgtt     840
catcctccct tgatgttgtc attagctaag aaacccgaaa ttgctaacta tgatttgtct     900
agtcttgaac gtatttattg ttctggtaca acagtgagtg ttcgaatttt atatcaagta     960
gctgagagac ttggcgtcaa ggtcgtacgt caattttatg gatccagtga atgtttggca    1020
gtcgttgctc aaagtgatga attttgtacc aaaggaagtg ttggtacact catgcctgga    1080
attattggca agttatacat cctgaaact ggtgcccttc ttggaccaaa tgaacgcggt    1140
ttcttgaaat taaggctaa cagcactatg tatggttatt caataatcc tgaagcctcc    1200
aaagttgtta agatgaaga aggatatgtt aatactggtg atgctggata ttataatgaa    1260
agatttgaat ggttcgttgt ggatagatta aggatatag taatggtcga tggtgtagcc    1320
gttgcaccaa cagaaatgga aactaccata ttgcttcatc ccgatattat tgatgcttgt    1380
gtcattggta tctctgatgg tgaaggtggt gaagtattat ttgcattctt gactaagact    1440
aggaaagagg ttactgaaaa agatgtcatg gactttgttg cagaaaaact accatacccc    1500
aagcatctta aggtggctg ccaatttgtt gatgaaatac caagaatcc agctggtaaa    1560
atgttgcgtc gtattttaag aggaacattg taa                                 1593
```

<210> SEQ ID NO 6
<211> LENGTH: 530
<212> TYPE: PRT
<213> ORGANISM: Arachnocampa flava

<400> SEQUENCE: 6

-continued

```
Met Ala Cys Thr Ser Val Asn Asn Ile Val Tyr Gly Pro Lys Pro Thr
1               5                   10                  15
Phe Asp Val Leu Lys Glu Ala Asn Ser Tyr Gly Glu Tyr Ala Phe Lys
                20                  25                  30
Arg Leu Arg Ala Arg Gly Asp Glu Val Ser Val Ile Asp Ala Leu Thr
            35                  40                  45
Gly Glu Glu Ile Arg Ala Ser Asp Ile Tyr Ala Lys Thr Val Arg Thr
    50                  55                  60
Ala Glu Cys Leu Gln Ala Tyr Gly Ile Arg Lys Gly Asp Arg Val Gly
65                  70                  75                  80
Ile Cys Ser Asp Thr Met Ile Glu Tyr Tyr Ile Val Met Gly Thr
                85                  90                  95
Met Ala Val Gly Ala Ile Ile Cys Pro Ile Ile Ser Trp Thr Glu
                100                 105                 110
Ala Asp Met Asn His Ala Phe Asn Ile Ser Cys Pro Thr Val Phe Phe
            115                 120                 125
Val Ser Lys Ser Ile Leu Pro Thr Ile Ala Arg Ile Ala Lys Arg Asn
    130                 135                 140
Pro Tyr Val Lys Asp Ile Ile Val Phe Asp Asp Ala Pro Glu Lys
145                 150                 155                 160
Pro Leu Ile Ser Phe Lys Asp Phe Leu Ala Asn Pro Lys Val Pro Ser
                165                 170                 175
Lys Pro His Phe Asp Cys Glu Pro Gln Asp Met Glu Asn Thr Ile Ala
                180                 185                 190
Thr Val Leu Leu Thr Ser Gly Thr Gly Ile Ser Lys Gly Val Ala
    195                 200                 205
Ile Ser Gln Tyr Asn Leu Ile His Phe Met Ser Leu Asp Thr Lys Thr
210                 215                 220
Tyr Lys Lys Gly Leu Phe Leu Cys Val Ala Gln Tyr Ser Asn Ala Phe
225                 230                 235                 240
Gly Phe Thr Ala Leu Met Arg Arg Ala Phe Asn Gly Thr Arg Val Leu
                245                 250                 255
His Leu Pro Arg Tyr Asp Glu Lys Ser Tyr Leu Glu Cys Val Gln Lys
                260                 265                 270
Phe Lys Val Asn Tyr Ile Ser Val His Pro Pro Leu Met Leu Ser Leu
            275                 280                 285
Ala Lys Lys Pro Glu Ile Ala Asn Tyr Asp Leu Ser Ser Leu Glu Arg
290                 295                 300
Ile Tyr Cys Ser Gly Thr Thr Val Ser Val Arg Ile Leu Tyr Gln Val
305                 310                 315                 320
Ala Glu Arg Leu Gly Val Lys Val Val Arg Gln Phe Tyr Gly Ser Ser
                325                 330                 335
Glu Cys Leu Ala Val Val Ala Gln Ser Asp Glu Phe Cys Thr Lys Gly
            340                 345                 350
Ser Val Gly Thr Leu Met Pro Gly Ile Ile Gly Lys Val Ile His Pro
    355                 360                 365
Glu Thr Gly Ala Leu Leu Gly Pro Asn Glu Arg Gly Phe Leu Lys Phe
370                 375                 380
Lys Ala Asn Ser Thr Met Tyr Gly Tyr Phe Asn Asn Pro Glu Ala Ser
385                 390                 395                 400
Lys Val Val Lys Asp Glu Gly Tyr Val Asn Thr Gly Asp Ala Gly
                405                 410                 415
Tyr Tyr Asn Glu Arg Phe Glu Trp Phe Val Val Asp Arg Leu Lys Asp
                420                 425                 430
```

```
Ile Val Met Val Asp Gly Val Ala Val Ala Pro Thr Glu Met Glu Thr
        435                 440                 445

Thr Ile Leu Leu His Pro Asp Ile Ile Asp Ala Cys Val Ile Gly Ile
    450                 455                 460

Ser Asp Gly Glu Gly Glu Val Leu Phe Ala Phe Leu Thr Lys Thr
465                 470                 475                 480

Arg Lys Glu Val Thr Glu Lys Asp Val Met Asp Phe Val Ala Glu Lys
                485                 490                 495

Leu Pro Tyr Pro Lys His Leu Lys Gly Gly Cys Gln Phe Val Asp Glu
            500                 505                 510

Ile Pro Lys Asn Pro Ala Gly Lys Met Leu Arg Arg Ile Leu Arg Gly
            515                 520                 525

Thr Leu
    530

<210> SEQ ID NO 7
<211> LENGTH: 1593
<212> TYPE: DNA
<213> ORGANISM: Arachnocampa girraweenensis

<400> SEQUENCE: 7
atggcttgta cttcagtgaa taatattgta tatggtccta aaccgacctt tgatgtcttg      60
aaggaggcta attcgtatgg tgaatatgca tttaaacgat tgagagccag aggtgatgaa     120
gtttcagtta ttgatgctct aacaggagaa gaaattcgtg cttccgatat ttatgctaag     180
accgtgcgaa cagctgagtg ccttcaagct tatggcatca gaaagggcga tcgtgttggt     240
atttgcagtg ataccatgat tgaatactat tacattgtga tgggaacaat ggcagttggt     300
gctattatct gtccaattat tatttcatgg accgaagccg acatgaacca tgcttttaat     360
atttcatgtc ccacggtttt ctttgtttcg aaaagtattt tgccaactat tgctcgaatt     420
gctaagagaa atccttatgt aaaggacatt attgtctttg atgataatgc accagaaaag     480
ccattgataa gctttaaaga ttttttggct aatccaaaag tgccatcaaa accacatttt     540
gattgtgaac cacaagacat ggaaaatact atagccactg ttttattgac atctggtact     600
acgggtattt ctaaaggtgt tgctatatcg caatataatc taattcactt catgtcactg     660
gacacaaaga cctacaagaa aggcctgttt tgtgtgtgtag cacagtactc taatgcgttt     720
ggttttactg cattgatgag acgtgcattt aatggtacca gggtactcca tttaccaaga     780
tatgacgaaa agagttactt ggaatgcgtt caaaaattca aggtcaatta catcagtgtt     840
catcctccct tgatgttgtc attagctaag aaacccgaaa ttgctaacta tgatttgtct     900
agtcttgaac gtatttattg ttctggtaca acagtgagtg ttcgaatttt ataccaagta     960
gctgagagac ttggcgtcaa ggtcgtacgt caatttatg gatccagtga atgtttggca    1020
gtcgttgctc aaagtgatga attttgtacc aaaggaagtg ttggtacact catgcctgga    1080
attattggca agttatacat cctgaaaact ggtgcccttc ttggaccaaa tgaacgcggt    1140
ttcttgaaat taaggctaa cagcactatg tatggttatt tcaataaccc tgaagcctcc    1200
aaagttgtta agatgaaga aggatatgtt aatactggtg atgctggata ttataatgaa    1260
agatttgaat ggttcgttgt tgatagatta aaggatatag ttatggtcga tggtgtagcc    1320
gttgcaccaa cagaaatgga aactaccata ttgcttcatc ccgatattat tgatgcttgt    1380
gtcattggta tctctgatgg tgaaggtggt gaagtattat ttgcattctt gactaagact    1440
aggaaagagg ttactgaaaa agatgtcatg gactttgttg cagaaaaact accttatccc    1500
```

```
aagcatctta aaggcggctg ccaatttgtt gatgaaatac ccaagaatcc agctggcaaa    1560
atgttgcgtc gtattttaag aggaacattg taa                                 1593
```

<210> SEQ ID NO 8
<211> LENGTH: 530
<212> TYPE: PRT
<213> ORGANISM: Arachnocampa girraweenensis

<400> SEQUENCE: 8

```
Met Ala Cys Thr Ser Val Asn Asn Ile Val Tyr Gly Pro Lys Pro Thr
1               5                   10                  15

Phe Asp Val Leu Lys Glu Ala Asn Ser Tyr Gly Glu Tyr Ala Phe Lys
            20                  25                  30

Arg Leu Arg Ala Arg Gly Asp Glu Val Ser Val Ile Asp Ala Leu Thr
        35                  40                  45

Gly Glu Glu Ile Arg Ala Ser Asp Ile Tyr Ala Lys Thr Val Arg Thr
    50                  55                  60

Ala Glu Cys Leu Gln Ala Tyr Gly Ile Arg Lys Gly Asp Arg Val Gly
65                  70                  75                  80

Ile Cys Ser Asp Thr Met Ile Glu Tyr Tyr Ile Val Met Gly Thr
                85                  90                  95

Met Ala Val Gly Ala Ile Ile Cys Pro Ile Ile Ser Trp Thr Glu
            100                 105                 110

Ala Asp Met Asn His Ala Phe Asn Ile Ser Cys Pro Thr Val Phe Phe
        115                 120                 125

Val Ser Lys Ser Ile Leu Pro Thr Ile Ala Arg Ile Ala Lys Arg Asn
    130                 135                 140

Pro Tyr Val Lys Asp Ile Ile Val Phe Asp Asp Asn Ala Pro Glu Lys
145                 150                 155                 160

Pro Leu Ile Ser Phe Lys Asp Phe Leu Ala Asn Pro Lys Val Pro Ser
                165                 170                 175

Lys Pro His Phe Asp Cys Glu Pro Gln Asp Met Glu Asn Thr Ile Ala
            180                 185                 190

Thr Val Leu Leu Thr Ser Gly Thr Thr Gly Ile Ser Lys Gly Val Ala
        195                 200                 205

Ile Ser Gln Tyr Asn Leu Ile His Phe Met Ser Leu Asp Thr Lys Thr
    210                 215                 220

Tyr Lys Lys Gly Leu Phe Leu Cys Val Ala Gln Tyr Ser Asn Ala Phe
225                 230                 235                 240

Gly Phe Thr Ala Leu Met Arg Arg Ala Phe Asn Gly Thr Arg Val Leu
                245                 250                 255

His Leu Pro Arg Tyr Asp Glu Lys Ser Tyr Leu Glu Cys Val Gln Lys
            260                 265                 270

Phe Lys Val Asn Tyr Ile Ser Val His Pro Pro Leu Met Leu Ser Leu
        275                 280                 285

Ala Lys Lys Pro Glu Ile Ala Asn Tyr Asp Leu Ser Ser Leu Glu Arg
    290                 295                 300

Ile Tyr Cys Ser Gly Thr Thr Val Ser Val Arg Ile Leu Tyr Gln Val
305                 310                 315                 320

Ala Glu Arg Leu Gly Val Lys Val Val Arg Gln Phe Tyr Gly Ser Ser
                325                 330                 335

Glu Cys Leu Ala Val Val Ala Gln Ser Asp Glu Phe Cys Thr Lys Gly
            340                 345                 350

Ser Val Gly Thr Leu Met Pro Gly Ile Ile Gly Lys Val Ile His Pro
        355                 360                 365
```

```
Glu Thr Gly Ala Leu Leu Gly Pro Asn Glu Arg Gly Phe Leu Lys Phe
    370                 375                 380

Lys Ala Asn Ser Thr Met Tyr Gly Tyr Phe Asn Asn Pro Glu Ala Ser
385                 390                 395                 400

Lys Val Val Lys Asp Glu Glu Gly Tyr Val Asn Thr Gly Asp Ala Gly
                405                 410                 415

Tyr Tyr Asn Glu Arg Phe Glu Trp Phe Val Val Asp Arg Leu Lys Asp
                420                 425                 430

Ile Val Met Val Asp Gly Val Ala Val Ala Pro Thr Glu Met Glu Thr
            435                 440                 445

Thr Ile Leu Leu His Pro Asp Ile Ile Asp Ala Cys Val Ile Gly Ile
        450                 455                 460

Ser Asp Gly Glu Gly Glu Val Leu Phe Ala Phe Leu Thr Lys Thr
465                 470                 475                 480

Arg Lys Glu Val Thr Glu Lys Asp Val Met Asp Phe Val Ala Glu Lys
                485                 490                 495

Leu Pro Tyr Pro Lys His Leu Lys Gly Gly Cys Gln Phe Val Asp Glu
                500                 505                 510

Ile Pro Lys Asn Pro Ala Gly Lys Met Leu Arg Arg Ile Leu Arg Gly
                515                 520                 525

Thr Leu
    530

<210> SEQ ID NO 9
<211> LENGTH: 1593
<212> TYPE: DNA
<213> ORGANISM: Arachnocampa tasmaniensis

<400> SEQUENCE: 9
atgacttcta catctgtgga taatatcgtt tatggcccaa aaccaaaatt cgatgttcta      60
aaggaggcca attcttatgg tgaatataca tttaaacggt tgagagccag aggtgatgag     120
gtttcagtta tcgatggcgt taccggggag catattaccg cttccacaat ttatgccaaa     180
accgtacgaa cagctgaatg tcttcaagcc tatggcatta ggaaaggcga tcgcattggt     240
atttgcagtg acacaatgat tgaatattac tatattgtaa tgggaacaat ggctgttggc     300
gctatcattt gccctgtaat tatttcatgg acggaagccg acatgaacca tgcttttcaat    360
atttcatgtc caacggtctt ctttgtctca aaaagtattc taccaacaat tgctaaatta     420
tcaaagagga atcctatgt aaaggatatc attgttttg acgatgagtc acctgagaag      480
ccatttataa gcttcaaaga tttcttggcc aatccaaagg ttccatctaa gcctcatttt     540
gattgtgaac cacaagatat ggaaagtact attgccactg tttatgtac atctggtact      600
acgggtatttt ctaaaggtgt tgccatatcg caatataatc tgatccactt catgtcattg    660
gatactaaaa atgacaagaa aggtctattc ttgtgcgtgg ctcagtattc gaatgctttt     720
ggttttacgg cattgatgag acgtgcattt aatggtacca gggtaatcca tttaccaaaa    780
tatgaagaaa aagcatattt ggaatgcgtt caaaaataca aggtaaacta ttattagcgtc    840
catcctccct tgatgttgtc attggctaag aaacccgaaa tcgttaacta cgatttatct     900
agtcttgaac gtatttattg ctctggcact acgtgagcg tacgaatttt gtatgctgta     960
gctgatagac ttggtgtgaa ttatgttcgt caattttatg gttcaagtga atgtttggcc    1020
gtggtggcgc aaagtgatga atattgtacc aagggtagtg ttggtacact tatgcctggt    1080
attattggta agttgtaca tcctgagact ggtgctcttc ttggacccaa ccaacgtggt    1140
```

-continued

```
ttcttgaaat ttaaggccaa cagtactatg tatggttact acaataatcc agaagcatcc   1200
aaagtggtta aagatgaaga aggatatgtt aatactggtg atgctggata ttataatgat   1260
cgatttgaat ggttcgttgt tgatagatta aaggatattg ttatggtcga tggtgtaggt   1320
gtggcaccaa ctgaaatgga agcagttata ttgcttcatc ccgatattat tgatgcttgt   1380
gttattggta tttcggatgg tgaaggtggt gaaattttgt ttgcattctt gaccaaaact   1440
agaaaagaac tcactgaaaa ggatgtcatg gatttcgttg ccgaaaaact accctatccc   1500
aaacatctca aggtggctg tcaatttgtt gaagaaattc caagaatcc agctggaaag    1560 atgttgcgtc gtattttaag atcaacattg taa                               1593
```

<210> SEQ ID NO 10
<211> LENGTH: 530
<212> TYPE: PRT
<213> ORGANISM: Arachnocampa tasmaniensis

<400> SEQUENCE: 10

```
Met Thr Ser Thr Ser Val Asp Asn Ile Val Tyr Gly Pro Lys Pro Lys
 1               5                  10                  15

Phe Asp Val Leu Lys Glu Ala Asn Ser Tyr Gly Glu Tyr Thr Phe Lys
             20                  25                  30

Arg Leu Arg Ala Arg Gly Asp Glu Val Ser Val Ile Asp Gly Val Thr
         35                  40                  45

Gly Glu His Ile Thr Ala Ser Thr Ile Tyr Ala Lys Thr Val Arg Thr
     50                  55                  60

Ala Glu Cys Leu Gln Ala Tyr Gly Ile Arg Lys Gly Asp Arg Ile Gly
 65                  70                  75                  80

Ile Cys Ser Asp Thr Met Ile Glu Tyr Tyr Tyr Ile Val Met Gly Thr
                 85                  90                  95

Met Ala Val Gly Ala Ile Ile Cys Pro Val Ile Ser Trp Thr Glu
            100                 105                 110

Ala Asp Met Asn His Ala Phe Asn Ile Ser Cys Pro Thr Val Phe Phe
        115                 120                 125

Val Ser Lys Ser Ile Leu Pro Thr Ile Ala Lys Leu Ser Lys Arg Asn
    130                 135                 140

Pro Tyr Val Lys Asp Ile Ile Val Phe Asp Asp Glu Ser Pro Glu Lys
145                 150                 155                 160

Pro Phe Ile Ser Phe Lys Asp Phe Leu Ala Asn Pro Lys Val Pro Ser
                165                 170                 175

Lys Pro His Phe Asp Cys Glu Pro Gln Asp Met Glu Ser Thr Ile Ala
            180                 185                 190

Thr Val Leu Cys Thr Ser Gly Thr Thr Gly Ile Ser Lys Gly Val Ala
        195                 200                 205

Ile Ser Gln Tyr Asn Leu Ile His Phe Met Ser Leu Asp Thr Lys Asn
    210                 215                 220

Asp Lys Lys Gly Leu Phe Leu Cys Val Ala Gln Tyr Ser Asn Ala Phe
225                 230                 235                 240

Gly Phe Thr Ala Leu Met Arg Arg Ala Phe Asn Gly Thr Arg Val Ile
                245                 250                 255

His Leu Pro Lys Tyr Glu Glu Lys Ala Tyr Leu Glu Cys Val Gln Lys
            260                 265                 270

Tyr Lys Val Asn Tyr Ile Ser Val His Pro Pro Leu Met Leu Ser Leu
        275                 280                 285

Ala Lys Lys Pro Glu Ile Val Asn Tyr Asp Leu Ser Ser Leu Glu Arg
    290                 295                 300
```

Ile Tyr Cys Ser Gly Thr Thr Val Ser Val Arg Ile Leu Tyr Ala Val
305                 310                 315                 320

Ala Asp Arg Leu Gly Val Asn Tyr Val Arg Gln Phe Tyr Gly Ser Ser
            325                 330                 335

Glu Cys Leu Ala Val Val Ala Gln Ser Asp Glu Tyr Cys Thr Lys Gly
            340                 345                 350

Ser Val Gly Thr Leu Met Pro Gly Ile Ile Gly Lys Val Val His Pro
        355                 360                 365

Glu Thr Gly Ala Leu Leu Gly Pro Asn Gln Arg Gly Phe Leu Lys Phe
    370                 375                 380

Lys Ala Asn Ser Thr Met Tyr Gly Tyr Tyr Asn Asn Pro Glu Ala Ser
385                 390                 395                 400

Lys Val Val Lys Asp Glu Glu Gly Tyr Val Asn Thr Gly Asp Ala Gly
                405                 410                 415

Tyr Tyr Asn Asp Arg Phe Glu Trp Phe Val Val Asp Arg Leu Lys Asp
            420                 425                 430

Ile Val Met Val Asp Gly Val Gly Val Ala Pro Thr Glu Met Glu Ala
            435                 440                 445

Val Ile Leu Leu His Pro Asp Ile Ile Asp Ala Cys Val Ile Gly Ile
    450                 455                 460

Ser Asp Gly Glu Gly Gly Glu Ile Leu Phe Ala Phe Leu Thr Lys Thr
465                 470                 475                 480

Arg Lys Glu Leu Thr Glu Lys Asp Val Met Asp Phe Val Ala Glu Lys
                485                 490                 495

Leu Pro Tyr Pro Lys His Leu Lys Gly Gly Cys Gln Phe Val Glu Glu
            500                 505                 510

Ile Pro Lys Asn Pro Ala Gly Lys Met Leu Arg Arg Ile Leu Arg Ser
            515                 520                 525

Thr Leu
    530

<210> SEQ ID NO 11
<211> LENGTH: 21
<212> TYPE: DNA
<213> ORGANISM: Artificial Sequence
<220> FEATURE:
<223> OTHER INFORMATION: Synthetic forward primer, GWLucScreenU

<400> SEQUENCE: 11
gatgataatg caccagaaaa g                                          21

<210> SEQ ID NO 12
<211> LENGTH: 21
<212> TYPE: DNA
<213> ORGANISM: Artificial Sequence
<220> FEATURE:
<223> OTHER INFORMATION: Synthetic reverse primer, GWLucScreenL

<400> SEQUENCE: 12
ttataatatc cagcatcacc a                                          21

<210> SEQ ID NO 13
<211> LENGTH: 19
<212> TYPE: DNA
<213> ORGANISM: Artificial Sequence
<220> FEATURE:
<223> OTHER INFORMATION: Synthetic SMART IV Oligo primer

<400> SEQUENCE: 13

-continued caacgcagag tggccatta                                          19

<210> SEQ ID NO 14
<211> LENGTH: 21
<212> TYPE: DNA
<213> ORGANISM: Artificial Sequence
<220> FEATURE:
<223> OTHER INFORMATION: Synthetic luciferase gene-specific primer 514-
      494

<400> SEQUENCE: 14 tggctttttct ggtgcattat c                                      21

<210> SEQ ID NO 15
<211> LENGTH: 25
<212> TYPE: DNA
<213> ORGANISM: Artificial Sequence
<220> FEATURE:
<223> OTHER INFORMATION: Synthetic pETGWLucF primer

<400> SEQUENCE: 15
gacacaccat ggcttgtact tcagt                                   25

<210> SEQ ID NO 16
<211> LENGTH: 31
<212> TYPE: DNA
<213> ORGANISM: Artificial Sequence
<220> FEATURE:
<223> OTHER INFORMATION: Synthetic pETGWLucR primer

<400> SEQUENCE: 16
gacgacccta ggttacaatg ttcctcttaa a                            31

<210> SEQ ID NO 17
<211> LENGTH: 19
<212> TYPE: DNA
<213> ORGANISM: Artificial Sequence
<220> FEATURE:
<223> OTHER INFORMATION: Synthetic GWLO8F5F250 primer

<400> SEQUENCE: 17
agaaagggcg atcgtgttg                                          19

<210> SEQ ID NO 18
<211> LENGTH: 21
<212> TYPE: DNA
<213> ORGANISM: Artificial Sequence
<220> FEATURE:
<223> OTHER INFORMATION: Synthetic GWLucScreenU primer

<400> SEQUENCE: 18
gatgataatg caccagaaaa g                                       21

<210> SEQ ID NO 19
<211> LENGTH: 22
<212> TYPE: DNA
<213> ORGANISM: Artificial Sequence
<220> FEATURE:
<223> OTHER INFORMATION: Synthetic GWLO91E1F250 primer

<400> SEQUENCE: 19
accattgcca ctgttttatt ga                                      22

<210> SEQ ID NO 20
<211> LENGTH: 22
<212> TYPE: DNA
<213> ORGANISM: Artificial Sequence

```
<220> FEATURE:
<223> OTHER INFORMATION: Synthetic GWLO91B6F12 primer

<400> SEQUENCE: 20
catttaatgg caccagggta ct                                        22

<210> SEQ ID NO 21
<211> LENGTH: 21
<212> TYPE: DNA
<213> ORGANISM: Artificial Sequence
<220> FEATURE:
<223> OTHER INFORMATION: Synthetic GWLO91F7F228 primer

<400> SEQUENCE: 21
acccgaaatt gcgaactatg a                                         21

<210> SEQ ID NO 22
<211> LENGTH: 20
<212> TYPE: DNA
<213> ORGANISM: Artificial Sequence
<220> FEATURE:
<223> OTHER INFORMATION: Synthetic GWLucRS873 primer

<400> SEQUENCE: 22
agtaaaacca aacgcattag                                           20

<210> SEQ ID NO 23
<211> LENGTH: 19
<212> TYPE: DNA
<213> ORGANISM: Artificial Sequence
<220> FEATURE:
<223> OTHER INFORMATION: Synthetic GWLucRS757 primer

<400> SEQUENCE: 23
aagggagggt gaacactga                                            19

<210> SEQ ID NO 24
<211> LENGTH: 21
<212> TYPE: DNA
<213> ORGANISM: Artificial Sequence
<220> FEATURE:
<223> OTHER INFORMATION: Synthetic GWLucRS601 primer

<400> SEQUENCE: 24
ccataaaatt gacgtacgac c                                         21

<210> SEQ ID NO 25
<211> LENGTH: 19
<212> TYPE: DNA
<213> ORGANISM: Artificial Sequence
<220> FEATURE:
<223> OTHER INFORMATION: Synthetic GWLucRS484 primer

<400> SEQUENCE: 25
ccaagaaggg caccagttt                                            19

<210> SEQ ID NO 26
<211> LENGTH: 21
<212> TYPE: DNA
<213> ORGANISM: Artificial Sequence
<220> FEATURE:
<223> OTHER INFORMATION: Synthetic GWLucScreenL primer

<400> SEQUENCE: 26
ttataatatc cagcatcacc a                                         21
```

-continued

```
<210> SEQ ID NO 27
<211> LENGTH: 19
<212> TYPE: DNA
<213> ORGANISM: Artificial Sequence
<220> FEATURE:
<223> OTHER INFORMATION: Synthetic GWLucRS326 primer

<400> SEQUENCE: 27
caacgaacca ttcaaatct                                                  19

<210> SEQ ID NO 28
<211> LENGTH: 23
<212> TYPE: DNA
<213> ORGANISM: Artificial Sequence
<220> FEATURE:
<223> OTHER INFORMATION: Synthetic GWLucRS182 primer

<400> SEQUENCE: 28
aatgcaaata atacttcacc acc                                             23

<210> SEQ ID NO 29
<211> LENGTH: 19
<212> TYPE: DNA
<213> ORGANISM: Artificial Sequence
<220> FEATURE:
<223> OTHER INFORMATION: Synthetic GWLucRS90 primer

<400> SEQUENCE: 29 gccacctta agatgcttg                                                   19

<210> SEQ ID NO 30
<211> LENGTH: 21
<212> TYPE: DNA
<213> ORGANISM: Artificial Sequence
<220> FEATURE:
<223> OTHER INFORMATION: Synthetic GWLucRS42 primer

<400> SEQUENCE: 30
aacattttgc cagctggatt c                                               21

<210> SEQ ID NO 31
<211> LENGTH: 20
<212> TYPE: DNA
<213> ORGANISM: Artificial Sequence
<220> FEATURE:
<223> OTHER INFORMATION: Synthetic A.tasLucORF-F primer

<400> SEQUENCE: 31
atgacttcta catctgtgga                                                 20

<210> SEQ ID NO 32
<211> LENGTH: 23
<212> TYPE: DNA
<213> ORGANISM: Artificial Sequence
<220> FEATURE:
<223> OTHER INFORMATION: Synthetic A.tasLucORF-R primer

<400> SEQUENCE: 32
ttacaatgtt gatcttaaaa tac                                             23

<210> SEQ ID NO 33
<211> LENGTH: 20
<212> TYPE: DNA
<213> ORGANISM: Artificial Sequence
<220> FEATURE:
<223> OTHER INFORMATION: Synthetic SMART-nF1 primer

<400> SEQUENCE: 33
```
aagcagtggt atcaacgcag                                              20

<210> SEQ ID NO 34
<211> LENGTH: 19
<212> TYPE: DNA
<213> ORGANISM: Artificial Sequence
<220> FEATURE:
<223> OTHER INFORMATION: Synthetic SMART-nF2 primer

<400> SEQUENCE: 34
caacgcagag tggccatta                                               19

<210> SEQ ID NO 35
<211> LENGTH: 18
<212> TYPE: DNA
<213> ORGANISM: Artificial Sequence
<220> FEATURE:
<223> OTHER INFORMATION: Synthetic CDSIII-R primer

<400> SEQUENCE: 35
attctagagg ccgaggcg                                                18

<210> SEQ ID NO 36
<211> LENGTH: 21
<212> TYPE: DNA
<213> ORGANISM: Artificial Sequence
<220> FEATURE:
<223> OTHER INFORMATION: Synthetic GWLucRS1120 primer

<400> SEQUENCE: 36
tggcttttct ggtgcattat c                                            21

<210> SEQ ID NO 37
<211> LENGTH: 20
<212> TYPE: DNA
<213> ORGANISM: Artificial Sequence
<220> FEATURE:
<223> OTHER INFORMATION: Synthetic GWLucRS1000 primer

<400> SEQUENCE: 37
cccgtagtac cagatgtcaa                                              20

<210> SEQ ID NO 38
<211> LENGTH: 18
<212> TYPE: DNA
<213> ORGANISM: Artificial Sequence
<220> FEATURE:
<223> OTHER INFORMATION: Synthetic GWLuc1E1R10 primer

<400> SEQUENCE: 38
catgtcggct tcagtcca                                                18

<210> SEQ ID NO 39
<211> LENGTH: 19
<212> TYPE: DNA
<213> ORGANISM: Artificial Sequence
<220> FEATURE:
<223> OTHER INFORMATION: Synthetic GWLucRS757 primer

<400> SEQUENCE: 39
aagggagggt gaacactga                                               19

<210> SEQ ID NO 40
<211> LENGTH: 20
<212> TYPE: DNA
<213> ORGANISM: Artificial Sequence

```
<220> FEATURE:
<223> OTHER INFORMATION: Synthetic GWLO91G12F236 primer

<400> SEQUENCE: 40
ttggtacact tatgcctgga                                              20

<210> SEQ ID NO 41
<211> LENGTH: 19
<212> TYPE: DNA
<213> ORGANISM: Artificial Sequence
<220> FEATURE:
<223> OTHER INFORMATION: Synthetic GWLO91C5F84 primer

<400> SEQUENCE: 41
caatcctgaa gcctccaaa                                               19

<210> SEQ ID NO 42
<211> LENGTH: 38
<212> TYPE: DNA
<213> ORGANISM: Artificial Sequence
<220> FEATURE:
<223> OTHER INFORMATION: Synthetic NHis-GWLuc#1 primer

<400> SEQUENCE: 42
gagaattcga ttgagggacg catggcttgt acttcagt                          38

<210> SEQ ID NO 43
<211> LENGTH: 30
<212> TYPE: DNA
<213> ORGANISM: Artificial Sequence
<220> FEATURE:
<223> OTHER INFORMATION: Synthetic AmpRCasSphlF primer

<400> SEQUENCE: 43
tagcgaagca tgcggtctga cagttaccaa                                   30

<210> SEQ ID NO 44
<211> LENGTH: 33
<212> TYPE: DNA
<213> ORGANISM: Artificial Sequence
<220> FEATURE:
<223> OTHER INFORMATION: Synthetic AmoRCasSphlR primer

<400> SEQUENCE: 44
cgtaagcgca tgctctaaat acattcaaat atg                               33

<210> SEQ ID NO 45
<211> LENGTH: 23
<212> TYPE: DNA
<213> ORGANISM: Artificial Sequence
<220> FEATURE:
<223> OTHER INFORMATION: Synthetic GWLuc1FHRV3C primer

<400> SEQUENCE: 45
gggacccatg gcttgtactt cag                                          23

<210> SEQ ID NO 46
<211> LENGTH: 546
<212> TYPE: PRT
<213> ORGANISM: Phrixothrix hirtus

<400> SEQUENCE: 46

Met Glu Glu Glu Asn Val Val Asn Gly Asp Arg Pro Arg Asp Leu Val
1               5                   10                  15

Phe Pro Gly Thr Ala Gly Leu Gln Leu Tyr Gln Ser Leu Tyr Lys Tyr
            20                  25                  30
```

```
Ser Tyr Ile Thr Asp Gly Ile Ile Asp Ala His Thr Asn Glu Val Ile
         35                  40                  45

Ser Tyr Ala Gln Ile Phe Glu Thr Ser Cys Arg Leu Ala Val Ser Leu
         50                  55                  60

Glu Lys Tyr Gly Leu Asp His Asn Asn Val Val Ala Ile Cys Ser Glu
 65                  70                  75                  80

Asn Asn Ile His Phe Phe Gly Pro Leu Ile Ala Ala Leu Tyr Gln Gly
                 85                  90                  95

Ile Pro Met Ala Thr Ser Asn Asp Met Tyr Thr Glu Arg Glu Met Ile
                100                 105                 110

Gly His Leu Asn Ile Ser Lys Pro Cys Leu Met Phe Cys Ser Lys Lys
             115                 120                 125

Ser Leu Pro Phe Ile Leu Lys Val Gln Lys His Leu Asp Phe Leu Lys
         130                 135                 140

Arg Val Ile Val Ile Asp Ser Met Tyr Asp Ile Asn Gly Val Glu Cys
145                 150                 155                 160

Val Phe Ser Phe Asp Ser Arg Asn Thr Asp His Ala Phe Asp Pro Val
                165                 170                 175

Lys Phe Asn Pro Lys Glu Phe Asp Pro Leu Glu Arg Thr Ala Leu Ile
                180                 185                 190

Met Thr Ser Ser Gly Thr Thr Gly Leu Pro Lys Gly Val Val Ile Ser
         195                 200                 205

His Arg Ser Ile Thr Ile Arg Phe Val His Ser Ser Asp Pro Ile Tyr
         210                 215                 220

Gly Thr Arg Ile Ala Pro Asp Thr Ser Ile Leu Ala Ile Ala Pro Phe
225                 230                 235                 240

His His Ala Phe Gly Leu Phe Thr Ala Leu Ala Tyr Phe Pro Val Gly
                245                 250                 255

Leu Lys Ile Val Met Val Lys Phe Glu Gly Glu Phe Phe Leu Lys
                260                 265                 270

Thr Ile Gln Asn Tyr Lys Ile Ala Ser Ile Val Val Pro Pro Pro Ile
         275                 280                 285

Met Val Tyr Leu Ala Lys Ser Pro Leu Val Asp Glu Tyr Asn Cys Ser
         290                 295                 300

Ser Leu Thr Glu Ile Ala Ser Gly Gly Ser Pro Leu Gly Arg Asp Ile
305                 310                 315                 320

Ala Asp Lys Val Ala Lys Arg Leu Lys Val His Gly Ile Leu Gln Gly
                325                 330                 335

Tyr Gly Leu Thr Glu Thr Cys Ser Ala Leu Ile Leu Ser Pro Asn Asp
             340                 345                 350

Arg Glu Leu Lys Lys Gly Ala Ile Gly Thr Pro Met Pro Tyr Val Gln
         355                 360                 365

Val Lys Val Ile Asp Ile Asn Thr Gly Lys Ala Leu Gly Pro Arg Glu
         370                 375                 380

Lys Gly Glu Ile Cys Phe Lys Ser Gln Met Leu Met Lys Gly Tyr His
385                 390                 395                 400

Asn Asn Pro Gln Ala Thr Arg Asp Ala Leu Asp Lys Asp Gly Trp Leu
                405                 410                 415

His Thr Gly Asp Leu Gly Tyr Tyr Asp Glu Asp Arg Phe Ile Tyr Val
             420                 425                 430

Val Asp Arg Leu Lys Glu Leu Ile Lys Tyr Lys Gly Tyr Gln Val Ala
         435                 440                 445

Pro Ala Glu Leu Glu Asn Leu Leu Leu Gln His Pro Asn Ile Ser Asp
```

```
                        450                 455                 460
Ala Gly Val Ile Glu Phe Arg Thr Asn Leu Leu Val Asn Tyr Leu Ser
465                 470                 475                 480

Ala Cys Val Val Leu Glu Pro Gly Lys Thr Met Thr Glu Lys Glu Val
                485                 490                 495

Gln Asp Tyr Ile Ala Glu Leu Val Thr Thr Lys His Leu Arg Gly
            500                 505                 510

Gly Val Val Phe Ile Asp Ser Ile Pro Lys Gly Pro Thr Gly Lys Leu
            515                 520                 525

Met Arg Asn Glu Leu Arg Ala Ile Phe Ala Arg Glu Gln Ala Lys Ser
    530                 535                 540

Lys Leu
545

<210> SEQ ID NO 47
<211> LENGTH: 545
<212> TYPE: PRT
<213> ORGANISM: Phrixothrix vivianii

<400> SEQUENCE: 47

Met Glu Glu Asn Ile Arg His Gly Glu Arg Pro Arg Asp Ile Val
1               5                   10                  15

His Pro Gly Ser Ala Gly Gln Gln Leu Tyr Gln Ser Leu Tyr Lys Phe
                20                  25                  30

Ala Ser Phe Pro Glu Ala Ile Ile Asp Ala His Thr Asn Glu Val Ile
            35                  40                  45

Ser Tyr Ala Gln Ile Phe Glu Thr Ser Cys Arg Leu Ala Val Ser Ile
50                  55                  60

Glu Gln Tyr Gly Leu Asn Glu Asn Val Val Gly Val Cys Ser Glu
65                  70                  75                  80

Asn Asn Ile Asn Phe Phe Asn Pro Val Leu Ala Ala Leu Tyr Leu Gly
                85                  90                  95

Ile Pro Val Ala Thr Ser Asn Asp Met Tyr Thr Asp Gly Glu Leu Thr
            100                 105                 110

Gly His Leu Asn Ile Ser Lys Pro Thr Ile Met Phe Ser Ser Lys Lys
        115                 120                 125

Ala Leu Pro Leu Ile Leu Arg Val Gln Gln Asn Leu Ser Phe Ile Lys
    130                 135                 140

Lys Val Val Ile Asp Ser Met Tyr Asp Ile Asn Gly Val Glu Cys
145                 150                 155                 160

Val Ser Thr Phe Val Ala Arg Tyr Thr Asp His Thr Phe Asp Pro Leu
                165                 170                 175

Ser Phe Thr Pro Lys Asp Phe Asp Pro Leu Glu Lys Ile Ala Leu Ile
            180                 185                 190

Met Ser Ser Ser Gly Thr Thr Gly Leu Pro Lys Gly Val Val Leu Ser
        195                 200                 205

His Arg Ser Leu Thr Ile Arg Phe Val His Ser Arg Asp Pro Ile Tyr
    210                 215                 220

Gly Thr Arg Thr Val Pro Gln Thr Ser Ile Leu Ser Leu Val Pro Phe
225                 230                 235                 240

His His Ala Phe Gly Met Phe Thr Thr Leu Ser Tyr Phe Val Val Gly
                245                 250                 255

Leu Lys Val Val Met Leu Lys Lys Phe Glu Gly Ala Leu Phe Leu Lys
            260                 265                 270

Thr Ile Gln Asn Tyr Lys Ile Pro Thr Ile Val Val Ala Pro Pro Val
```

```
                275                 280                 285
Met Val Phe Leu Ala Lys Ser Pro Leu Val Asp Gln Tyr Asp Leu Ser
290                 295                 300

Ser Leu Thr Glu Val Ala Thr Gly Gly Ala Pro Leu Gly Lys Asp Val
305                 310                 315                 320

Ala Glu Ala Val Ala Lys Arg Leu Lys Leu Pro Gly Ile Ile Gln Gly
                325                 330                 335

Tyr Gly Leu Thr Glu Thr Cys Cys Ala Val Met Ile Thr Pro His Asn
                340                 345                 350

Ala Val Lys Thr Gly Ser Thr Gly Arg Pro Leu Pro Tyr Ile Lys Ala
                355                 360                 365

Lys Val Leu Asp Asn Ala Thr Gly Lys Ala Leu Gly Pro Gly Glu Arg
            370                 375                 380

Gly Glu Ile Cys Phe Gln Ser Glu Met Ile Met Lys Gly Tyr Tyr Asn
385                 390                 395                 400

Asn Pro Glu Ala Thr Ile Asp Thr Ile Asp Lys Asp Gly Trp Leu His
                405                 410                 415

Ser Gly Asp Ile Gly Tyr Tyr Asp Glu Asp Gly Asn Phe Phe Ile Val
                420                 425                 430

Asp Arg Leu Lys Glu Leu Ile Lys Tyr Lys Gly Tyr Gln Val Ala Pro
            435                 440                 445

Ala Glu Leu Glu Asn Leu Leu Leu Gln His Pro Ser Ile Ala Asp Ala
450                 455                 460

Gly Val Thr Gly Val Pro Asp Glu Phe Gly Gly Gln Leu Pro Ala Ala
465                 470                 475                 480

Cys Val Val Leu Glu Ser Gly Lys Thr Leu Thr Glu Lys Glu Val Gln
                485                 490                 495

Asp Phe Ile Ala Ala Gln Val Thr Pro Thr Lys His Leu Arg Gly Gly
                500                 505                 510

Val Val Phe Val Asp Ser Ile Pro Lys Gly Pro Thr Gly Lys Leu Ile
                515                 520                 525

Arg Lys Glu Leu Arg Glu Ile Phe Ala Gln Arg Ala Pro Lys Ser Lys
            530                 535                 540

Leu
545

<210> SEQ ID NO 48
<211> LENGTH: 547
<212> TYPE: PRT
<213> ORGANISM: Lampyris noctiluca

<400> SEQUENCE: 48

Met Glu Asp Ala Lys Asn Ile Met His Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Gln Val Pro Gly Thr Ile Ala Phe Thr Asp Ala His Ala Glu
        35                  40                  45

Val Asn Ile Thr Tyr Ser Glu Tyr Phe Glu Met Ala Cys Arg Leu Ala
    50                  55                  60

Glu Thr Met Lys Arg Tyr Gly Leu Gly Leu Gln His His Ile Ala Val
65                  70                  75                  80

Cys Ser Glu Asn Ser Leu Gln Phe Phe Met Pro Val Cys Gly Ala Leu
                85                  90                  95

Phe Ile Gly Val Gly Val Ala Ser Thr Asn Asp Ile Tyr Asn Glu Arg
            100                 105                 110
```

-continued

```
Glu Leu Tyr Asn Ser Leu Ser Ile Ser Gln Pro Thr Ile Val Ser Cys
            115                 120                 125

Ser Lys Arg Ala Leu Gln Lys Ile Leu Gly Val Gln Lys Lys Leu Pro
    130                 135                 140

Ile Ile Gln Lys Ile Val Ile Leu Asp Ser Arg Glu Asp Tyr Met Gly
145                 150                 155                 160

Lys Gln Ser Met Tyr Ser Phe Ile Glu Ser His Leu Pro Ala Gly Phe
                165                 170                 175

Asn Glu Tyr Asp Tyr Ile Pro Asp Ser Phe Asp Arg Glu Thr Ala Thr
            180                 185                 190

Ala Leu Ile Met Asn Ser Ser Gly Ser Thr Gly Leu Pro Lys Gly Val
            195                 200                 205

Glu Leu Thr His Gln Asn Val Cys Val Arg Phe Ser His Cys Arg Asp
            210                 215                 220

Pro Val Phe Gly Asn Gln Ile Ile Pro Asp Thr Ala Ile Leu Thr Val
225                 230                 235                 240

Ile Pro Phe His His Gly Phe Gly Met Phe Thr Thr Leu Gly Tyr Leu
                245                 250                 255

Thr Cys Gly Phe Arg Ile Val Leu Met Tyr Arg Phe Glu Glu Glu Leu
                260                 265                 270

Phe Leu Arg Ser Leu Gln Asp Tyr Lys Ile Gln Ser Ala Leu Leu Val
            275                 280                 285

Pro Thr Leu Phe Ser Phe Phe Ala Lys Ser Thr Leu Val Asp Lys Tyr
            290                 295                 300

Asp Leu Ser Asn Leu His Glu Ile Ala Ser Gly Gly Ala Pro Leu Ala
305                 310                 315                 320

Lys Glu Val Gly Glu Ala Val Ala Lys Arg Phe Lys Leu Pro Gly Ile
                325                 330                 335

Arg Gln Gly Tyr Gly Leu Thr Glu Thr Thr Ser Ala Ile Ile Ile Thr
            340                 345                 350

Pro Glu Gly Asp Asp Lys Pro Gly Ala Cys Gly Lys Val Val Pro Phe
            355                 360                 365

Phe Ser Ala Lys Ile Val Asp Leu Asp Thr Gly Lys Thr Leu Gly Val
            370                 375                 380

Asn Gln Arg Gly Glu Leu Cys Val Lys Gly Pro Met Ile Met Lys Gly
385                 390                 395                 400

Tyr Val Asn Asn Pro Glu Ala Thr Ser Ala Leu Ile Asp Lys Asp Gly
                405                 410                 415

Trp Leu His Ser Gly Asp Ile Ala Tyr Tyr Asp Lys Asp Gly His Phe
            420                 425                 430

Phe Ile Val Asp Arg Leu Lys Ser Leu Ile Lys Tyr Lys Gly Tyr Gln
            435                 440                 445

Val Pro Pro Ala Glu Leu Glu Ser Ile Leu Leu Gln His Pro Phe Ile
450                 455                 460

Phe Asp Ala Gly Val Ala Gly Ile Pro Asp Pro Asp Ala Gly Glu Leu
465                 470                 475                 480

Pro Ala Ala Val Val Val Leu Glu Glu Gly Lys Thr Met Thr Glu Gln
                485                 490                 495

Glu Val Met Asp Tyr Val Ala Gly Gln Val Thr Ala Ser Lys Arg Leu
            500                 505                 510

Arg Gly Gly Val Lys Phe Val Asp Glu Val Pro Lys Gly Leu Thr Gly
            515                 520                 525

Lys Ile Asp Gly Arg Lys Ile Arg Glu Ile Leu Met Met Gly Lys Lys
```

Ser Lys Leu
545

<210> SEQ ID NO 49
<211> LENGTH: 547
<212> TYPE: PRT
<213> ORGANISM: Lampyris turkestanica

<400> SEQUENCE: 49

Met Glu Asp Ala Lys Asn Ile Met His Gly Pro Pro Phe Tyr Pro
1               5                   10                  15

Leu Glu Asp Gly Thr Ala Gly Glu Gln Leu His Lys Ala Met Lys Arg
            20                  25                  30

Tyr Ala Gln Val Pro Gly Thr Ile Ala Phe Thr Asp Ala His Ala Glu
        35                  40                  45

Val Asn Ile Thr Tyr Ser Glu Tyr Phe Glu Met Ala Cys Arg Leu Ala
50                  55                  60

Glu Thr Met Lys Arg Tyr Gly Leu Gly Leu Gln His His Ile Ala Val
65                  70                  75                  80

Cys Ser Glu Asn Ser Leu Gln Phe Phe Met Pro Val Cys Gly Ala Leu
                85                  90                  95

Phe Ile Gly Val Gly Val Ala Pro Thr Asn Asp Ile Tyr Asn Glu Arg
            100                 105                 110

Glu Leu Tyr Asn Ser Leu Ser Ile Ser Gln Pro Thr Ile Val Phe Cys
        115                 120                 125

Ser Lys Arg Ala Leu Gln Lys Ile Leu Gly Val Gln Lys Lys Leu Pro
130                 135                 140

Ile Ile Gln Lys Ile Val Ile Leu Asp Ser Arg Glu Asp Tyr Met Gly
145                 150                 155                 160

Lys Gln Ser Met Tyr Ser Phe Ile Glu Ser His Leu Pro Ala Gly Phe
                165                 170                 175

Asn Glu Tyr Asp Tyr Ile Pro Asp Ser Phe Asp Arg Glu Thr Ala Thr
            180                 185                 190

Ala Leu Ile Met Asn Ser Ser Gly Ser Thr Gly Leu Pro Lys Gly Val
        195                 200                 205

Glu Leu Thr His Lys Asn Ile Cys Val Arg Phe Ser His Cys Arg Asp
210                 215                 220

Pro Val Phe Gly Asn Gln Ile Ile Pro Asp Thr Ala Ile Leu Thr Val
225                 230                 235                 240

Ile Pro Phe His His Gly Phe Gly Met Phe Thr Thr Leu Gly Tyr Leu
                245                 250                 255

Thr Cys Gly Phe Arg Ile Val Leu Met Tyr Arg Cys Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Val Asp Lys Tyr
290                 295                 300

Asp Leu Ser Asn Leu His Glu Ile Ala Ser Gly Gly Ala Pro Leu Ala
305                 310                 315                 320

Lys Glu Val Gly Glu Ala Val Ala Lys Arg Phe Lys Leu Pro Gly Ile
                325                 330                 335

Arg Gln Gly Tyr Gly Leu Thr Glu Thr Thr Ser Ala Ile Ile Ile Thr
            340                 345                 350

Pro Glu Gly Asp Asp Lys Pro Gly Ala Cys Gly Lys Val Val Pro Phe

```
                355                 360                 365
Phe Ser Ala Lys Ile Val Asp Leu Asp Thr Gly Lys Thr Leu Gly Val
370                 375                 380

Asn Gln Arg Gly Glu Leu Cys Val Lys Gly Pro Met Ile Met Lys Gly
385                 390                 395                 400

Tyr Val Asn Asn Pro Glu Ala Thr Ser Ala Leu Ile Asp Lys Asp Gly
                405                 410                 415

Trp Leu His Ser Gly Asp Ile Ala Tyr Tyr Asp Lys Asp Gly His Phe
            420                 425                 430

Phe Ile Val Asp Arg Leu Lys Ser Leu Ile Lys Tyr Lys Gly Tyr Gln
            435                 440                 445

Val Pro Pro Ala Glu Leu Glu Ser Ile Leu Leu Gln His Pro Phe Ile
450                 455                 460

Phe Asp Ala Gly Val Ala Gly Ile Pro Asp Pro Asp Ala Gly Glu Leu
465                 470                 475                 480

Pro Ala Ala Val Val Val Leu Glu Glu Gly Lys Thr Met Thr Glu Gln
                485                 490                 495

Glu Val Met Asp Tyr Val Ala Gly Gln Val Thr Ala Ser Lys Arg Leu
            500                 505                 510

Arg Gly Gly Val Lys Phe Val Asp Glu Val Pro Lys Gly Leu Thr Gly
            515                 520                 525

Lys Ile Asp Ala Arg Lys Ile Arg Glu Ile Leu Met Met Gly Lys Lys
530                 535                 540

Ser Lys Leu
545

<210> SEQ ID NO 50
<211> LENGTH: 548
<212> TYPE: PRT
<213> ORGANISM: Pyrocoelia miyako

<400> SEQUENCE: 50

Met Glu Asp Asp Ser Lys His Ile Met His Gly His Arg His Ser Ile
1               5                   10                  15

Leu Trp Glu Asp Gly Thr Ala Gly Glu Gln Leu His Lys Ala Met Lys
                20                  25                  30

Arg Tyr Ala Gln Val Pro Gly Thr Ile Ala Phe Thr Asp Ala His Ala
            35                  40                  45

Glu Val Asn Ile Thr Tyr Ser Glu Tyr Phe Glu Met Ser Cys Arg Leu
        50                  55                  60

Ala Glu Thr Met Lys Arg Tyr Gly Leu Gly Leu Gln His His Ile Ala
65                  70                  75                  80

Val Cys Ser Glu Thr Ser Leu Gln Phe Phe Met Pro Val Cys Gly Ala
                85                  90                  95

Leu Phe Ile Gly Val Gly Val Ala Pro Thr Asn Asp Ile Tyr Asn Glu
                100                 105                 110

Arg Glu Leu Tyr Asn Ser Leu Phe Ile Ser Gln Pro Thr Ile Val Phe
            115                 120                 125

Cys Ser Lys Arg Ala Leu Gln Lys Ile Leu Gly Val Gln Lys Lys Leu
        130                 135                 140

Pro Val Ile Gln Lys Ile Val Ile Leu Asp Ser Arg Glu Asp Tyr Met
145                 150                 155                 160

Gly Lys Gln Ser Met Tyr Ser Phe Ile Glu Ser His Leu Pro Ala Gly
                165                 170                 175

Phe Asn Glu Tyr Asp Tyr Ile Pro Asp Ser Phe Asp Arg Glu Thr Ala
```

```
                        180                 185                 190
Thr Ala Leu Ile Met Asn Ser Ser Gly Ser Thr Gly Leu Pro Lys Gly
            195                 200                 205

Val Asp Leu Thr His Met Asn Val Cys Val Arg Phe Ser His Cys Arg
        210                 215                 220

Asp Pro Val Phe Gly Asn Gln Ile Ile Pro Asp Thr Ala Ile Leu Thr
225                 230                 235                 240

Val Ile Pro Phe His His Val Phe Gln Met Phe Thr Thr Leu Gly Tyr
                245                 250                 255

Leu Thr Cys Gly Phe Arg Ile Val Leu Met Tyr Arg Phe Glu Glu Glu
            260                 265                 270

Leu Phe Leu Arg Ser Leu Gln Asp Tyr Lys Ile Gln Ser Ala Leu Leu
        275                 280                 285

Val Pro Thr Leu Phe Ser Phe Ala Lys Ser Thr Leu Val Asp Lys
290                 295                 300

Tyr Asp Leu Ser Asn Leu His Glu Ile Ala Ser Gly Gly Ala Pro Leu
305                 310                 315                 320

Ala Lys Glu Val Gly Glu Ala Val Ala Lys Arg Phe Lys Leu Pro Gly
                325                 330                 335

Ile Arg Gln Gly Tyr Gly Leu Thr Glu Thr Thr Ser Ala Ile Ile Ile
            340                 345                 350

Thr Pro Glu Gly Asp Asp Lys Pro Gly Ala Cys Gly Lys Val Val Pro
        355                 360                 365

Phe Phe Thr Ala Lys Ile Val Asp Leu Asp Thr Gly Lys Thr Leu Gly
370                 375                 380

Val Asn Gln Arg Gly Glu Leu Cys Val Lys Gly Pro Met Ile Met Lys
385                 390                 395                 400

Gly Tyr Val Asn Asn Pro Glu Ala Thr Asn Ala Leu Ile Asp Lys Asp
                405                 410                 415

Gly Trp Leu His Ser Gly Asp Ile Ala Tyr Tyr Asp Lys Asp Gly His
            420                 425                 430

Phe Phe Ile Val Asp Arg Leu Lys Ser Leu Ile Lys Tyr Lys Gly Tyr
        435                 440                 445

Gln Val Pro Pro Ala Glu Leu Glu Ser Ile Leu Leu Gln His Pro Phe
    450                 455                 460

Ile Phe Asp Ala Gly Val Ala Gly Ile Pro Asp Pro Asp Ala Gly Glu
465                 470                 475                 480

Leu Pro Ala Ala Val Val Leu Glu Glu Gly Lys Met Met Thr Glu
                485                 490                 495

Gln Glu Val Met Asp Tyr Val Ala Gly Gln Val Thr Ala Ser Lys Arg
            500                 505                 510

Leu Arg Gly Gly Val Lys Phe Val Asp Glu Val Pro Lys Gly Leu Thr
        515                 520                 525

Gly Lys Ile Asp Ser Arg Lys Ile Arg Glu Ile Leu Thr Met Gly Gln
    530                 535                 540

Lys Ser Lys Leu
545

<210> SEQ ID NO 51
<211> LENGTH: 548
<212> TYPE: PRT
<213> ORGANISM: Pyrocoelia rufa

<400> SEQUENCE: 51

Met Glu Asp Asp Ser Lys His Ile Met His Gly His Arg His Ser Ile
```

```
1               5                   10                  15
Leu Trp Glu Asp Gly Thr Ala Gly Glu Gln Leu His Lys Ala Met Lys
                20                  25                  30

Arg Tyr Ala Gln Val Pro Gly Thr Ile Ala Phe Thr Asp Ala His Ala
                35                  40                  45

Glu Val Asn Ile Thr Tyr Ser Glu Tyr Phe Glu Met Ser Cys Arg Leu
            50                  55              60

Ala Glu Thr Met Lys Arg Tyr Gly Leu Gly Leu Gln His His Ile Ala
65                  70                  75                  80

Val Cys Ser Glu Asn Ser Leu Gln Phe Phe Met Pro Val Cys Gly Ala
                85                  90                  95

Leu Phe Ile Gly Val Gly Val Ala Pro Thr Asn Asp Ile Tyr Asn Glu
                100                 105                 110

Arg Glu Leu Tyr Asn Ser Leu Phe Ile Ser Gln Pro Thr Ile Val Phe
            115                 120                 125

Cys Ser Lys Arg Ala Leu Gln Lys Ile Leu Gly Val His Lys Lys Leu
            130                 135                 140

Pro Val Ile Gln Lys Ile Val Ile Leu Asp Ser Arg Glu Asp Tyr Met
145                 150                 155                 160

Gly Lys Gln Ser Met Tyr Ser Phe Ile Glu Ser His Leu Pro Ala Gly
                165                 170                 175

Phe Asn Glu Tyr Asp Tyr Ile Pro Asp Ser Phe Asp Arg Glu Thr Ala
                180                 185                 190

Thr Ala Leu Ile Met Asn Ser Ser Gly Ser Thr Gly Leu Pro Lys Gly
                195                 200                 205

Val Asp Leu Thr His Met Asn Val Cys Val Arg Phe Ser His Cys Arg
    210                 215                 220

Asp Pro Val Phe Gly Asn Gln Ile Ile Pro Asp Thr Ala Ile Leu Thr
225                 230                 235                 240

Val Ile Pro Phe His His Gly Phe Gly Met Phe Thr Thr Leu Gly Tyr
                245                 250                 255

Leu Thr Cys Gly Phe Arg Ile Val Leu Met Tyr Arg Phe Glu Glu Glu
                260                 265                 270

Leu Phe Leu Arg Ser Leu Gln Asp Tyr Lys Ile Gln Ser Ala Leu Leu
            275                 280                 285

Val Pro Thr Leu Phe Ser Phe Phe Ala Lys Ser Thr Leu Val Asp Lys
            290                 295                 300

Tyr Asp Leu Ser Asn Leu His Glu Ile Ala Ser Gly Gly Ala Pro Leu
305                 310                 315                 320

Ala Lys Glu Val Gly Glu Ala Val Ala Lys Arg Phe Lys Leu Pro Gly
                325                 330                 335

Ile Arg Gln Gly Asp Gly Leu Thr Glu Thr Thr Ser Ala Ile Ile Ile
                340                 345                 350

Thr Pro Glu Gly Asp Asp Lys Pro Gly Ala Cys Gly Lys Val Val Pro
            355                 360                 365

Phe Phe Ala Ala Lys Ile Val Asp Leu Asp Thr Gly Lys Thr Leu Gly
            370                 375                 380

Val Asn Gln Arg Gly Glu Leu Cys Val Lys Gly Pro Met Ile Met Lys
385                 390                 395                 400

Gly Tyr Val Asn Asn Pro Glu Ala Thr Asn Ala Leu Ile Asp Lys Asp
                405                 410                 415

Gly Trp Leu His Ser Gly Asp Ile Ala Tyr Tyr Asp Lys Asp Gly His
                420                 425                 430
```

```
Phe Phe Ile Val Asp Arg Leu Lys Ser Leu Ile Lys Tyr Lys Gly Tyr
        435                 440                 445

Gln Val Pro Pro Ala Glu Leu Glu Ser Ile Leu Leu Gln His Pro Phe
    450                 455                 460

Ile Phe Asp Ala Gly Val Ala Gly Ile Pro Asp Pro Asp Ala Gly Glu
465                 470                 475                 480

Leu Pro Ala Ala Val Val Leu Glu Glu Gly Lys Met Met Thr Glu
                485                 490                 495

Gln Glu Val Met Asp Tyr Val Ala Gly Gln Val Thr Ala Ser Lys Arg
                500                 505                 510

Leu Arg Gly Gly Val Lys Phe Val Asp Glu Val Pro Lys Gly Leu Thr
515                 520                 525

Gly Lys Ile Asp Ser Arg Lys Ile Arg Glu Ile Leu Thr Met Gly Gln
    530                 535                 540

Lys Ser Lys Leu
545

<210> SEQ ID NO 52
<211> LENGTH: 547
<212> TYPE: PRT
<213> ORGANISM: Cratomorphus distinctus

<400> SEQUENCE: 52

Met Glu Glu Asp Lys Asn Ile Met Tyr Gly Pro Ala Pro Phe Ser Pro
1               5                   10                  15

Leu Glu Glu Gly Thr Ala Gly Glu Gln Leu His Lys Ala Met Lys Arg
            20                  25                  30

Tyr Ala Gln Ile Pro Gly Thr Ile Ala Phe Thr Ala Ala His Val Glu
        35                  40                  45

Val Asn Val Thr Tyr Ala Glu Tyr Phe Glu Met Ala Cys Arg Leu Ala
    50                  55                  60

Glu Thr Met Lys Arg Tyr Gly Leu Gly Leu Asp His Arg Ile Ala Val
65                  70                  75                  80

Cys Ser Glu Asn Ser Leu Gln Phe Phe Met Pro Val Cys Gly Ala Leu
                85                  90                  95

Phe Ile Gly Val Gly Val Ala Pro Thr Asn Asp Ile Tyr Asn Glu Arg
            100                 105                 110

Glu Leu Tyr Asn Ser Leu Ser Ile Ser Gln Pro Thr Val Val Phe Cys
        115                 120                 125

Ser Lys Arg Ala Leu Gln Lys Ile Leu Gly Val Gln Lys Ser Leu Pro
    130                 135                 140

Val Ile Lys Lys Ile Val Ile Leu Asp Ser Arg Glu Asp Tyr Met Gly
145                 150                 155                 160

Lys Gln Ser Met Tyr Ser Phe Ile Gln Ser Tyr Leu Pro Gly Gly Phe
                165                 170                 175

Asn Glu Tyr Asp Tyr Val Pro Asp Thr Phe Asp Arg Asp Met Ala Thr
            180                 185                 190

Ala Leu Ile Met Asn Ser Ser Gly Ser Thr Gly Leu Pro Lys Gly Val
        195                 200                 205

Glu Leu Ser His Lys Asn Val Cys Val Arg Phe Ser His Cys Arg Asp
    210                 215                 220

Pro Val Phe Gly Asn Gln Ile Ile Pro Asp Thr Ala Ile Leu Thr Val
225                 230                 235                 240

Ile Pro Phe His His Gly Phe Gly Met Phe Thr Thr Leu Gly Tyr Leu
                245                 250                 255
```

```
Thr Cys Gly Phe Arg Ile Val Leu Met Tyr Arg Phe Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Val Asp Lys Tyr
290                 295                 300

Asp Leu Ser Asn Leu His Glu Ile Ala Ser Gly Gly Ala Pro Leu Ala
305                 310                 315                 320

Lys Glu Val Gly Glu Ala Val Ala Lys Arg Phe Lys Leu Pro Gly Ile
                325                 330                 335

Arg Gln Gly Tyr Gly Leu Thr Glu Thr Thr Ser Ala Ile Ile Ile Thr
            340                 345                 350

Pro Glu Gly Asp Asp Lys Pro Gly Ala Cys Gly Lys Val Val Pro Phe
        355                 360                 365

Phe Ala Ala Lys Ile Val Asp Leu Asp Thr Gly Lys Thr Leu Gly Val
370                 375                 380

Asn Gln Arg Gly Glu Leu Tyr Val Lys Gly Pro Met Ile Met Lys Gly
385                 390                 395                 400

Tyr Val Asn Asn Pro Glu Ala Thr Asn Ala Leu Ile Asp Lys Asp Gly
                405                 410                 415

Trp Leu Arg Ser Gly Asp Ile Ala Tyr Tyr Asp Glu Asp Gly His Val
            420                 425                 430

Phe Ile Val Asp Arg Leu Lys Ser Leu Ile Lys Tyr Lys Gly Tyr Gln
        435                 440                 445

Val Pro Pro Ala Glu Leu Glu Ser Ile Leu Leu Gln His Pro Phe Ile
450                 455                 460

Phe Asp Ala Gly Val Ala Gly Ile Pro Asp Glu Asp Ala Gly Glu Leu
465                 470                 475                 480

Pro Ala Ala Val Val Val Leu Glu Glu Gly Lys Thr Met Thr Glu Gln
                485                 490                 495

Glu Val Met Asp Tyr Val Ala Gly Gln Val Thr Ala Ser Lys Arg Leu
            500                 505                 510

Arg Gly Gly Val Lys Phe Val Asp Glu Val Pro Lys Gly Leu Thr Gly
        515                 520                 525

Lys Ile Asp Ser Arg Lys Ile Arg Glu Ile Leu Val Met Gly Lys Lys
530                 535                 540

Ser Lys Leu
545

<210> SEQ ID NO 53
<211> LENGTH: 550
<212> TYPE: PRT
<213> ORGANISM: Photinus pyralis

<400> SEQUENCE: 53

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
50                  55                  60

Glu Ala Met Lys Arg Tyr Gly Leu Asn Thr Asn His Arg Ile Val Val
65                  70                  75                  80
```

```
Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510
```

```
Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
            530                 535                 540

Gly Gly Lys Ser Lys Leu
545                 550

<210> SEQ ID NO 54
<211> LENGTH: 548
<212> TYPE: PRT
<213> ORGANISM: Luciola cruciata

<400> SEQUENCE: 54

Met Glu Asn Met Glu Asn Asp Glu Asn Ile Val Val Gly Pro Lys Pro
1               5                   10                  15

Phe Tyr Pro Ile Glu Glu Gly Ser Ala Gly Thr Gln Leu Arg Lys Tyr
            20                  25                  30

Met Glu Arg Tyr Ala Lys Leu Gly Ala Ile Ala Phe Thr Asn Ala Val
            35                  40                  45

Thr Gly Val Asp Tyr Ser Tyr Ala Glu Tyr Leu Glu Lys Ser Cys Cys
    50                  55                  60

Leu Gly Lys Ala Leu Gln Asn Tyr Gly Leu Val Val Asp Gly Arg Ile
65                  70                  75                  80

Ala Leu Cys Ser Glu Asn Cys Glu Glu Phe Phe Ile Pro Val Ile Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
            115                 120                 125

Phe Ser Ser Lys Lys Gly Leu Asp Lys Val Ile Thr Val Gln Lys Thr
        130                 135                 140

Val Thr Thr Ile Lys Thr Ile Val Ile Leu Asp Ser Lys Val Asp Tyr
145                 150                 155                 160

Arg Gly Tyr Gln Cys Leu Asp Thr Phe Ile Lys Arg Asn Thr Pro Pro
                165                 170                 175

Gly Phe Gln Ala Ser Ser Phe Lys Thr Val Glu Val Asp Arg Lys Glu
            180                 185                 190

Gln Val Ala Leu Ile Met Asn Ser Ser Gly Ser Thr Gly Leu Pro Lys
            195                 200                 205

Gly Val Gln Leu Thr His Glu Asn Thr Val Thr Arg Phe Ser His Ala
        210                 215                 220

Arg Asp Pro Ile Tyr Gly Asn Gln Val Ser Pro Gly Thr Ala Val Leu
225                 230                 235                 240

Thr Val Val Pro Phe His His Gly Phe Gly Met Phe Thr Thr Leu Gly
                245                 250                 255

Tyr Leu Ile Cys Gly Phe Arg Val Val Met Leu Thr Lys Phe Asp Glu
            260                 265                 270

Glu Thr Phe Leu Lys Thr Leu Gln Asp Tyr Lys Cys Thr Ser Val Ile
            275                 280                 285

Leu Val Pro Thr Leu Phe Ala Ile Leu Asn Lys Ser Glu Leu Leu Asn
        290                 295                 300

Lys Tyr Asp Leu Ser Asn Leu Val Glu Ile Ala Ser Gly Gly Ala Pro
305                 310                 315                 320

Leu Ser Lys Glu Val Gly Glu Ala Val Ala Arg Arg Phe Asn Leu Pro
                325                 330                 335
```

Gly Val Arg Gln Gly Tyr Gly Leu Thr Glu Thr Thr Ser Ala Ile Ile
                340                 345                 350

Ile Thr Pro Glu Gly Asp Asp Lys Pro Gly Ala Ser Gly Lys Val Val
            355                 360                 365

Pro Leu Phe Lys Ala Lys Val Ile Asp Leu Asp Thr Lys Lys Ser Leu
            370                 375                 380

Gly Pro Asn Arg Arg Gly Glu Val Cys Val Lys Gly Pro Met Leu Met
385                 390                 395                 400

Lys Gly Tyr Val Asn Asn Pro Glu Ala Thr Lys Glu Leu Ile Asp Glu
            405                 410                 415

Glu Gly Trp Leu His Thr Gly Asp Ile Gly Tyr Tyr Asp Glu Glu Lys
            420                 425                 430

His Phe Phe Ile Val Asp Arg Leu Lys Ser Leu Ile Lys Tyr Lys Gly
            435                 440                 445

Tyr Gln Val Pro Pro Ala Glu Leu Glu Ser Val Leu Leu Gln His Pro
        450                 455                 460

Ser Ile Phe Asp Ala Gly Val Ala Gly Val Pro Asp Pro Val Ala Gly
465                 470                 475                 480

Glu Leu Pro Gly Ala Val Val Val Leu Glu Ser Gly Lys Asn Met Thr
                485                 490                 495

Glu Lys Glu Val Met Asp Tyr Val Ala Ser Gln Val Ser Asn Ala Lys
            500                 505                 510

Arg Leu Arg Gly Gly Val Arg Phe Val Asp Glu Val Pro Lys Gly Leu
            515                 520                 525

Thr Gly Lys Ile Asp Gly Arg Ala Ile Arg Glu Ile Leu Lys Lys Pro
        530                 535                 540

Val Ala Lys Met
545

<210> SEQ ID NO 55
<211> LENGTH: 548
<212> TYPE: PRT
<213> ORGANISM: Luciola lateralis

<400> SEQUENCE: 55

Met Glu Asn Met Glu Asn Asp Glu Asn Ile Val Tyr Gly Pro Glu Pro
1               5                   10                  15

Phe Tyr Pro Ile Glu Glu Gly Ser Ala Gly Ala Gln Leu Arg Lys Tyr
            20                  25                  30

Met Asp Arg Tyr Ala Lys Leu Gly Ala Ile Ala Phe Thr Asn Ala Leu
        35                  40                  45

Thr Gly Val Asp Tyr Thr Tyr Ala Glu Tyr Leu Glu Lys Ser Cys Cys
    50                  55                  60

Leu Gly Glu Ala Leu Lys Asn Tyr Gly Leu Val Val Asp Gly Arg Ile
65                  70                  75                  80

Ala Leu Cys Ser Glu Asn Cys Glu Glu Phe Phe Ile Pro Val Leu Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Ala Ile Lys Thr Ile Val Ile Leu Asp Ser Lys Val Asp Tyr
145                 150                 155                 160

-continued

Arg Gly Tyr Gln Ser Met Asp Asn Phe Ile Lys Lys Asn Thr Pro Gln
              165                 170                 175

Gly Phe Lys Gly Ser Ser Phe Lys Thr Val Glu Val Asn Arg Lys Glu
          180                 185                 190

Gln Val Ala Leu Ile Met Asn Ser Ser Gly Ser Thr Gly Leu Pro Lys
          195                 200                 205

Gly Val Gln Leu Thr His Glu Asn Ala Val Thr Arg Phe Ser His Ala
210                 215                 220

Arg Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
              245                 250                 255

Tyr Leu Thr Cys Gly Phe Arg Ile Val Met Leu Thr Lys Phe Asp Glu
              260                 265                 270

Glu Thr Phe Leu Lys Thr Leu Gln Asp Tyr Lys Cys Ser Ser Val Ile
          275                 280                 285

Leu Val Pro Thr Leu Phe Ala Ile Leu Asn Arg Ser Glu Leu Leu Asp
          290                 295                 300

Lys Tyr Asp Leu Ser Asn Leu Val Glu Ile Ala Ser Gly Gly Ala Pro
305                 310                 315                 320

Leu Ser Lys Glu Ile Gly Glu Ala Val Ala Arg Arg Phe Asn Leu Pro
              325                 330                 335

Gly Val Arg Gln Gly Tyr Gly Leu Thr Glu Thr Thr Ser Ala Ile Ile
              340                 345                 350

Ile Thr Pro Glu Gly Asp Asp Lys Pro Gly Ala Ser Gly Lys Val Val
          355                 360                 365

Pro Leu Phe Lys Ala Lys Val Ile Asp Leu Asp Thr Lys Lys Thr Leu
          370                 375                 380

Gly Pro Asn Arg Arg Gly Glu Val Cys Val Lys Gly Pro Met Leu Met
385                 390                 395                 400

Lys Gly Tyr Val Asp Asn Pro Glu Ala Thr Arg Glu Ile Ile Asp Glu
              405                 410                 415

Glu Gly Trp Leu His Thr Gly Asp Ile Gly Tyr Tyr Asp Glu Glu Lys
              420                 425                 430

His Phe Phe Ile Val Asp Arg Leu Lys Ser Leu Ile Lys Tyr Lys Gly
          435                 440                 445

Tyr Gln Val Pro Pro Ala Glu Leu Glu Ser Val Leu Leu Gln His Pro
          450                 455                 460

Asn Ile Phe Asp Ala Gly Val Ala Gly Val Pro Asp Pro Ile Ala Gly
465                 470                 475                 480

Glu Leu Pro Gly Ala Val Val Val Leu Glu Lys Gly Lys Ser Met Thr
              485                 490                 495

Glu Lys Glu Val Met Asp Tyr Val Ala Ser Gln Val Ser Asn Ala Lys
          500                 505                 510

Arg Leu Arg Gly Gly Val Arg Phe Val Asp Glu Val Pro Lys Gly Leu
          515                 520                 525

Thr Gly Lys Ile Asp Gly Lys Ala Ile Arg Glu Ile Leu Lys Lys Pro
          530                 535                 540

Val Ala Lys Met
545

<210> SEQ ID NO 56
<211> LENGTH: 548
<212> TYPE: PRT

<213> ORGANISM: Hotaria unmunsana

<400> SEQUENCE: 56

```
Met Glu Met Glu Lys Glu Asn Val Val Tyr Gly Pro Leu Pro Phe
1               5                   10                  15

Tyr Pro Ile Glu Glu Gly Ser Ala Gly Ile Gln Leu His Lys Tyr Met
            20                  25                  30

Gln Gln Tyr Ala Lys Leu Gly Ala Ile Ala Phe Ser Asn Ala Leu Thr
        35                  40                  45

Gly Val Asp Ile Ser Tyr Gln Glu Tyr Phe Asp Ile Thr Cys Arg Leu
    50                  55                  60

Ala Glu Ala Met Lys Asn Tyr Gly Met Lys Gln Gly Thr Ile Ala
65              70                  75                  80

Leu Cys Ser Glu Asn Cys Glu Glu Phe Phe Met Pro Val Leu Ala Gly
                85                  90                  95

Leu Tyr Ile Gly Val Ala Val Ala Pro Thr Asn Glu Ile Tyr Thr Leu
            100                 105                 110

Arg Glu Leu Asn His Ser Leu Gly Ile Ala Gln Pro Thr Ile Val Phe
        115                 120                 125

Ser Ser Arg Lys Gly Leu Pro Lys Val Leu Glu Val Gln Lys Thr Val
    130                 135                 140

Thr Cys Ile Lys Thr Ile Val Ile Leu Asp Ser Lys Val Asn Phe Gly
145                 150                 155                 160

Gly Tyr Asp Cys Met Glu Thr Phe Ile Lys Lys His Val Glu Leu Gly
                165                 170                 175

Phe Arg Pro Thr Ser Phe Val Pro Ile Asp Val Lys Asn Arg Lys Gln
            180                 185                 190

His Val Ala Leu Leu Met Asn Ser Ser Gly Ser Thr Gly Leu Pro Lys
        195                 200                 205

Gly Val Leu Ile Thr His Glu Gly Thr Val Thr Arg Phe Ser His Ala
    210                 215                 220

Lys Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
                245                 250                 255

Tyr Phe Ala Cys Gly Tyr Arg Val Val Met Leu Thr Lys Phe Asp Glu
            260                 265                 270

Glu Leu Phe Leu Arg Thr Met Gln Asp Tyr Lys Cys Thr Ser Val Ile
        275                 280                 285

Leu Val Pro Thr Leu Phe Ala Ile Leu Asn Lys Ser Glu Leu Ile Asp
    290                 295                 300

Lys Phe Asp Leu Ser Asn Leu Thr Glu Ile Ala Ser Gly Gly Ala Pro
305                 310                 315                 320

Leu Ala Lys Glu Val Gly Glu Ala Val Ala Arg Arg Phe Asn Leu Pro
                325                 330                 335

Gly Val Arg Gln Gly Tyr Gly Leu Thr Glu Thr Thr Ser Ala Phe Ile
            340                 345                 350

Ile Thr Pro Glu Gly Asp Asp Lys Pro Gly Ala Ser Gly Lys Val Val
        355                 360                 365

Pro Leu Phe Lys Val Lys Val Ile Asp Leu Asp Thr Lys Lys Thr Leu
    370                 375                 380

Gly Val Asn Arg Arg Gly Glu Ile Cys Val Lys Gly Pro Ser Leu Met
385                 390                 395                 400

Leu Gly Tyr Leu Asn Asn Pro Glu Ala Thr Lys Glu Thr Ile Asp Asp
```

```
                        405                 410                 415
Glu Gly Trp Leu His Thr Gly Asp Ile Gly Tyr Tyr Asp Glu Asp Glu
                420                 425                 430

His Phe Phe Ile Val Asp Arg Leu Lys Ser Leu Ile Lys Tyr Lys Gly
            435                 440                 445

Tyr Gln Val Pro Pro Ala Glu Leu Glu Ser Val Leu Leu Gln His Pro
        450                 455                 460

Asn Ile Phe Asp Ala Gly Val Ala Gly Val Pro Asp Ser Glu Ala Gly
465                 470                 475                 480

Glu Leu Pro Gly Ala Val Val Met Glu Lys Gly Lys Thr Met Thr
                485                 490                 495

Glu Lys Glu Ile Val Asp Tyr Val Asn Ser Gln Val Val Asn His Lys
                500                 505                 510

Arg Leu Arg Gly Gly Val Arg Phe Val Asp Glu Val Pro Lys Gly Leu
            515                 520                 525

Thr Gly Lys Ile Asp Ala Lys Val Ile Arg Glu Ile Leu Lys Lys Pro
        530                 535                 540

Gln Ala Lys Met
545

<210> SEQ ID NO 57
<211> LENGTH: 548
<212> TYPE: PRT
<213> ORGANISM: Hotaria papariensis

<400> SEQUENCE: 57

Met Glu Met Glu Lys Glu Glu Asn Val Val Tyr Gly Pro Leu Pro Phe
1               5                   10                  15

Tyr Pro Ile Glu Glu Gly Ser Ala Gly Ile Gln Leu His Lys Tyr Met
                20                  25                  30

Gln Gln Tyr Ala Lys Leu Gly Ala Ile Ala Phe Ser Asn Ala Leu Thr
            35                  40                  45

Gly Val Asp Ile Ser Tyr Gln Glu Tyr Phe Asp Ile Thr Cys Arg Leu
        50                  55                  60

Ala Glu Ala Met Lys Asn Tyr Gly Met Lys Gln Gly Thr Ile Ala
65                  70                  75                  80

Leu Cys Ser Glu Asn Cys Glu Glu Phe Phe Ile Pro Val Leu Ala Gly
                85                  90                  95

Leu Tyr Ile Gly Val Ala Val Ala Pro Thr Asn Glu Ile Tyr Thr Leu
                100                 105                 110

Arg Glu Leu Asn His Ser Leu Gly Ile Ala Gln Pro Thr Ile Val Phe
            115                 120                 125

Ser Ser Arg Lys Gly Leu Pro Lys Val Leu Glu Val Gln Lys Thr Val
        130                 135                 140

Thr Cys Ile Lys Thr Ile Val Ile Leu Asp Ser Lys Val Asn Phe Gly
145                 150                 155                 160

Gly Tyr Asp Cys Met Glu Thr Phe Ile Lys Lys His Val Glu Leu Gly
                165                 170                 175

Phe Arg Pro Thr Ser Phe Val Pro Ile Asp Val Lys Asn Arg Lys Gln
            180                 185                 190

His Val Ala Leu Leu Met Asn Ser Ser Gly Ser Thr Gly Leu Pro Lys
        195                 200                 205

Gly Val Leu Ile Thr His Glu Gly Thr Val Thr Arg Phe Ser His Ala
    210                 215                 220

Lys Asp Pro Ile Tyr Gly Asn Gln Val Ser Pro Gly Thr Ala Ile Leu
```

```
            225                 230                 235                 240
Thr Val Val Pro Phe His His Gly Phe Gly Met Phe Thr Thr Leu Gly
                245                 250                 255

Tyr Phe Ala Cys Gly Tyr Arg Val Val Met Leu Thr Lys Phe Asp Glu
            260                 265                 270

Glu Leu Phe Leu Arg Thr Met Gln Asp Tyr Lys Cys Thr Ser Val Ile
        275                 280                 285

Leu Val Pro Thr Leu Phe Ala Ile Leu Asn Lys Ser Glu Leu Ile Asp
    290                 295                 300

Lys Phe Asp Leu Ser Asn Leu Thr Glu Ile Ala Ser Gly Gly Ala Pro
305                 310                 315                 320

Leu Ala Lys Glu Val Gly Glu Ala Val Ala Arg Arg Phe Asn Leu Pro
                325                 330                 335

Gly Val Arg Gln Gly Tyr Gly Leu Thr Glu Thr Thr Ser Ala Phe Ile
            340                 345                 350

Ile Thr Pro Glu Gly Asp Asp Lys Pro Gly Ala Ser Gly Lys Val Val
        355                 360                 365

Pro Leu Phe Lys Val Lys Val Ile Asp Leu Asp Thr Lys Lys Thr Leu
    370                 375                 380

Gly Val Asn Arg Arg Gly Glu Ile Cys Val Lys Gly Pro Ser Leu Met
385                 390                 395                 400

Leu Gly Tyr Leu Asn Asn Pro Glu Ala Thr Lys Glu Thr Ile Asp Asp
                405                 410                 415

Glu Gly Trp Leu His Thr Gly Asp Ile Gly Tyr Tyr Asp Glu Asp Glu
            420                 425                 430

His Phe Phe Ile Val Asp Arg Leu Lys Ser Leu Ile Lys Tyr Lys Gly
        435                 440                 445

Tyr Gln Val Pro Pro Ala Glu Leu Glu Ser Val Leu Leu Gln His Pro
    450                 455                 460

Asn Ile Phe Asp Ala Gly Val Ala Gly Val Pro Asp Ser Glu Ala Gly
465                 470                 475                 480

Glu Leu Pro Gly Ala Val Val Met Glu Lys Gly Lys Thr Met Thr
                485                 490                 495

Glu Lys Glu Ile Val Asp Tyr Val Asn Ser Gln Val Val Asn His Lys
            500                 505                 510

Arg Leu Arg Gly Gly Val Arg Phe Val Asp Glu Val Pro Lys Gly Leu
        515                 520                 525

Thr Gly Lys Ile Asp Ala Lys Val Ile Arg Glu Ile Leu Lys Lys Pro
    530                 535                 540

Gln Ala Lys Met
545

<210> SEQ ID NO 58
<211> LENGTH: 548
<212> TYPE: PRT
<213> ORGANISM: Hotaria tsushimana

<400> SEQUENCE: 58

Met Glu Met Glu Lys Glu Glu Asn Val Val Tyr Gly Pro Leu Pro Phe
1               5                   10                  15

Tyr Pro Ile Glu Glu Gly Ser Ala Gly Ile Gln Leu His Lys Tyr Met
            20                  25                  30

Gln Gln Tyr Ala Lys Leu Gly Ala Ile Ala Phe Ser Asn Ala Leu Thr
        35                  40                  45

Gly Val Asp Ile Ser Tyr Gln Glu Tyr Phe Asp Ile Thr Cys His Leu
```

```
             50              55              60
Ala Glu Ala Met Lys Asn Tyr Gly Met Lys Gln Glu Gly Thr Ile Ala
 65              70              75              80

Leu Cys Ser Glu Asn Cys Glu Glu Phe Phe Ile Pro Val Leu Ala Gly
                 85              90              95

Leu Tyr Ile Gly Val Ala Val Ala Pro Thr Asn Glu Ile Tyr Thr Leu
            100             105             110

Arg Glu Leu Asn His Ser Leu Gly Ile Ala Gln Pro Thr Ile Val Phe
            115             120             125

Ser Ser Arg Lys Gly Leu Pro Lys Val Leu Glu Val Gln Lys Thr Val
130             135             140

Thr Cys Ile Lys Thr Ile Val Ile Leu Asp Ser Lys Val Asn Phe Gly
145             150             155             160

Gly Tyr Asp Cys Met Glu Thr Phe Ile Lys Lys His Val Glu Leu Gly
                165             170             175

Phe Arg Pro Thr Ser Phe Val Pro Ile Asp Val Lys Asn Arg Lys Gln
                180             185             190

His Val Ala Leu Leu Met Asn Ser Ser Gly Ser Thr Gly Leu Pro Lys
                195             200             205

Gly Val Leu Ile Thr His Glu Gly Ala Val Thr Arg Phe Ser His Ala
210             215             220

Lys Asp Pro Ile Tyr Gly Asn Gln Val Ser Pro Gly Thr Ala Ile Leu
225             230             235             240

Thr Val Val Pro Phe His His Gly Phe Gly Met Phe Thr Thr Leu Gly
                245             250             255

Tyr Phe Ala Cys Gly Tyr Arg Val Val Met Leu Thr Lys Phe Asp Glu
                260             265             270

Glu Leu Phe Leu Arg Thr Met Gln Asp Tyr Lys Cys Thr Ser Val Ile
                275             280             285

Leu Val Pro Thr Leu Phe Ala Ile Leu Asn Lys Ser Glu Leu Ile Asp
                290             295             300

Lys Phe Asp Leu Ser Asn Leu Thr Glu Ile Ala Ser Gly Gly Ala Pro
305             310             315             320

Leu Ala Lys Glu Val Gly Glu Ala Val Ala Arg Arg Phe Asn Leu Pro
                325             330             335

Gly Val Arg Gln Gly Tyr Gly Leu Thr Glu Thr Thr Ser Ala Phe Ile
                340             345             350

Ile Thr Pro Glu Gly Asp Asp Lys Pro Gly Ala Ser Gly Lys Val Val
                355             360             365

Pro Leu Phe Lys Val Lys Val Ile Asp Leu Asp Thr Lys Lys Thr Leu
                370             375             380

Gly Val Asn Arg Arg Gly Glu Ile Cys Val Lys Gly Pro Ser Leu Met
385             390             395             400

Leu Gly Tyr Leu Asn Asn Pro Glu Ala Thr Lys Glu Thr Ile Asp Asp
                405             410             415

Glu Gly Trp Leu His Thr Gly Asp Ile Gly Tyr Tyr Asp Glu Asp Glu
                420             425             430

His Phe Phe Ile Val Asp Arg Leu Lys Ser Leu Ile Lys Tyr Lys Gly
                435             440             445

Tyr Gln Val Pro Pro Ala Glu Leu Glu Ser Val Leu Leu Gln His Pro
                450             455             460

Asn Ile Phe Asp Ala Gly Val Ala Gly Val Pro Asp Ser Glu Ala Gly
465             470             475             480
```

```
Glu Leu Pro Gly Ala Val Val Met Glu Lys Gly Lys Thr Met Thr
            485             490             495

Glu Lys Glu Ile Val Asp Tyr Val Asn Ser Gln Val Val Asn His Lys
            500             505             510

Arg Leu Arg Gly Gly Val Arg Phe Val Asp Glu Val Pro Lys Gly Leu
            515             520             525

Thr Gly Lys Ile Asp Ala Lys Val Ile Arg Glu Ile Leu Lys Lys Pro
            530             535             540

Gln Ala Lys Met
545

<210> SEQ ID NO 59
<211> LENGTH: 548
<212> TYPE: PRT
<213> ORGANISM: Hotaria parvula

<400> SEQUENCE: 59

Met Glu Met Glu Lys Glu Glu Asn Val Val Tyr Gly Pro Leu Pro Phe
1               5               10              15

Tyr Pro Ile Glu Glu Gly Ser Ala Gly Ile Gln Leu His Lys Tyr Met
            20              25              30

Gln Gln Tyr Ala Lys Leu Gly Ala Ile Ala Phe Ser Asn Ala Leu Thr
        35              40              45

Gly Val Asp Ile Ser Tyr Gln Glu Tyr Phe Asp Ile Thr Cys Arg Leu
    50              55              60

Ala Glu Ala Met Lys Asn Tyr Gly Met Lys Gln Glu Gly Thr Ile Ala
65              70              75              80

Leu Cys Ser Glu Asn Cys Glu Glu Phe Phe Ile Pro Val Leu Ala Gly
            85              90              95

Leu Tyr Ile Gly Val Ala Val Ala Pro Thr Asn Glu Ile Tyr Thr Leu
            100             105             110

Arg Glu Leu Asn His Ser Leu Gly Ile Ala Gln Pro Thr Ile Val Phe
            115             120             125

Ser Ser Arg Lys Gly Leu Pro Lys Val Leu Glu Val Gln Lys Thr Val
    130             135             140

Thr Cys Ile Lys Thr Ile Val Ile Leu Asp Ser Lys Val Asn Phe Gly
145             150             155             160

Gly His Asp Cys Met Glu Thr Phe Ile Lys Lys His Val Glu Leu Gly
            165             170             175

Phe Pro Pro Thr Ser Phe Val Pro Leu Asp Val Lys Asn Arg Lys Gln
            180             185             190

His Val Ala Leu Leu Met Asn Ser Ser Gly Ser Thr Gly Leu Pro Lys
        195             200             205

Gly Val Arg Ile Thr His Glu Gly Ala Val Thr Arg Phe Ser His Ala
    210             215             220

Lys Asp Pro Ile Tyr Gly Asn Gln Val Ser Pro Gly Thr Ala Ile Leu
225             230             235             240

Thr Val Val Pro Phe His His Gly Phe Gly Met Phe Thr Thr Leu Gly
            245             250             255

Tyr Phe Ala Cys Gly Tyr Arg Val Val Met Leu Thr Lys Phe Asp Glu
            260             265             270

Glu Leu Phe Leu Arg Thr Leu Gln Asp Tyr Lys Cys Thr Ser Val Ile
        275             280             285

Leu Val Pro Thr Leu Phe Ala Ile Leu Asn Lys Ser Glu Leu Ile Asp
    290             295             300
```

```
Lys Phe Asp Leu Ser Asn Leu Thr Glu Ile Ala Ser Gly Gly Ala Pro
305                 310                 315                 320

Leu Ala Lys Glu Val Gly Glu Ala Val Ala Arg Arg Phe Asn Leu Pro
                325                 330                 335

Gly Val Arg Gln Gly Tyr Gly Leu Thr Glu Thr Thr Ser Ala Phe Ile
            340                 345                 350

Ile Thr Pro Glu Gly Asp Asp Lys Pro Gly Ala Ser Gly Lys Val Val
        355                 360                 365

Pro Leu Phe Lys Val Lys Val Ile Asp Leu Asp Thr Lys Lys Thr Leu
    370                 375                 380

Gly Val Asn Arg Arg Gly Glu Ile Cys Val Lys Gly Pro Ser Leu Met
385                 390                 395                 400

Leu Gly Tyr Ser Asn Asn Pro Glu Ala Thr Lys Glu Thr Ile Asp Glu
                405                 410                 415

Glu Gly Trp Leu His Thr Gly Asp Ile Gly Tyr Tyr Asp Glu Asp Glu
            420                 425                 430

His Phe Phe Ile Val Asp Arg Leu Lys Ser Leu Ile Lys Tyr Lys Gly
        435                 440                 445

Tyr Gln Val Pro Pro Ala Glu Leu Glu Ser Val Leu Leu Gln His Pro
    450                 455                 460

Asn Ile Phe Asp Ala Gly Val Ala Gly Val Pro Asp Pro Gln Ala Gly
465                 470                 475                 480

Glu Leu Pro Gly Ala Val Val Met Glu Lys Gly Lys Thr Met Thr
                485                 490                 495

Glu Lys Glu Ile Val Asp Tyr Val Asn Ser Gln Val Val Asn His Lys
            500                 505                 510

Arg Leu Arg Gly Gly Val Arg Phe Val Asp Glu Val Pro Lys Gly Leu
        515                 520                 525

Thr Gly Lys Ile Asp Ala Lys Val Ile Arg Glu Ile Leu Lys Lys Pro
    530                 535                 540

Gln Ala Lys Met
545

<210> SEQ ID NO 60
<211> LENGTH: 548
<212> TYPE: PRT
<213> ORGANISM: Luciola mingrelica

<400> SEQUENCE: 60

Met Glu Met Glu Lys Glu Glu Asn Val Val Tyr Gly Pro Leu Pro Phe
1               5                   10                  15

Tyr Pro Ile Glu Glu Gly Ser Ala Gly Ile Gln Leu His Lys Tyr Met
                20                  25                  30

His Gln Tyr Ala Lys Leu Gly Ala Ile Ala Phe Ser Asn Ala Leu Thr
            35                  40                  45

Gly Val Asp Ile Ser Tyr Gln Glu Tyr Phe Asp Ile Thr Cys Arg Leu
        50                  55                  60

Ala Glu Ala Met Lys Asn Phe Gly Met Lys Pro Glu Glu His Ile Ala
65                  70                  75                  80

Leu Cys Ser Glu Asn Cys Glu Glu Phe Phe Ile Pro Val Leu Ala Gly
                85                  90                  95

Leu Tyr Ile Gly Val Ala Val Ala Pro Thr Asn Glu Ile Tyr Thr Leu
            100                 105                 110

Arg Glu Leu Asn His Ser Leu Gly Ile Ala Gln Pro Thr Ile Val Phe
        115                 120                 125
```

-continued

```
Ser Ser Arg Lys Gly Leu Pro Lys Val Leu Glu Val Gln Lys Thr Val
130                 135                 140

Thr Cys Ile Lys Lys Ile Val Ile Leu Asp Ser Lys Val Asn Phe Gly
145                 150                 155                 160

Gly His Asp Cys Met Glu Thr Phe Ile Lys Lys His Val Glu Leu Gly
                165                 170                 175

Phe Gln Pro Ser Ser Phe Val Pro Ile Asp Val Lys Asn Arg Lys Gln
            180                 185                 190

His Val Ala Leu Leu Met Asn Ser Ser Gly Ser Thr Gly Leu Pro Lys
        195                 200                 205

Gly Val Arg Ile Thr His Glu Gly Ala Val Thr Arg Phe Ser His Ala
210                 215                 220

Lys Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
                245                 250                 255

Tyr Phe Ala Cys Gly Tyr Arg Val Val Met Leu Thr Lys Phe Asp Glu
            260                 265                 270

Glu Leu Phe Leu Arg Thr Leu Gln Asp Tyr Lys Cys Thr Ser Val Ile
        275                 280                 285

Leu Val Pro Thr Leu Phe Ala Ile Leu Asn Lys Ser Glu Leu Ile Asp
290                 295                 300

Lys Phe Asp Leu Ser Asn Leu Thr Glu Ile Ala Ser Gly Gly Ala Pro
305                 310                 315                 320

Leu Ala Lys Glu Val Gly Glu Ala Val Ala Arg Arg Phe Asn Leu Pro
                325                 330                 335

Gly Val Arg Gln Gly Tyr Gly Leu Thr Glu Thr Thr Ser Ala Phe Ile
            340                 345                 350

Ile Thr Pro Glu Gly Asp Asp Lys Pro Gly Ala Ser Gly Lys Val Val
        355                 360                 365

Pro Leu Phe Lys Val Lys Val Ile Asp Leu Asp Thr Lys Lys Thr Leu
370                 375                 380

Gly Val Asn Arg Arg Gly Glu Ile Cys Val Lys Gly Pro Ser Leu Met
385                 390                 395                 400

Leu Gly Tyr Ser Asn Asn Pro Glu Ala Thr Arg Glu Thr Ile Asp Glu
                405                 410                 415

Glu Gly Trp Leu His Thr Gly Asp Ile Gly Tyr Tyr Asp Glu Asp Glu
            420                 425                 430

His Phe Phe Ile Val Asp Arg Leu Lys Ser Leu Ile Lys Tyr Lys Gly
        435                 440                 445

Tyr Gln Val Pro Pro Ala Glu Leu Glu Ser Val Leu Leu Gln His Pro
450                 455                 460

Asn Ile Phe Asp Ala Gly Val Ala Gly Val Pro Asp Pro Asp Ala Gly
465                 470                 475                 480

Glu Leu Pro Gly Ala Val Val Met Glu Lys Gly Lys Thr Met Thr
                485                 490                 495

Glu Lys Glu Ile Val Asp Tyr Val Asn Ser Gln Val Val Asn His Lys
            500                 505                 510

Arg Leu Arg Gly Gly Val Arg Phe Val Asp Glu Val Pro Lys Gly Leu
        515                 520                 525

Thr Gly Lys Ile Asp Ala Lys Val Ile Arg Glu Ile Leu Lys Lys Pro
530                 535                 540

Gln Ala Lys Met
545
```

<210> SEQ ID NO 61
<211> LENGTH: 545
<212> TYPE: PRT
<213> ORGANISM: Photuris pennsylvanica

<400> SEQUENCE: 61

```
Met Glu Asp Lys Asn Ile Leu Tyr Gly Pro Glu Pro Phe His Pro Leu
1               5                   10                  15

Ala Asp Gly Thr Ala Gly Glu Gln Met Phe Tyr Ala Leu Ser Arg Tyr
            20                  25                  30

Ala Asp Ile Ser Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Gly Leu Gln Phe Phe Leu Pro Leu Ile Ala Ser Leu Tyr
                85                  90                  95

Leu Gly Ile Ile Ala Ala Pro Val Ser Asp Lys Tyr Ile Glu Arg Glu
            100                 105                 110

Leu Ile His Ser Leu Gly Ile Val Lys Pro Arg Ile Ile Phe Cys Ser
        115                 120                 125

Lys Asn Thr Phe Gln Lys Val Leu Asn Val Lys Ser Lys Leu Lys Tyr
    130                 135                 140

Val Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ile Asn Leu Asp
                165                 170                 175

Val Lys Lys Phe Lys Pro Asn Ser Phe Asn Arg Asp Asp Gln Val Ala
            180                 185                 190

Leu Val Met Phe Ser Ser Gly Thr Thr Gly Val Ser Lys Gly Val Met
        195                 200                 205

Leu Thr His Lys Asn Ile Val Ala Arg Phe Ser His Cys Lys Asp Pro
    210                 215                 220

Thr Phe Gly Asn Ala Ile Asn Pro Thr Thr Ala Ile Leu Thr Val Ile
225                 230                 235                 240

Pro Phe His His Gly Phe Gly Met Thr Thr Thr Leu Gly Tyr Phe Thr
                245                 250                 255

Cys Gly Phe Arg Val Ala Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Phe Pro Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Asp Thr Asp Val Arg Pro Gly Ser Thr Gly Lys Ile Val Pro Phe His
        355                 360                 365

Ala Val Lys Val Val Asp Pro Thr Thr Gly Lys Ile Leu Gly Pro Asn
    370                 375                 380
```

```
Glu Thr Gly Glu Leu Tyr Phe Lys Gly Asp Met Ile Met Lys Ser Tyr
385                 390                 395                 400

Tyr Asn Asn Glu Glu Ala Thr Lys Ala Ile Ile Asn Lys Asp Gly Trp
            405                 410                 415

Leu Arg Ser Gly Asp Ile Ala Tyr Tyr Asp Asn Asp Gly His Phe Tyr
            420                 425                 430

Ile Val Asp Arg Leu Lys Ser Leu Ile Lys Tyr Lys Gly Tyr Gln Val
            435                 440                 445

Ala Pro Ala Glu Ile Glu Gly Ile Leu Leu Gln His Pro Tyr Ile Val
            450                 455                 460

Asp Ala Gly Val Thr Gly Ile Pro Asp Glu Ala Ala Gly Glu Leu Pro
465                 470                 475                 480

Ala Ala Gly Val Val Val Gln Thr Gly Lys Tyr Leu Asn Glu Gln Ile
            485                 490                 495

Val Gln Asn Phe Val Ser Ser Gln Val Ser Thr Ala Lys Trp Leu Arg
            500                 505                 510

Gly Gly Val Lys Phe Leu Asp Glu Ile Pro Lys Gly Ser Thr Gly Lys
            515                 520                 525

Ile Asp Arg Lys Val Leu Arg Gln Met Phe Glu Lys His Lys Ser Lys
            530                 535                 540

Leu
545

<210> SEQ ID NO 62
<211> LENGTH: 543
<212> TYPE: PRT
<213> ORGANISM: Pyrophorus plagiophthalamus

<400> SEQUENCE: 62

Met Met Lys Arg Glu Lys Asn Val Ile Tyr Gly Pro Glu Pro Leu His
1               5                   10                  15

Pro Leu Glu Asp Lys Thr Ala Gly Glu Met Leu Phe Arg Ala Leu Arg
            20                  25                  30

Lys His Ser His Leu Pro Gln Ala Ile Val Asp Val Phe Gly Asp Glu
            35                  40                  45

Ser Leu Ser Tyr Lys Glu Phe Phe Glu Ala Thr Cys Leu Leu Ala Gln
50                  55                  60

Ser Leu His Asn Cys Gly Tyr Lys Met Asn Asp Val Val Ser Ile Cys
65                  70                  75                  80

Ala Glu Asn Asn Lys Arg Phe Phe Ile Pro Ile Ile Ala Ala Trp Tyr
            85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Cys Thr
            115                 120                 125

Lys Asn Ile Leu Asn Lys Val Leu Glu Val Gln Ser Arg Thr Asn Phe
130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
            165                 170                 175

Asn Phe Lys Pro Leu His Tyr Asp Pro Val Glu Gln Val Ala Ala Ile
            180                 185                 190

Leu Cys Ser Ser Gly Thr Thr Gly Leu Pro Lys Gly Val Met Gln Thr
            195                 200                 205
```

His Gln Asn Ile Cys Val Arg Leu Ile His Ala Leu Asp Pro Glu Ala
    210                 215                 220

Gly Thr Gln Leu Ile Pro Gly Val Thr Val Leu Val Tyr Val Pro Phe
225                 230                 235                 240

Phe His Ala Phe Gly Phe Gly Ile Asn Leu Gly Tyr Phe Met Val Gly
                245                 250                 255

Leu Arg Val Ile Met Leu Arg Arg Phe Glu Gln Glu Ala Phe Leu Lys
            260                 265                 270

Ala Ile Gln Asp Tyr Glu Val Arg Ser Ile Val Asn Val Pro Ala Ile
        275                 280                 285

Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320

Ala Glu Ile Ala Val Lys Arg Leu Asn Leu Pro Gly Ile Arg Cys Gly
                325                 330                 335

Phe Gly Leu Thr Glu Ser Thr Ser Ala Asn Ile His Ser Leu Gly Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
    370                 375                 380

Gly Glu Leu Cys Ile Lys Gly Pro Met Val Ser Lys Gly Tyr Val Asn
385                 390                 395                 400

Asn Val Lys Ala Thr Lys Glu Ala Ile Asp Asp Asp Gly Trp Leu His
                405                 410                 415

Ser Gly Asp Phe Gly Tyr Tyr Asp Glu Asp His Phe Tyr Val Val
            420                 425                 430

Asp Arg Tyr Lys Glu Leu Ile Lys Tyr Lys Gly Ser Gln Val Ala Pro
    435                 440                 445

Ala Glu Leu Glu Glu Ile Leu Leu Lys Asn Pro Cys Ile Arg Asp Val
450                 455                 460

Ala Val Val Gly Ile Pro Asp Leu Glu Ala Gly Glu Leu Pro Ser Ala
465                 470                 475                 480

Phe Val Val Ile Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
    515                 520                 525

Arg Lys Glu Leu Leu Lys Gln Leu Leu Glu Lys Ser Ser Lys Leu
530                 535                 540

<210> SEQ ID NO 63
<211> LENGTH: 543
<212> TYPE: PRT
<213> ORGANISM: Pyrophorus mellifluous

<400> SEQUENCE: 63

Met Met Lys Arg Glu Lys Asn Val Val Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Tyr Gly Glu Glu
        35                  40                  45

-continued

Trp Ile Ser Tyr Lys Glu Phe Phe Glu Thr Thr Cys Leu Leu Ala Gln
 50                  55                  60

Ser Leu His Asn Cys Gly Tyr Lys Met Ser Asp Val Val Ser Ile Cys
 65                  70                  75                  80

Ala Glu Asn Asn Lys Arg Phe Phe Val Pro Ile Ile Ala Ala Trp Tyr
                 85                  90                  95

Ile Gly Met Ile Val Ala Pro Val Asn Glu Gly Tyr Ile Pro Asp Glu
            100                 105                 110

Leu Cys Lys Val Met Gly Ile Ser Arg Pro Gln Leu Val Phe Cys Thr
        115                 120                 125

Lys Asn Ile Leu Asn Lys Val Leu Glu Val Gln Ser Arg Thr Asp Phe
130                 135                 140

Ile Lys Arg Ile Ile Ile Leu Asp Ala Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Tyr Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Arg Asn Val Cys Val Arg Leu Ile His Ala Leu Asp Pro Arg Val
210                 215                 220

Gly Thr Gln Leu Ile Pro Gly Val Thr Val Leu Val Tyr Leu Pro Phe
225                 230                 235                 240

Phe His Ala Phe Gly Phe Ser Ile Asn Leu Gly Tyr Phe Met Val Gly
                245                 250                 255

Leu Arg Val Ile Met Leu Arg Arg Phe Asp Gln Glu Ala Phe Leu Lys
            260                 265                 270

Ala Ile Gln Asp Tyr Glu Val Arg Ser Val Ile Asn Val Pro Ala Ile
        275                 280                 285

Ile Leu Phe Leu Ser Lys Ser Pro Leu Val Asp Lys Tyr Asp Leu Ser
290                 295                 300

Ser Leu Arg Glu Leu Cys Cys Gly Ala Ala Pro Leu Ala Lys Glu Val
305                 310                 315                 320

Ala Glu Ile Ala Val Lys Arg Leu Asn Leu Pro Gly Ile Arg Cys Gly
                325                 330                 335

Phe Gly Leu Thr Glu Ser Thr Ser Ala Asn Ile His Ser Leu Arg Asp
            340                 345                 350

Glu Phe Lys Ser Gly Ser Leu Gly Lys Val Thr Pro Phe Met Ala Val
        355                 360                 365

Lys Ile Ala Asp Arg Glu Thr Gly Lys Ala Leu Gly Pro Asn Gln Val
370                 375                 380

Gly Glu Leu Cys Val Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Ser Gln Val Ala Pro
        435                 440                 445

Ala Glu Leu Glu Glu Ile Leu Leu Lys Asn Pro Cys Ile Arg Asp Val
450                 455                 460

Ala Val Val Gly Ile Pro Asp Leu Glu Ala Gly Glu Leu Pro Ser Ala

```
                465                 470                 475                 480
Phe Val Val Lys Gln Pro Gly Lys Glu Ile Thr Ala Lys Glu Val Tyr
                    485                 490                 495

Asp Tyr Leu Ala Glu Arg Val Ser His Thr Lys Tyr Leu Arg Gly Gly
                500                 505                 510

Val Arg Phe Val Asp Ser Ile Pro Arg Asn Val Thr Gly Lys Ile Thr
            515                 520                 525

Arg Lys Glu Leu Lys Gln Leu Leu Glu Lys Ser Ser Lys Leu
        530                 535                 540

<210> SEQ ID NO 64
<211> LENGTH: 530
<212> TYPE: PRT
<213> ORGANISM: Arachnocampa richardsae

<400> SEQUENCE: 64

Met Ala Cys Thr Ser Val Asn Asn Ile Val Tyr Gly Pro Lys Pro Thr
1               5                   10                  15

Phe Asp Val Leu Lys Glu Ala Asn Ser Tyr Gly Glu Tyr Ala Phe Lys
            20                  25                  30

Arg Leu Arg Ala Arg Gly Asp Glu Val Ser Val Ile Asp Ala Leu Thr
        35                  40                  45

Gly Glu Glu Ile Arg Ala Ser Asp Ile Tyr Ala Lys Thr Val Arg Thr
    50                  55                  60

Ala Glu Cys Leu Gln Ala Tyr Gly Ile Arg Lys Gly Asp Arg Val Gly
65                  70                  75                  80

Ile Cys Ser Asp Thr Met Ile Glu Tyr Tyr Tyr Ile Val Met Gly Thr
                85                  90                  95

Met Ala Val Gly Ala Ile Ile Cys Pro Ile Ile Ile Ser Trp Thr Glu
            100                 105                 110

Ala Asp Met Asn His Ala Phe Asn Ile Ser Cys Pro Thr Val Phe Phe
        115                 120                 125

Val Ser Lys Ser Ile Leu Pro Thr Ile Ala Arg Ile Ala Lys Arg Asn
    130                 135                 140

Pro Tyr Val Lys Asp Ile Ile Val Phe Asp Asp Asn Ala Pro Glu Lys
145                 150                 155                 160

Pro Leu Ile Ser Phe Lys Asp Phe Leu Ala Asn Pro Lys Val Pro Ser
                165                 170                 175

Lys Pro His Phe Asp Cys Glu Pro Gln Asp Met Glu Asn Thr Ile Ala
            180                 185                 190

Thr Val Leu Leu Thr Ser Gly Thr Thr Gly Ile Ser Lys Gly Val Ala
        195                 200                 205

Ile Ser Gln Tyr Asn Leu Ile His Phe Met Ser Leu Asp Thr Lys Thr
    210                 215                 220

Tyr Lys Lys Gly Leu Phe Leu Cys Val Ala Gln Tyr Ser Asn Ala Phe
225                 230                 235                 240

Gly Phe Thr Ala Leu Met Arg Arg Ala Phe Asn Gly Thr Arg Val Leu
                245                 250                 255

His Leu Pro Arg Tyr Asp Glu Lys Ser Tyr Leu Glu Cys Val Gln Lys
            260                 265                 270

Phe Lys Val Asn Tyr Ile Ser Val His Pro Pro Leu Met Leu Ser Leu
        275                 280                 285

Ala Lys Lys Pro Glu Ile Ala Asn Tyr Asp Leu Ser Ser Leu Glu Arg
    290                 295                 300

Ile Tyr Cys Ser Gly Thr Thr Val Ser Val Arg Ile Leu Tyr Gln Val
```

```
              305                 310                 315                 320
Ala Glu Arg Ile Gly Val Lys Val Arg Gln Phe Tyr Gly Ser Ser
                    325                 330                 335

Glu Cys Leu Ala Val Val Ala Gln Ser Asp Glu Phe Cys Thr Lys Gly
                340                 345                 350

Ser Val Gly Thr Leu Met Pro Gly Ile Ile Gly Lys Val Ile His Pro
            355                 360                 365

Glu Thr Gly Ala Leu Leu Gly Pro Asn Glu Arg Gly Phe Leu Lys Phe
        370                 375                 380

Lys Ala Asn Ser Thr Met Tyr Gly Tyr Phe Asn Asn Pro Glu Ala Ser
385                 390                 395                 400

Lys Val Val Lys Asp Glu Gly Tyr Val Asn Thr Gly Asp Ala Gly
                405                 410                 415

Tyr Tyr Asn Glu Arg Phe Glu Trp Phe Val Val Asp Arg Leu Lys Asp
                420                 425                 430

Ile Val Met Val Asp Gly Val Ala Val Ala Pro Thr Glu Met Glu Thr
                435                 440                 445

Thr Ile Leu Leu His Pro Asp Ile Ile Asp Ala Cys Val Ile Gly Ile
        450                 455                 460

Ser Asp Gly Glu Gly Gly Glu Val Leu Phe Ala Phe Leu Thr Lys Thr
465                 470                 475                 480

Arg Lys Glu Val Thr Glu Lys Asp Val Met Asp Phe Val Ala Glu Lys
                485                 490                 495

Leu Pro Tyr Pro Lys His Leu Lys Gly Gly Cys Gln Phe Val Asp Glu
                500                 505                 510

Ile Pro Lys Asn Pro Ala Gly Lys Met Leu Arg Arg Ile Leu Arg Gly
                515                 520                 525

Thr Leu
    530

<210> SEQ ID NO 65
<211> LENGTH: 530
<212> TYPE: PRT
<213> ORGANISM: Arachnocampa tasmaniensis

<400> SEQUENCE: 65

Met Thr Ser Thr Ser Val Asp Asn Ile Val Tyr Gly Pro Lys Pro Lys
1               5                   10                  15

Phe Asp Val Leu Lys Glu Ala Asn Ser Tyr Gly Glu Tyr Thr Phe Lys
                20                  25                  30

Arg Leu Arg Ala Arg Gly Asp Glu Val Ser Val Ile Asp Gly Val Thr
            35                  40                  45

Gly Glu His Ile Thr Ala Ser Thr Ile Tyr Ala Lys Thr Val Arg Thr
        50                  55                  60

Ala Glu Cys Leu Gln Ala Tyr Gly Ile Arg Lys Gly Asp Arg Ile Gly
65                  70                  75                  80

Ile Cys Ser Asp Thr Met Ile Glu Tyr Tyr Ile Val Met Gly Thr
                85                  90                  95

Met Ala Val Gly Ala Ile Ile Cys Pro Val Ile Ile Ser Trp Thr Glu
                100                 105                 110

Ala Asp Met Asn His Ala Phe Asn Ile Ser Cys Pro Thr Val Phe Phe
            115                 120                 125

Val Ser Lys Ser Ile Leu Pro Thr Ile Ala Lys Leu Ser Lys Arg Asn
        130                 135                 140

Pro Tyr Val Lys Asp Ile Ile Val Phe Asp Asp Glu Ser Pro Glu Lys
```

```
                145                 150                 155                 160
        Pro Phe Ile Ser Phe Lys Asp Phe Leu Ala Asn Pro Lys Val Pro Ser
                        165                 170                 175

Lys Pro His Phe Asp Cys Glu Pro Gln Asp Met Glu Ser Thr Ile Ala
                    180                 185                 190

Thr Val Leu Cys Thr Ser Gly Thr Gly Ile Ser Lys Gly Val Ala
                195                 200                 205

Ile Ser Gln Tyr Asn Leu Ile His Phe Met Ser Leu Asp Thr Lys Asn
            210                 215                 220

Asp Lys Lys Gly Leu Phe Leu Cys Val Ala Gln Tyr Ser Asn Ala Phe
        225                 230                 235                 240

Gly Phe Thr Ala Leu Met Arg Arg Ala Phe Asn Gly Thr Arg Val Ile
                        245                 250                 255

His Leu Pro Lys Tyr Glu Glu Lys Ala Tyr Leu Glu Cys Val Gln Lys
                    260                 265                 270

Tyr Lys Val Asn Tyr Ile Ser Val His Pro Leu Met Leu Ser Leu
                275                 280                 285

Ala Lys Lys Pro Glu Ile Val Asn Tyr Asp Leu Ser Ser Leu Glu Arg
            290                 295                 300

Ile Tyr Cys Ser Gly Thr Thr Val Ser Val Arg Ile Leu Tyr Ala Val
        305                 310                 315                 320

Ala Asp Arg Leu Gly Val Asn Tyr Val Arg Gln Phe Tyr Gly Ser Ser
                        325                 330                 335

Glu Cys Leu Ala Val Val Ala Gln Ser Asp Glu Tyr Cys Thr Lys Gly
                    340                 345                 350

Ser Val Gly Thr Leu Met Pro Gly Ile Ile Gly Lys Val Val His Pro
                355                 360                 365

Glu Thr Gly Ala Leu Leu Gly Pro Asn Gln Arg Gly Phe Leu Lys Phe
            370                 375                 380

Lys Ala Asn Ser Thr Met Tyr Gly Tyr Tyr Asn Asn Pro Glu Ala Ser
        385                 390                 395                 400

Lys Val Val Lys Asp Glu Glu Gly Tyr Val Asn Thr Gly Asp Ala Gly
                        405                 410                 415

Tyr Tyr Asn Asp Arg Phe Glu Trp Phe Val Val Asp Arg Leu Lys Asp
                    420                 425                 430

Ile Val Met Val Asp Gly Val Gly Val Ala Pro Thr Glu Met Glu Thr
                435                 440                 445

Val Ile Leu Leu His Pro Asp Ile Ile Asp Ala Cys Val Ile Gly Ile
            450                 455                 460

Ser Asp Gly Glu Gly Gly Glu Ile Leu Phe Ala Phe Leu Thr Lys Thr
        465                 470                 475                 480

Arg Lys Glu Leu Thr Glu Lys Asp Val Met Asp Phe Val Ala Glu Lys
                        485                 490                 495

Leu Pro Tyr Pro Lys His Leu Lys Gly Gly Cys Gln Phe Val Glu Glu
                    500                 505                 510

Ile Pro Lys Asn Pro Ala Gly Lys Met Leu Arg Arg Ile Leu Arg Ser
                515                 520                 525

Thr Leu
            530

<210> SEQ ID NO 66
<211> LENGTH: 529
<212> TYPE: PRT
<213> ORGANISM: Artificial Sequence
<220> FEATURE:
```

<223> OTHER INFORMATION: Arachnocampa consensus sequence

<400> SEQUENCE: 66

```
Met Ala Cys Thr Ser Val Asn Asn Ile Val Tyr Gly Pro Lys Pro Thr
1               5                   10                  15

Phe Asp Val Leu Lys Glu Ala Asn Ser Tyr Gly Glu Tyr Ala Phe Lys
            20                  25                  30

Arg Leu Arg Ala Arg Gly Asp Glu Val Ser Val Ile Asp Ala Leu Thr
        35                  40                  45

Gly Glu Glu Ile Arg Ala Ser Asp Ile Tyr Ala Lys Thr Val Arg Thr
    50                  55                  60

Ala Glu Cys Leu Gln Ala Tyr Gly Ile Arg Lys Gly Asp Arg Val Gly
65                  70                  75                  80

Ile Cys Ser Asp Thr Met Ile Glu Tyr Tyr Ile Val Met Gly Thr
                85                  90                  95

Met Ala Val Gly Ala Ile Ile Cys Pro Ile Ile Ser Trp Thr Glu
                100                 105                 110

Ala Asp Met Asn His Ala Phe Asn Ile Ser Cys Pro Thr Val Phe Phe
            115                 120                 125

Val Ser Lys Ser Ile Leu Pro Thr Ile Ala Arg Ile Ala Lys Arg Asn
130                 135                 140

Pro Tyr Val Lys Asp Ile Ile Val Phe Asp Asp Ala Pro Glu Lys Pro
145                 150                 155                 160

Leu Ile Ser Phe Lys Asp Phe Leu Ala Asn Pro Lys Val Pro Ser Lys
                165                 170                 175

Pro His Phe Asp Cys Glu Pro Gln Asp Met Glu Asn Thr Ile Ala Thr
            180                 185                 190

Val Leu Leu Thr Ser Gly Thr Thr Gly Ile Ser Lys Gly Val Ala Ile
        195                 200                 205

Ser Gln Tyr Asn Leu Ile His Phe Met Ser Leu Asp Thr Lys Thr Tyr
    210                 215                 220

Lys Lys Gly Leu Phe Leu Cys Val Ala Gln Tyr Ser Asn Ala Phe Gly
225                 230                 235                 240

Phe Thr Ala Leu Met Arg Arg Ala Phe Asn Gly Thr Arg Val Leu His
                245                 250                 255

Leu Pro Arg Tyr Asp Glu Lys Ser Tyr Leu Glu Cys Val Gln Lys Phe
            260                 265                 270

Lys Val Asn Tyr Ile Ser Val His Pro Pro Leu Met Leu Ser Leu Ala
        275                 280                 285

Lys Lys Pro Glu Ile Ala Asn Tyr Asp Leu Ser Ser Leu Glu Arg Ile
    290                 295                 300

Tyr Cys Ser Gly Thr Thr Val Ser Val Arg Ile Leu Tyr Gln Val Ala
305                 310                 315                 320

Glu Arg Leu Gly Val Lys Val Val Arg Gln Phe Tyr Gly Ser Ser Glu
                325                 330                 335

Cys Leu Ala Val Val Ala Gln Ser Asp Glu Phe Cys Thr Lys Gly Ser
            340                 345                 350

Val Gly Thr Leu Met Pro Gly Ile Ile Gly Lys Val Ile His Pro Glu
        355                 360                 365

Thr Gly Ala Leu Leu Gly Pro Asn Glu Arg Gly Phe Leu Lys Phe Lys
    370                 375                 380

Ala Asn Ser Thr Met Tyr Gly Tyr Phe Asn Asn Pro Glu Ala Ser Lys
385                 390                 395                 400

Val Val Lys Asp Glu Glu Gly Tyr Val Asn Thr Gly Asp Ala Gly Tyr
```

```
                    405                 410                 415
Tyr Asn Glu Arg Phe Glu Trp Phe Val Val Asp Arg Leu Lys Asp Ile
            420                 425                 430

Val Met Val Asp Gly Val Ala Val Ala Pro Thr Glu Met Glu Thr Thr
        435                 440                 445

Ile Leu Leu His Pro Asp Ile Ile Asp Ala Cys Val Ile Gly Ile Ser
    450                 455                 460

Asp Gly Glu Gly Gly Glu Val Leu Phe Ala Phe Leu Thr Lys Thr Arg
465             470                 475                 480

Lys Glu Val Thr Glu Lys Asp Val Met Asp Phe Val Ala Glu Lys Leu
            485                 490                 495

Pro Tyr Pro Lys His Leu Lys Gly Gly Cys Gln Phe Val Asp Glu Ile
            500                 505                 510

Pro Lys Asn Pro Ala Gly Lys Met Leu Arg Arg Ile Leu Arg Gly Thr
        515                 520                 525

Leu
```

What is claimed is:

1. An isolated peptide comprising an amino acid sequence having at least 94% sequence identity to the amino acid sequence of SEQ ID NO: 2, wherein the isolated peptide has luciferase activity; and wherein the luciferase activity comprises catalysis of a luminescence reaction dependent upon ATP and the luminescence reaction produces an emission spectrum with a maximum emission intensity at wavelengths less than or equal to 530+5 nm.

2. The isolated peptide of claim 1, wherein the amino acid sequence is selected from the group consisting of SEQ ID NO: 2, SEQ ID NO: 6, SEQ ID NO: 8, and SEQ ID NO: 10.

3. The isolated peptide of claim 1, wherein the amino acid sequence consists of SEQ ID NO: 2.

4. An isolated peptide comprising an amino acid sequence having at least 94% sequence identity to the amino acid sequence of SEQ ID NO: 2, and a luciferase activity, wherein the luciferase activity comprises catalysis of a luminescence reaction dependent upon ATP.

* * * * *